US006649416B1

(12) United States Patent
Kauer et al.

(10) Patent No.: US 6,649,416 B1
(45) Date of Patent: Nov. 18, 2003

(54) INTELLIGENT ELECTRO-OPTICAL SENSOR ARRAY AND METHOD FOR ANALYTE DETECTION

(75) Inventors: John S. Kauer, Weston, MA (US); Joel E. White, Millis, MA (US)

(73) Assignee: Trustees of Tufts College, Medford, MA (US)

( * ) Notice: Subject to any disclaimer, the term of this patent is extended or adjusted under 35 U.S.C. 154(b) by 0 days.

(21) Appl. No.: 09/507,210

(22) Filed: Feb. 18, 2000

(51) Int. Cl.[7] ............................................. G01N 21/164
(52) U.S. Cl. .................. 436/164; 422/82.06; 422/82.08
(58) Field of Search ................................ 422/56, 82.06, 422/82.07, 82.08; 436/164, 172

(56) References Cited

U.S. PATENT DOCUMENTS

| 4,859,864 | A | | 8/1989 | Smith |
|---|---|---|---|---|
| 5,063,164 | A | | 11/1991 | Goldstein |
| 5,114,676 | A | * | 5/1992 | Leiner et al. ............ 422/82.06 |
| 5,116,759 | A | | 5/1992 | Klainer et al. |
| 5,244,813 | A | * | 9/1993 | Walt et al. .................. 436/172 |
| 5,405,583 | A | | 4/1995 | Goswami et al. |
| 5,445,795 | A | | 8/1995 | Lancaster et al. |
| 5,512,490 | A | | 4/1996 | Walt et al. |
| 5,674,751 | A | | 10/1997 | Jaduszliwer et al. |
| 5,801,297 | A | | 9/1998 | Mifsud et al. |
| 6,085,576 | A | | 7/2000 | Sunshine et al. |

* cited by examiner

*Primary Examiner*—Jeffrey Snay
(74) *Attorney, Agent, or Firm*—R. Dennis Creehan; David S. Resnick

(57) ABSTRACT

The invention relates to a chemical sensor, sensing system and sensing method which provides for a multi-sensor, cross-reactive, sensor array having a rapid response time, dynamic modulation of sampling parameters, and real-time feedback control of sampling and detection conditions. The device and method provide for smart detection and discrimination of analytes in fluids through intelligent sampling, detection, and control algorithms. The invention further provides for a sensor array having discrete sensor elements dispersed on fluid-permeable, high surface area, porous, textured substrates. The innovative device and method exhibit high sensitivity, discrimination and detection capability for target analytes at ppb and sub ppm concentrations.

34 Claims, 42 Drawing Sheets

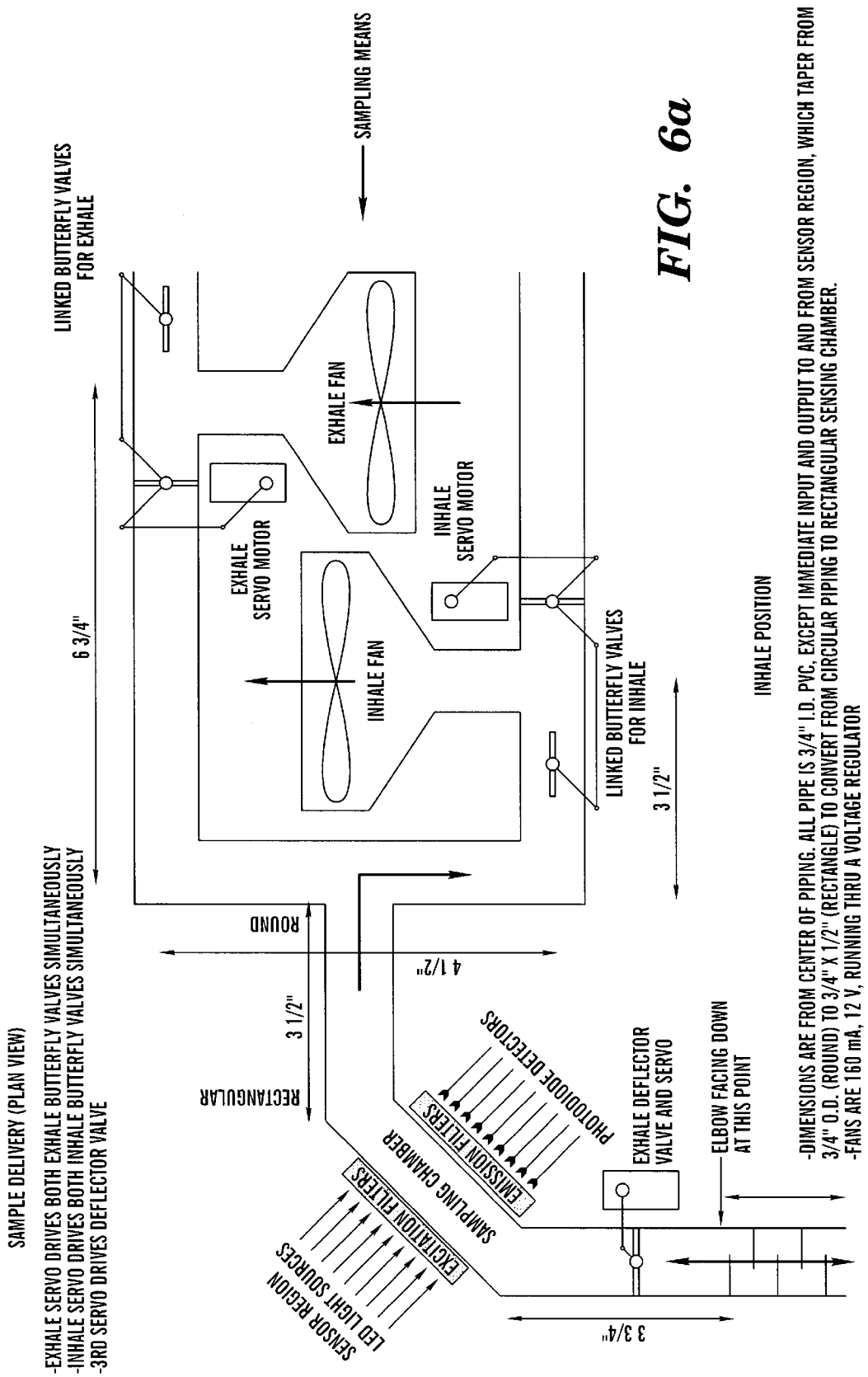

SMART NOSE DATA ACQUISITION TIMING DIAGRAM

OVERVIEW OF SMART NOSE TRAINING

OVERVIEW OF SMART NOSE TESTING

SPECIFIC EXAMPLE OF SMART NOSE TRAINING

SPECIFIC EXAMPLE OF SMART NOSE TESTING

INTELLIGENT ELECTRO-OPTICAL SENSOR ARRAY AND METHOD FOR ANALYTE DETECTION

GOVERNMENT RIGHTS

The invention described herein was supported in part with U.S. Government funding under Defense Advanced Research Projects Agency Contract No. DAAK60-97-K-9502, Office of Naval Research Grant No. 00014-95-1-1340, National Institutes of Health Grant No. R01-DC00228. The U.S. Government has certain rights to this invention.

FIELD OF THE INVENTION

This invention generally relates to sensors and methods for detecting analytes. More particularly, this invention relates to optical sensors, sensor arrays, sensing systems and sensing methods for intelligent sensing and detection of unknown materials by way of real-time feedback and control of sampling conditions.

BACKGROUND OF THE INVENTION

U.S. Pat. No. 4,859,864 to Smith discloses an air bubble sensor that employs light emitting diode (LED) light sources, phototransistor detectors, and displays or alarms for detecting the presence of bubbles in a fluid sample.

U.S. Pat. No. 5,674,751 to Jaduszliwer, et al. disclose a hydrazine fuel fiber optic sensor that employs a diode laser pulsed light source, a calorimetric fiber optic sensor system, and a photodetector to detect changes in spectral absorption due to ppb levels of hydrazine fuel.

U.S. Pat. No. 5,445,795 to Lancaster, et al. disclose a portable optical sensor for detecting volatile organic compounds (VOCs) in vapors and aqueous media. The disclosed device comprises a vapochromic sensor formed from transition metal complex salts, a sensor chamber, a vacuum pump for drawing samples into the chamber, a light source for illuminating the sensor, a light detector responsive to light reflected from the vapochromic sensor, and a detection means for determining a color change in the sensor due to the presence of VOCs. In one disclosed embodiment for fuel tank sensing, the sensor, an LED illuminating light source, and a photodiode detector with an optical band-pass filter are all housed within the sensor chamber and a photodiode feedback signal is provided to a control means for adjusting a fuel metering valve via signal processing electronic circuitry. Other embodiments employ a bi-color LED that can be modulated between two wavelengths and gated detection electronics in the detector is synchronized with LED driver current to monitor small changes in reflected signals at both wavelengths.

U.S. Pat. No. 5,116,759 to Klainer, et al. discloses a vapor or liquid chemical sensor where analytes pass into a sampling cell where they contact sensing solutions for detection. The disclosed device comprises a single illumination source, an optional semi-permeable analyte membrane, a chamber with one or more analyte-sensitive solutions contained in a reservoir cell, a sample signal detector for detecting optical changes in the cell due to the analyte, and an optional reference signal detector for background signal correction. Reagent and sampling pumps are also disclosed for continuously flushing the cell with analyte and solution reagent. The disclosed device employs diodes, lasers or lamps as an excitation source, optically responsive analyte sensing solutions, detectors, and conventional electronic circuitry that are known in the art. In a preferred embodiment, an LED is the preferred light source and a photodiode is the preferred detector. Other embodiments disclose a light source sensor, a source stabilizer, a detector stabilizer, and a temperature sensor and compensator circuitry for feedback, monitoring and stabilizing the light source and detector. Disclosed embodiments include an A/D interface, alarms, display, recorders or plotters for readout, a computer and software.

Persaud and Dodd (*Nature* v. 299, pp. 352–355, Sep. 23, 1982) disclose an electronic nose comprised of semi-selective sensors in a cross-reactive sensor array designed to mimic a mammalian olfactory system. The disclosed sensors comprise commercially available semiconductor transducer gas sensors that exhibit a conductance change when the adsorb ambient vapors. The disclosed sensors were capable of detecting vapors at high concentrations ranging from 0,1 to 10 mols per liter of air. The response time for these sensors ranged from 1 to 3 minutes. Measurements made with various sensor parings demonstrated selectivity toward a number of analyte vapors at high concentrations.

U.S. Pat. No. 5,512,490 to Walt and Kauer disclose a fiber optic sensor with semi-selective sensors in a cross-reactive sensor array that employs spectral recognition patterns for identifying and detecting a variety of analytes. The reference teaches thin film sensors formulated by mixing polymers with dye compounds. The sensors are immobilized on either a solid planar translucent or transparent substrate or a fiber optic fiber or bundle. In a preferred embodiment, the substrate is a transparent optical fiber bindle in which sensors are placed on the ends of optical fibers or groups of such fibers. The sensing system taught by this reference utilizes an arc lamp excitation source, an optical train comprising a series of lenses, filters which are sequentially switched to provide for changes in both excitation light wavelength and emitted light wavelength, and a CCD camera detector which captures spatial images of the fluorescence intensity of individual sensor elements at various wavelengths. The measured responses of individual sensors to analytes are combined to form a pattern of spectral responses over time that are unique to a specific analyte. Spectral response patterns are stored in a library and the response patterns generated from unknown samples are compared with library patterns to identify and detect target analytes. Either light intensity or wavelength may be employed for analyte determinations U.S. Pat. No. 5,063,164 to Goldstein discloses a biomimetic sensor for detecting airborne toxins. The disclosed device comprises a porous, semi-transparent substrate which is sufficiently transmissive to light to permit detection of transmitted light by an LED and photodiode and is impregnated with a self-regenerating sensor. The sensor allegedly mimics the human response to toxins with regard to sensitivity and affinity by employing a molecular encapsulant that contains a chemical sensor reagent. The disclosed device provides for detecting a change in optical density of the sensor which is dependent on toxin concentration and time of exposure. For dilute analyte levels, extended exposure times are required for adequate sensitivity and detection.

Smardzewski [*Talanta* 35(2):95–101(1988)] discloses a multi-element optical waveguide sensor for detecting analytes in fluids which comprises eight fiber optic waveguides each circumferentially coated with sensing material, an array of eight sequentially-activated LEDs optically coupled to the waveguide assembly, and a single detector or array of multiple detectors, photomultiplier tubes or photodiodes, optically coupled to the waveguide assembly. Samples are passed over the outer surface of the coated waveguides and color changes produced by analyte interaction with the coating are monitored. In the disclosed method, each channel is sampled sequentially with measurements made on a single channel before moving to a subsequent channel. In the disclosed method the LEDs are pulsed on and off with switching times of at least one millisecond during measurements. The device provides for sensor signal output to be visually displayed or input to a microprocessor pattern-recognition algorithm. CMOS analog switches/multiplexers are used in feedback loops to control automatic gain-ranging, light-level adjustment and channel-sequencing. The detection limit and sensitivity of the disclosed device and method are limited to ppm levels.

Kopola, et al. [*SPIE*, Fiber Optic Sensors, v. 586, pp. 204–210 (1985)] disclose an eight channel spectrophotometer for measuring spectral reflectance at discrete wavelengths. The disclosed device comprises eight different LED light sources that cover a wavelength range between 480 nm and 1500 nm, a reference and measurement photodiode detector, a temperature controller, a fiber optic probe, signal conditioning electronics, microprocessor controller, and a display and plotter interface. In the disclosed method, measurements of both a reference LED output signal and sample LED output signal, which is modulated by the presence of an analyte, are simultaneously made with a single LED source and each reference and measurement detectors. With the disclosed device and method, sample measurements are time multiplexed with measurements made sequentially for each individual LED channel.

Hauser, et al. [*Meas.Sci.Technol.* 6:1082–1085(1995)] disclose a chemical sensor comprising LED light sources and filtered sample and reference photodiode detectors coupled to a fiber optic for detecting the optical response of a sensing membrane to analytes. The LED is modulated at 2 kHz. The disclosed device provides for a light demodulator for background signal corrections. Detector and reference signals are ratioed to compensate for instability in the LED light source.

The sensitivity of the disclosed device and method apparently is limited to 0.2% or 2000 ppm detection limits. Disclosed sampling times of several minutes or more are apparently required.

Bruno, et al. [*Anal.Chem.* 69(3):507–513(1997)] disclose a six channel sensor array for detecting blood analytes. The disclosed device comprises LED light sources, excitation and emission filters, photodiode detectors, pH membrane sensors and electronic circuitry. The device provides for modulating LED driving current and photodiode gain factors and providing output to a computer via an A/D/converter for display and analysis of data and control of fluid flow to the sensor. The disclosed sensor response time is approximately 30 seconds with a sampling time ranging from 1 to 15 minutes for each sensor. Sensitivity of the device is limited by signal noise caused by temperature and pressure variations due to sample fluid flowing through the sensor cell. An additional limitation with the disclosed device and method is a diminished responsivity of sensors with extended light exposure during sampling due to photobleaching.

Holobar, et al. [*Anal.Methods and Instrum.* 2(2):92–100 (1995)] disclose a double-beam, flow-through pH sensor that employs a sample solution pump, an LED light source and two filtered photodiodes, one as a reference detector and the other as a sample detector. The disclosed sensor response time is approximately 20–30 seconds.

Boisde, et al. [*Chemical and Biochemical Sensing with Optical Fibers and Waveguides*, Artech House (Boston, 1996)] have reviewed the state of fiber optic chemical sensor art and have shown that LED excitation light sources, photodiode detectors, and multi-channel sensor wavelength multiplexing and spatial multiplexing are known in the art.

Taib, et al. [*Analyst* 120(6):1617–1625(1995)] have reviewed solid-state fiber optic sensor instrumentation and have shown that LED light sources, fiber optic light guides, optical transducers for analyte detection, amplifiers, signal processors and output devices are all known in the art of chemical sensor technology. The authors note that LEDs are particularly amenable to high frequency electronic modulation, that the response time of photodiode detectors was in the microsecond range, and that the use of multiple sensor channels with filtered LEDs and photodiodes and microprocessor control of pulsed of LED sources can provide advantageous simultaneous multi-channel/multi-parameter measurements. The authors additionally note that multi-channel sensors may be coupled to microprocessors to carry out parallel signal processing under software control and thereby exploit the capabilities of pattern recognition and artificial neural network methods.

Despite the many advantageous features provided by current chemical sensor technology, there is a need for a chemical sensor, sensing system and sensing method which provide for a multi-sensor, cross-reactive, sensor array having a rapid response time, a rapid sampling time, dynamic modulation of sampling and detection parameters, intelligent feedback control of analyte sampling conditions, smart mode sampling, smart detection through application of sophisticated analyte detection algorithms, and high sensitivity, discrimination, and detection capability for a variety of target analytes at sub ppm to ppb level concentrations.

SUMMARY OF THE INVENTION

The present invention relates to a chemical sensor, sensing system and sensing and identification method which provide for a multi-sensor, cross-reactive, sensor array having a rapid response time, a rapid sampling time, dynamic modulation of sampling and detection parameters, intelligent feedback control of analyte sampling conditions, smart mode sampling, smart detection through application of sophisticated analyte detection algorithms, and high sensitivity, discrimination, and detection capability for a variety of target analytes at sub ppm to ppb level concentrations.

One object of the present invention is to provide a relatively inexpensive, robust, dynamically configurable, portable sensing device.

An additional object of the present invention is to provide for porous or fibrous sensor substrates which enhance the responsivity, selectivity, and discrimination of sensors for target analytes.

A further object of the present invention is to provide for real-time, dynamic configuration of sensor excitation sources, detectors, sampling time and sampling rate to optimize sensor responsivity and selectivity for target analytes in a given sampling environment.

A yet further object of the present invention is to provide for rapid sensor response and rapid detection of low level signals for monitoring sensor temporal response profiles in detecting and discriminating target analytes.

A still further object of the present invention is to provide for an intelligent or "smart" nose that mimics the highly sensitive and discriminating vapor detection capability of olfactory systems of animals An additional object of the present invention is to enable sampling under both negative and positive ambient pressure conditions.

A further object of the present invention is to provide for intelligent sensing of target analytes through electronic modulation of sampling conditions, such as flow rate, sampling duration, and sensor temporal response profiles by way of computer-controlled feedback.

An additional object of the present invention is to provide for removable, interchangeable sensor array substrates for rapidly changing sensor materials and sensor sites in the arrays for either targeting specific analytes or replacing spent sensors when they lose their responsivity to analytes due to either photo-bleaching or chemical reaction.

A further object of the present invention provides for utilization of a wide variety of sensor materials, such as dyes, dye-polymers, and polymers conjugated with dyes, which would normally be considered less suitable with conventional sensing devices due to relatively small analyte response signals.

An additional object of the present invention provides for multiple, cross-reactive sensors deployed in a sensor array for detecting and discriminating a wide variety of target analytes in complex sample mixtures.

Yet another object of the present invention is in providing directly illuminated sensors that do not require epi-illuminating optics which produce undesirable optical signal losses at low response levels.

A further object of the present invention is in providing real-time response signal baseline resetting and high gain response signal amplification tailored to individual sensor elements to avoid detector saturation, eliminate background fluorescence, and provide for simultaneous sampling and discrimination with all sensor elements in the array regardless of relative sensor responsivity to analytes.

BRIEF DESCRIPTION OF THE DRAWINGS

This invention is pointed out with particularity in the appended claims. Other features and benefits of the present invention can be more clearly understood with reference to the specification and the accompanying drawings in which:

FIG. 6a is a schematic diagram of an inhale configuration for the sample delivery module of the present invention;

DETAILED DESCRIPTION OF THE INVENTION

The conceptual basis of the intelligent sensing device and method of the present invention has evolved from studies of biological olfactory systems in which an artificial intelligent sensing system has been developed which provides for cross-reactive sensor arrays tailored to address design issues such as how odors are presented, how the sensing sites are deployed, how the changes in fluorescence are evaluated over time and space, how the analytical circuits are designed, how the data are stored and interpreted, and how pure compounds and mixtures are detected and identified.

I. Overview

Figure 1:
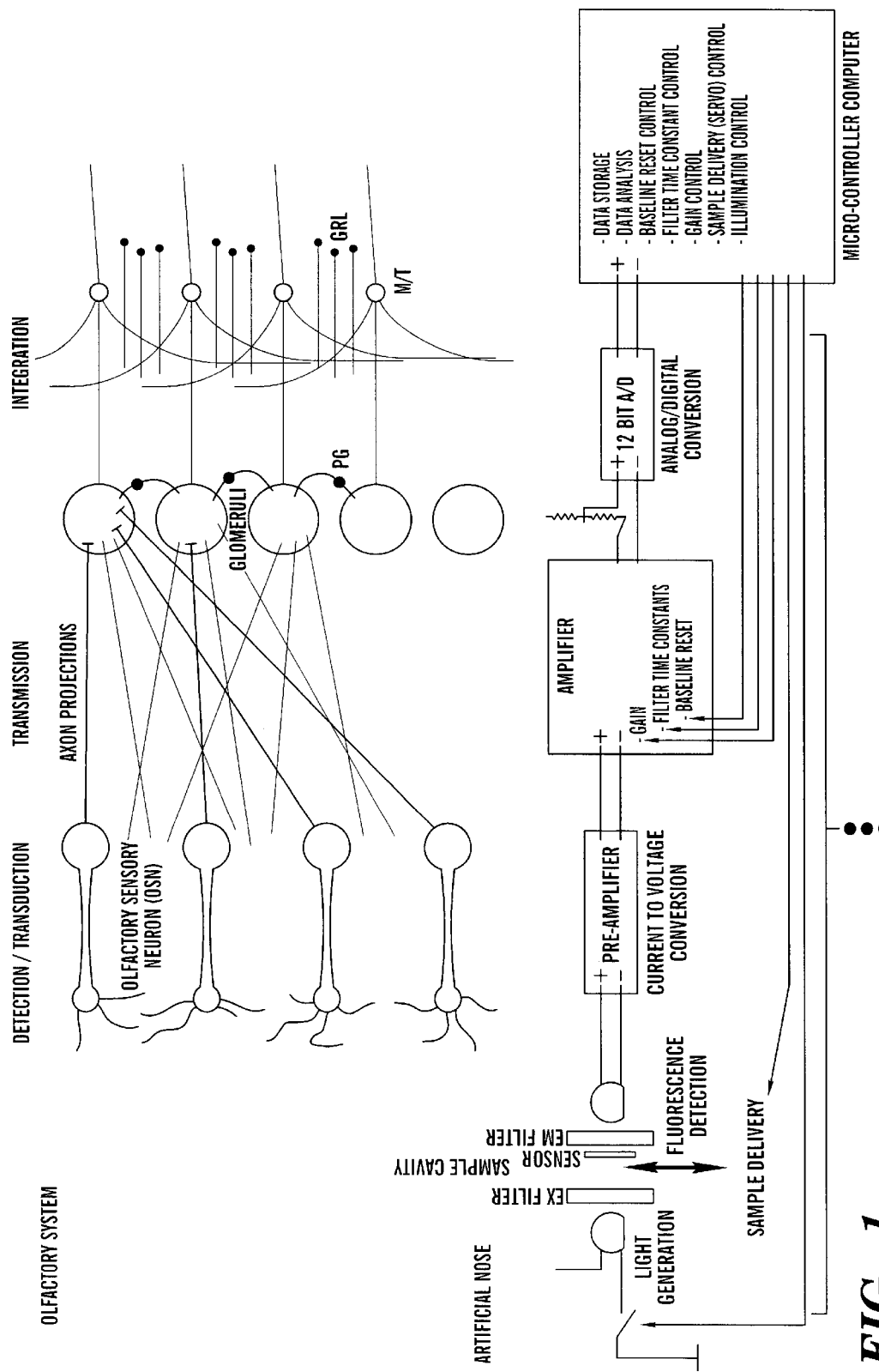
FIG. 1 is a schematic diagram comparing a mammalian olfactory system with the sensing system of the present invention.

FIG. 1 is a schematic diagram comparing a mammalian olfactory system with the sensing system of the present invention. In the peripheral olfactory circuit shown at the top of FIG. 1, many thousands of parallel channels of distributed olfactory sensory neurons ("Detection/Transduction") in the nasal cavity, into which odors are drawn by inhalation, extend convergent axonal projections ("Transmission") to the glomeruli of the olfactory bulb ("Integration"). Periglomerular neurons ("pg") are inhibitory interneurons that connect the glomerulli with one another and modulate mitral/tufted neurons ("M/T") cell activity . The M/T have dendrites extending from the glomeruli to their cell bodies and give rise to axons that leave the olfactory bulb. Granule neurons ("grl") are inhibitory interneurons that modulate M/T cell activity.

The innovative sensing method and sensing device design of the present invention mimics and parallels the structure and operational characteristics of the mammalian olfactory system through the combination of electro-optical hardware component modules, microprocessor control and software sampling and detection algorithms. In the artificial nose embodiment shown in FIG. 1, the sample cavity design mimics the mammalian nasal cavity where odors (i.e. vapor analytes) are drawn into the sensing module ("sniffed" or "inhaled") and their interaction with a plurality of sensing elements ("sensory neurons") in a sensor array triggers an external event. In one embodiment, the analyte interaction with sensing elements produces emitted light energy at a detectable characteristic wavelength when the sensor elements are illuminated by excitation light energy from a filtered LED array. The multi-element sensor array of the present invention thus mimics the sensory neurons of the olfactory system in responding to the external triggering event, emitted light energy signaling the presence of an analyte, and detecting this triggering event by way of a filtered photodiode array ("Detection"). The photodiode preamplifiers mimic an olfactory sensory neuron by converting the optical signal to an electrical voltage signal ("Transduction") which amplified, manipulated and transported via electrical circuits ("Transmission") to an analog-digital ("A/D") converter and a software controlled microprocessor for data manipulation, analysis, feedback control, detection and identification ("Integration"). These features are replicated for each sensor element in the array. While the embodiment shown in FIG. 1 provides for 32 array element channels, the present invention provides for configuring the array with virtually any number of array elements and channels. Thus, the sensor array of the present invention may be expanded or contracted without limit by adding or removing elements and channels according to the requisite analyte detection, discrimination and identification needs of an specific sampling application.

Figure 2:
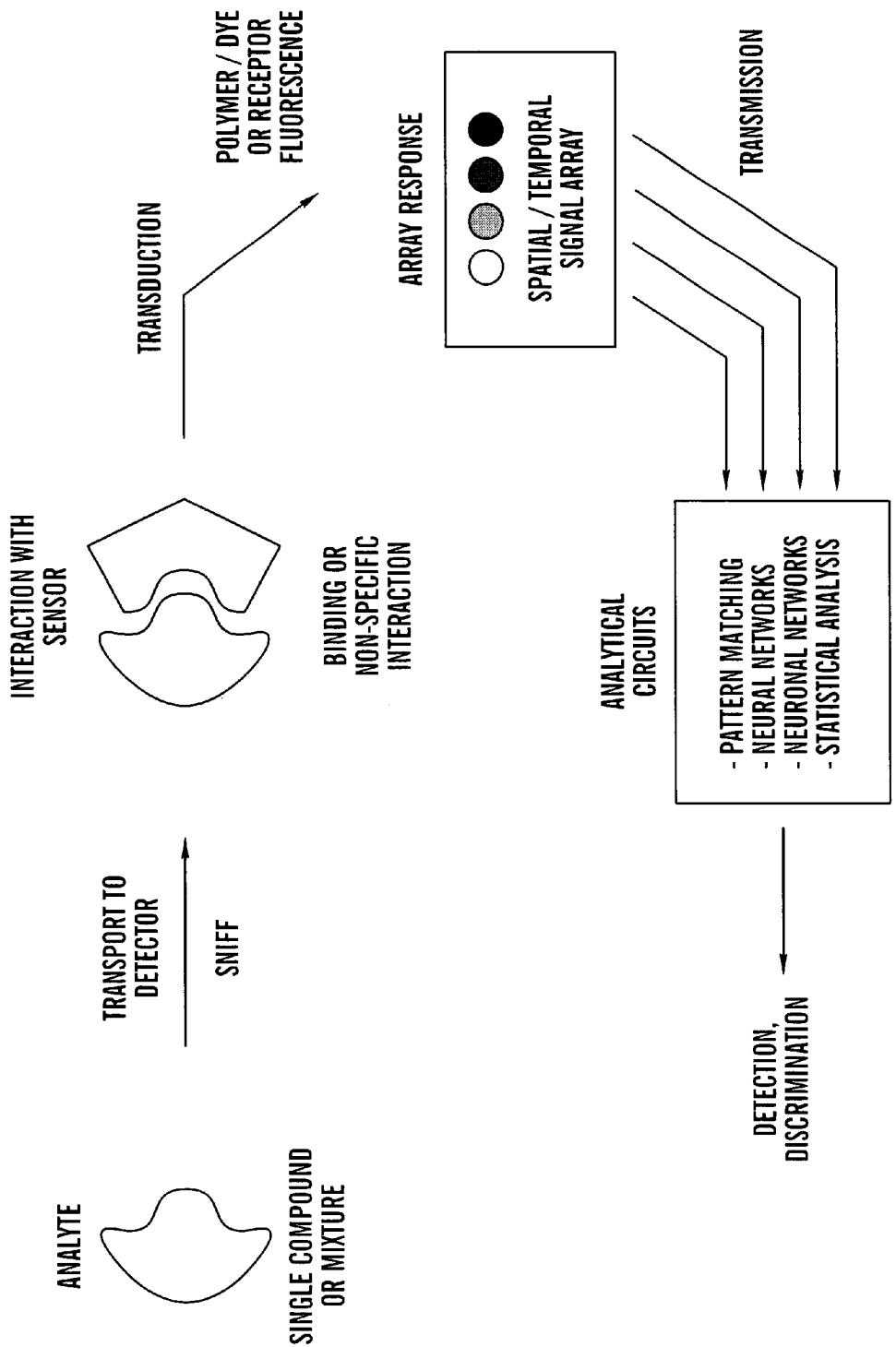
FIG. 2 is a schematic diagram of the analyte detection method of the present invention.

FIG. 2 provides an overview of the analyte sensing and detection method of the present invention. Ambient odors (analytes) are sniffed (transported to the sensor array) where the odors interact with the array sensor elements. Light energy excitation of the sensor elements in the presence of the odors produces a detectable optical response signal due to emitted light produced by analyte interaction with the dyes or dye-polymer compounds in the sensor elements. The spatio-temporal optical response of the array to the odor is detected, recorded, manipulated, and then matched to known target odors via smart analytical algorithms which apply either pattern matching, neural network, neuronal network, or statistical analysis methods to detect, discriminate and identify the odor.

The hardware and software components and configuration of the innovative sensor of the present invention provide for an compact, portable, inexpensive, expandable, rapidly responding sensing device that can modify its detection strategy on the fly. The innovative design and method provides for real-time, on-the-fly, modulation of: a) the output of light emitting diodes (LEDs), such as wavelength, intensity, and frequency; b) the detection properties of photodiodes, such as wavelength, gain, and frequency; c) the sampling parameters, such as frequency, duration, number, velocity, and rise-fall dynamics; and d) sampling time constant or temporal filter settings, for dynamically responsive, smart feedback control in sampling, detection and identification of analytes.

In addition to dynamic response modulation, the device and method further provide for hardware and algorithm implementations which evaluate the synchrony and noise characteristics across different sensors, especially those of the same composition being examined at different wavelengths. This provides a powerful tool for identifying and utilizing small response signals and rejecting noise.

By providing for independently illuminated, detected, recorded, and modulated sensing channels, levels of flexibility, expandability, portability, efficiency, and economy are achieved that are difficult to realize with conventional sensor designs, light sources, filtering systems, and light detectors. In addition, the use of small, inexpensive, flexibly programmable, computational microcomputer platforms and interchangeable sensors and sensor array modules provides for increased flexibility and tailoring of sensor performance and capabilities to real world sensing applications.

I. Sensors

In the sensing device of the present invention, analytes (odors) drawn in and out of the sensing chamber are detected by the fluorescence changes produced by their interaction with sensor elements during irradiation of the sensors with excitation light in the presence of the analytes. For optical sensors which rely on light excitation, absorption and emission, the selection of analyte detection and discriminating dye indicators is important to the design and performance characteristics of a cross-reactive sensor array. An important requirement of candidate dye materials for optical sensor elements is that they produce a characteristic optical response signature in the presence of target analytes. The sensing effect of the dye materials may be based on light fluorescence, absorption, luminescence, phosphorescence, electroluminescence, or other methods for modulation of photonic emission by chemical compounds, such as polymers. These photonic measures may also be dependent on the physical and chemical properties of the substrate, or the presence of additional dye materials.

Typically, for cross-reactive sensor arrays, it is preferable to provide sensor array elements formed from dye materials with different response spectra, different analyte sensitivities, and different analyte discrimination characteristics so as to provide broad spectral detection and discrimination for a variety of analytes. Sensor elements may be comprised of neat dyes, dye compounds, for example conjugated dyes, or dye-polymer mixtures which produce characteristic optical responses to analytes of interest. Sensor materials are generally applied, deposited, or deployed on substrates in the form of fluids, gels, slurries, thin or thick film coatings, beads, droplets, spots, protrusions, fibers, sheets, and other shapes having complex surface textures or protrusions, including fibrilated or hair-like structures.

A. Dye Materials

Generally, any dye that provides a detectable characteristic optical response signature to an analyte at ultraviolet, visible or infrared wavelengths may be employed. Different dye materials may require different excitation and emission wavelengths, which can be accommodated simultaneously in the sensing device of the present invention by appropriate matching LEDs, photodiodes, and light filters wavelengths to required dye wavelengths. In a preferred embodiment, sensors are comprised of a fluorescent dye material applied to a porous or fibrous substrate material.

In a preferred embodiment, dye candidate materials which can be easily applied to and adhere to the innovative fibrous sensor substrates of the present invention are desired. In alternative embodiments, where dye-polymer materials are employed, dye candidates that can be readily incorporated into polymer matrices and whose optical response characteristics are modified by the polymer are desirable. In one embodiment, at least one dye is incorporated into the polymer sensor matrix either by reacting the dye with the polymer to form a dye-polymer compound, or by physically combining the dye and polymer to form a composite mixture of the two materials. In an alternative embodiment, conjugated dyes, such as acryloyl fluorescein and others, may be utilized where it is desirable to incorporate the dye directly into the polymer sensor material by way of covalent bonding.

While the sensor dye may be either a chromophore-type or a fluorophore-type, a fluorescent dye is preferred because the strength of the fluorescent signal typically provides a better signal-to-noise ratio and improves detection of target analytes. In the most preferred embodiment, polarity-sensitive dyes or solvatochromic dyes are utilized. Solvatochromic dyes are dyes whose absorption or emission spectra are sensitive to and altered by the polarity of their surrounding environment. Typically, these dyes exhibit a shift in peak emission wavelength due to a change in local polarity. Polarity changes which cause such wavelength shifts can be introduced by the polymerized matrix used for a particular sensor family, by the presence of a target analyte, or by the combination of the polymer matrix and analyte interaction with the dye. The change in polarity creates a characteristic optical response signature which is useful for detecting specific target analytes. One preferred solvatochromic dye is Nile Red, available from Eastman Kodak (Rochester, N.Y.). Nile Red exhibits large shifts in its emission wavelength peak with changes in the local environment polarity. In addition, Nile Red is soluble in a wide range of solvents, is photochemically stable, and has a relatively strong fluorescence peak. Alternatively, other solvatochromic dyes such as Prodan, 6-propionyl-2-(N,N-dimethylamino)napthalene, or Acrylodan, 6-acryloyl (dimethylamino) napthalene, available from Molecular Probes (Eugene, Oreg.), may be employed.

Additional dyes which are conventionally known in the art and may be used as dyes in the present invention are those found in Tables 3–7 and Table 11 of U.S. Pat. No. 5,512,490 to Walt and Kauer which is incorporated herein by reference. A particularly useful reference for selection of candidate dyes such as metallochromic indicators, including azo and triphenylmethane dyes, and fluorescent indicators, which may be either mixed with or conjugated with polymers to form sensors of the present invention, is *Indicators* [*E. Bishop* (ed.), Pergamon Press (New York 1972)] which is incorporated herein by reference. Another particularly useful reference for selecting appropriate dye indicators is the most recent edition of R. P. Haugland, *Handbook of Fluorescent Probes and Research Chemicals* (6$^{th}$ ed.), Molecular Probes Inc.(Eugene, Oreg., 1996) which is herein incorporated by this reference.

B. Dye-polymer Sensors

Diverse families and types of optical sensor elements may be fabricated as sensors and sensor arrays of the present invention by incorporating sensor dyes, such as metallochromic indicators, fluorescent indicators, or solvatochromic dyes, within various polymer matrices. By combining dyes with different polymers, or combining polymers with different dyes, a wide variety of sensor materials may be produced which exhibit differential sensitivity to analytes (see J. White, et al., *Anal Chem.*, 68:2191–2202(1996)). By incorporating such dyes in sensor elements made from different polymer matrices of varying polarity, hydrophobicity, pore size, flexibility and swelling tendency, unique sensors are produced that react differently with molecules of individual analytes, giving rise to distinguishable and characteristic fluorescence responses when exposed to target analytes. Since the resulting sensor materials may have different excitation and emission wavelengths, LEDs, photodiodes, and excitation and emission filter wavelengths must be appropriated adjusted to match sensor requirements.

1. Polymer Selection

A variety of polymer sensor chemistries may be utilized in fabricating a wide diversity of dye-polymer sensor materials according to the method of the present invention. By way of example, a monomer or oligomer may be selected from any member of the group of condensation polymers derived from such monomers as alcohols, dialcohols, amines, diamines, esters, diesters, carboxylic acids, dicarboxylic acids, diacid chlorides, carbonates, anhydrides, amides, imides, benzoxazoles, benzthiazoles, benzimidazoles, quinozalines, aromatic compounds, including specific polymers such as phenol-formaldehydes, urea-formaldehydes, melamine-formaldehydes, acetyl compounds, lactones, nylons, or polyesters. Alternatively, a monomer may be selected from any member of the group of step-type reaction polymers comprising sulfones, ethers, phenylene oxides, phenylene oxide ethers, Diels-Alder-type reactants, urethanes and arylenes. Monomers may alternatively be selected from any member of the group of vinyl polymers comprising ethylenes, vinyl chlorides, vinylidene chlorides, tetrafluoroethylenes, acrylonitriles, acrylamides, acrylates, methacrylates, acetates, styrenes, methyl styrenes, vinyl esters, vinyl pyrrolidones, butylenes and butadienes.

For optical sensors, sensor elements are typically selected based on distinguishable differences in their characteristic optical response signatures when illuminated by excitation light energy in the presence of a target analyte. In fabricating polymer sensor arrays, polymer sensor elements are selected which have characteristic optical response signatures when mixed with a dye compound and illuminated by excitation light energy in the presence of a target analyte. Thus, preferred optical sensor materials for sensor arrays are selected based on both physical and chemical differences in sensor types which, in combination with a reporter dye compound, produce a characteristic optical response signature in the presence of the analyte when illuminated by excitation light energy.

The following monomer, polymer and copolymer compositions and their derivatives would be particularly useful as candidate polymer materials for dye-polymer optical sensors of the present invention: polyethylene glycol, polycaprolactone, polyarylamide, methyl methacrylate [MMA], 2-hydroxyethyl methacrylate, siloxane, dimethylsiloxane, acrlyamide, methylenebisacrylamide

[MBA], poly (1,4-butylene) adipate, poly (2,6-dimethyl-1,4-phenyleneoxide) [PDPO], triethoxysilyl-modified polybutadiene (50% in toluene) [PS078.5], diethoxymethylsilyl-modified polybutadiene in toluene [PS078.8], acryloxypropylmethyl-cyclosiloxane [CPS2067], (80–85%) dimethyl-(15–20%) (acryloxypropyl) methylsiloxane copolymer [PS802], poly(acryloxypropyl-methyl)siloxane [PS901.5], (97–98%) dimethyl-(2–3%) (methacryloxypropyl)methylsiloxane copolymer [PS851], poly(acrylonitrile-butadiene-styrene)[ PABS], poly(methyl methacrylate), poly(styrene-acrylonitrile 75:25) [PSAN], acryloxypropylmethylsiloxane-dimethylsiloxane copolymer, methylstyrenes, styrenes, acrylic polymers, and methylstyrene divinyl benzene.

2. Polymerization Initiators

In fabricating dye-polymer sensors of the present invention, polymerization of prepolymer mixtures of desired monomer combinations may be achieved by thermal polymerization, condensation polymerization, photoinitiated polymerization, or either crystallization or precipitation from solution followed by annealing.

In one preferred embodiment, thermal polymerization may be utilized either with or without the addition of an initiator. In one embodiment, initiators may be employed to control the rate of thermal polymerization. Since it is often desirable to carry out polymerization of monomer mixtures at low temperature to prevent side reactions, the selection of thermal initiators is generally restricted to organic peroxides, such as dialkyl peroxides or diacylperoxides, organic hydroperoxides, azo compounds, such as azobisisobutyronitrile, and organometallic reagents, such as silver alkyls. Alternatively, thermal initiation may be accomplished by redox agents, for example, in aqueous solutions, a persulfate salt used in combination with a bisulfite ion reducing agent may form an intermediate sulfate radical ion and subsequent hydroxyl radical initiator. Similar redox reaction initiators may be used by combination of alkyl hydroperoxides and a reducing agent, such as ferrous ion. Additionally, some monomers, such as styrenes, undergo free-radical polymerization when heated or exposed to excitation light energy. Alternatively, anionic or cationic polymerization catalysts may also be employed.

In one embodiment, dye-polymer compound synthesis is accomplished by way of condensation polymerization. With this method, no initiator is required and polymerization occurs by way of direct reaction of desired monomers either in the presence or absence of a catalyst to stabilize a metastable intermediate.

In one embodiment, photoinitiated polymerization is utilized. One advantage of photopolymerization is that it offers greater reaction control than thermal polymerization and enables spatial control of local polymerization reactions which can be restricted to regions illuminated by directed light energy. Photopolymerization may be conducted either with or without a specific photosensitizer initiator compound. For example, in the absence of a specific photosensitizer, many candidate monomer materials that can undergo chain reaction polymerization are susceptible to photopolymerization since the absorption of light produces free radicals or ions. Examples of such compounds are unsaturated monomers such as vinyl alkyl ketones, vinyl bromides, styrene, methyl methacrylate and isobutylene.

In one alternative embodiment, a photosensitizer must be added to the prepolymer mixture of monomers for photopolymerization of the polymer. Photosensitizers are compounds that absorb light in a desired region of the spectrum, typically ultraviolet or visible light, and subsequently dissociate into free radicals or transfer absorbed energy directly to a monomer. While some thermal initiators, such as azo compounds and peroxides are also photosensitizers, many alternative initiators may be used as photosensitizers even though they do not dissociate thermally at useful temperatures. Examples of particularly useful photosensitizers are carbonyl compounds, such as acetone, biacetyl benzophenone benzoin, or α-chloroacetone, condensed ring aromatics, such as anthracene, peroxides, such as t-butyl peroxide or hydrogen peroxide, organic sulfides, such as diphenyl disulfide or dibenzoyl disulfide, azo compounds, such as azoisopropane, azobisisobutyronitrile or aryldiazonium salts, halogen-containing compounds, such as chlorine, chloroform, carbon tetrachloride, bromotrichloromethane, bromoform or bromine, metal carbonyls, such as manganese pentcarbonyl and carbon tetrachloride or rhenium pentacarbonyl and carbon tetrachloride, and inorganic ions, such as $FeOH^{+2}$ or $FeCl_4^-$. In one preferred embodiment, benzoin ethyl ether initiator is utilized.

C. Substrates

The present invention provides array sensor element compositions disposed on substrates which may be either inert or active during analyte sampling and detection. While inert supports are typically used in conventional sensing devices, the present invention provides for active dye support materials that enhance sensor responses to specific analytes by their unique chemical, physical, adsorption, or optical characteristics. Different substrate support materials may be employed within a single array where specific support materials are matched to specific dyes, dye compounds and dye polymer mixtures to produce enhanced sensor responses to specific analytes.

An important innovation in the present inventions is the development of fibrous substrate supports which enhance sensor response signals for a variety of dye materials, such as neat dyes, dye compounds, and dye-polymer mixtures. As shown in FIGS. 17a–d, FIG. 18, and FIGS. 19a–b, substantial sensor response enhancements have been achieved with the innovative fibrous supports of the present invention.

An additional advantageous feature of the present invention is in providing for removable or interchangeable arrays, array substrates, or substrate supports to facilitate changing sensor arrays to match specific analyte sampling and detection requirements. In one embodiment, multiple layers of array substrates may be employed for diversification and enhancement of sensor detection capabilities for identifying both broad and specific classes of analytes.

One skilled in the art would recognized that it is generally preferred to position sensor substrates at the appropriate viewing angle and distance from light emitting diode excitation light sources and photodiode detectors so as to provide for optimum sensor signal generation and detection. In one preferred embodiment, a separate substrate holder may be provided for positioning and securing array substrates. In an alternative preferred embodiment, the sample chamber housing may be configured for proper positioning and securing array substrates.

1. Conventional Substrates

As will be appreciated by those in the art, the number of possible substrate materials are very large, and include, but are not limited to, glass and modified or functionalized glass, plastics (including acrylics, polystyrene and copolymers of styrene and other materials, polypropylene, polyethylene, polybutylene, polyurethanes, teflons, etc.), polysaccharides, nylon or nitrocellulose, resins, silica or silica-based materials including silicon and modified silicon, carbon, metals, inorganic glasses, plastics, and a variety of other polymers.

Figure 6B:
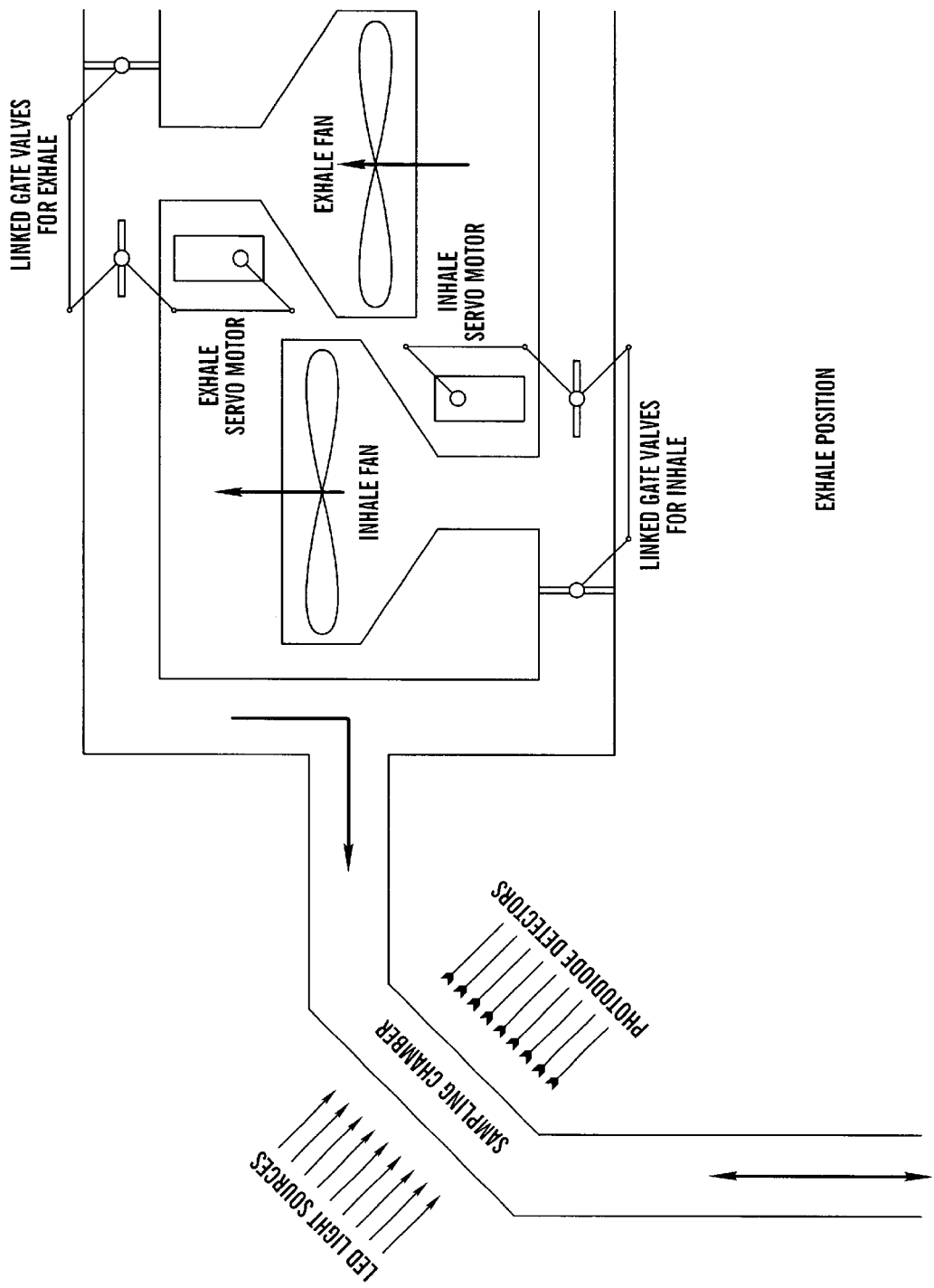
FIG. 6b is a schematic diagram of an exhale configuration for the sample delivery module of the present invention.
Figure 8:
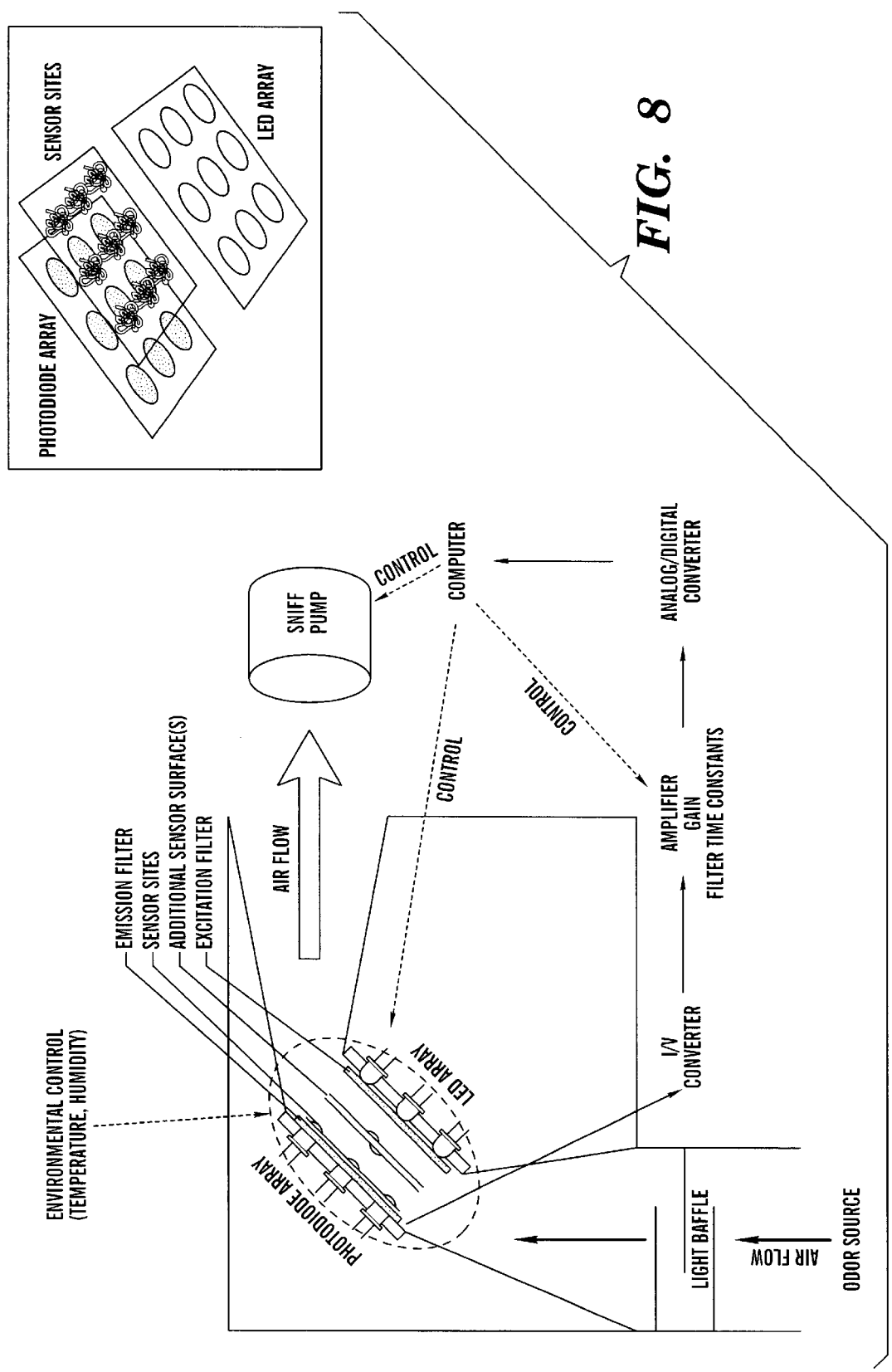
FIG. 8 is a schematic diagram of a sample detection chamber of the present invention.

In preferred embodiments, optically transparent substrates are employed to permit placement of the substrate between LED light sources and photodiode detectors as shown in FIGS. 6a–b and FIG. 8. In alternative embodiments, where the LEDs and photodiodes are placed on the same side of the substrate, optically opaque or optically absorbing, reflective, and scattering materials may be employed.

Where conventional flat, planar, curved or non-planar solid sensor substrates are used, these substrates are generally self-supporting and substrate supports are not required but may be optionally employed.

2. Signal Enhancing Sensor Substrates

While conventional flat, planar, or curved non-planar solid sensor substrates may be employed, increased sensor surface area can arise from depositing dyes on highly convoluted surfaces that include fine fibrous hairs of different materials, particulates, porous substrates, or films and substrates suspended within the sampling stream. With the innovative substrates of the present invention, these preferred substrate embodiments provide enhanced contact and interaction between sample target analytes and sensor elements, increased optical response signal per unit of sensor geometrical surface area, and increased optical response signal per unit of sensor volume.

In preferred embodiments, highly permeable, high surface area, textured, fibrous or particulate substrates which have substantial open porosity for unimpeded transport of vapors and fluids are desired. In preferred embodiments, single or multi-ply layers of papers, felts, laid, or woven fibrous materials or fabrics are employed. In alternative embodiments, loosely packed individual fibrous or particulate materials may be employed.

In a most preferred embodiment, fibrous substrate materials are employed for signal enhancement. Important considerations in selecting fibrous substrates are substrate permeability to vapors, high accessible surface area per unit volume, response signal enhancement for specific analytes, and how the substrate interacts with the sample flow to provide open access of its external and internal surfaces to analytes for interaction with the sensing material dispersed on a plurality of said internal and external substrate surfaces. While particularly useful fiber substrates are porous, lightweight paper or tissue products, for example Kimwipe™ (Kimberly-Clark Corp., Roswell, Ga.), lens papers, facial tissues, and products made from cotton, rayon, glass, and nitrocellulose fibers, other fibrous materials employing natural or synthetic fibers such as felt, batting, textiles, woven fabrics, yarns, threads, string, rope, papers, and laminates or composites of such materials would be equally suitable as long as they possess the requisite fluid permeability, surface area, surface area to volume ratio, and open porosity for free transport of vapor and fluid analytes.

Particularly useful inorganic fibers and fibrous material compositions are natural and synthetic fibers made from glass, ceramic, metal, quartz, silica, silicon, silicate, silicide, silicon carbide, silicon nitride, alumina, aluminate, aluminide, carbon, graphite, boron, borate, boride, and boron nitride. Particularly useful natural or synthetic fibers and fibrous material compositions are polymer fibers made from aromatic polyamides, nylons, polyarylonitrile, polyesters, olefins, acrylics, cellulose, acetates, anidex, aramids, azlon, alatoesters, lyocell, spandex, melamines, modacrylic, nitrile, polybenzinidazole. polyproplylene, rayons, lyorell, sarans, vinyon, triacetate, vinyl, rayon, carbon pitch, epoxies, silicones, sol gels, polyphenylene-benzobis-ozazole, polyphenylene sulfides, polytetrafluoroethylene, teflon, and low density or high density polyethylene. In one preferred embodiment, fiber materials that are highly absorbent and have good dye retention characteristics, for example the cellulosic fiber known as Lyorell, may be employed.

In alternative embodiment, fibers may be coated with either chemical sizing, polymer, ceramic or metallic materials. Chemical sizing such as modified polyvinyl acetates, organosilanes, coupling agents, anti-static agents and lubricants may be employed as appropriate.

With respect to signal enhancing sensor substrate properties of the present invention, one skilled in the art would generally recognize and understand the intended meaning of the term "textured" generally referring to material surfaces which typically have a distribution of surface topographical features, such as high points (peaks) and low points (valleys), ranging from +/−100 nm to +/−1000 um RMS, the term "high permeability" generally referring to materials and material structures with a high open porosity that provide essentially free, unimpeded access and convective or diffusive transport to low viscosity fluids, the term "high surface area" generally referring to materials that have a surface area of at least 1 $M^2/g$ and typically refers to surface areas ranging between 2 to 500 $M^2/g$, the term "high surface area to volume" generally referring to materials having a surface area to volume ratio of at least 1 $M^2/cm^3$ and typically refers to surface area to volume rations ranging between 2 to 1000 $M^2/cm^3$, the terms "porous" or "porosity" generally referring to materials having a distribution of pore sizes ranging from 100 nm to 1000 um, and the term "high open porosity" generally referring to materials whose pore distributions substantially comprise open pores.

3. Chemically-modified substrates

In alternative embodiments, the sensor substrates of the present invention may be chemically or physically modified to enhance surface area, absorption, adhesion, hydrophobicity, hydrophilicity, repulsion, discrimination or specificity. In some embodiments, the substrate my be chemically altered to provide chemical functionality for interaction with analytes, such as providing for enhanced affinity, enhanced repulsion, or steric impediments to analyte adsorption.

D. Sensor Fabrication

As discussed above, sensors may be fabricated from neat dyes, dye polymer compounds, such as intrinsically fluorescing dyes or conjugated dyes, or dye-polymer mixtures applied to convention substrate surfaces or the innovative fibrous substrates of the present invention Neat dye and dye-polymer sensor recipes for the sensors used in Examples 1 and 3 are provided below. Recipes for the sensors used in Examples 2 and 4 are provided elsewhere [see J. White, et al., Anal.Chem. 68(13):2191–2202 (1996) which is incorporated herein by this reference].

1. Neat Dye Sensors

A Nile Red/chloroform solution is prepared by dissolving 1 mg of Nile Red per 1 ml of chloroform. Fiber substrate sensors are typically fabricated by applying approximately. 0.2 mL of dye solution evenly over a 3 cm×3 cm area of substrate material. The solvent is allowed to evaporate, leaving the fibers of the substrate coated and infiltrated with dye. A sensor element is prepared by cutting an approximately 4 mm×4 mm piece of dyed substrate to cover the face of a photodiode. A template representing the photodiode array configuration and photodiode placement is used to position the sensor element on a glass cover slip. The sensor is then held in place by taping the edges. Other methods of securing the sensor are also possible, such as employing glue or mechanical clamping.

2. Dye-Polymer Mixtures

Typically, a sensor made from a dye-polymer mixture is produced by mixing Nile Red solvent solution with a monomer solvent solution. Generally, in preparing sensors from dye-monomer solution mixtures, it is preferable to minimize monomer content and maximize dye content to provide maximum sensor response signal. However, with some analytes, additional monomer is added to provide optimum sensor response signal. The upper limit of monomer additions is generally established by viscosity considerations where low viscosity solutions are desired for application of thin sensor layers or coatings to substrates. While most monomer solutions are prepared with chloroform solvent, some monomers require other solvents such as methanol and toluene.

Nile Red/polyethylene oxide (PEO) sensors are prepared from a solution of 0.007 g of polyethylene oxide dissolved in 1 mL of chloroform. A Nile Red/chloroform solution is prepared by dissolving 1 mg of Nile Red per 1 ml of chloroform. 0.01 ml of the Nile Red solution is added to 1 ml of the monomer solution.

Nile Red/Poly(N-vinylpyrrolidone sensors are prepared from a solution of 0.062 g of monomer [PolySciences, Inc., Warrington, Pa.] dissolved in 1 mL of chloroform. A Nile Red/chloroform solution is prepared by dissolving 1 mg of Nile Red per 1 ml of chloroform. 0.01 ml of the Nile Red solution is added to 1 ml of the monomer cellulose solution.

Nile Red/poly (ethyl cellulose) sensors are prepared from a solution of 0.025 g of ethyl cellulose [PolySciences, Inc.] is dissolved in 1 mL of a 4:1 mixture of toluene and ethanol. A Nile Red/toluene solution is prepared by dissolving 1 mg of Nile Red per 1 ml of toluene. 0.01 ml of the Nile Red solution is added to 1 ml of the monomer solution.

Nile Red/Poly (dimethylsiloxane) sensors are prepared from a solution of 1 mL of Poly(dimethylsilozane) 200 (R) fluid (1000 cP viscosity) [Aldrich Chemical Co., Milwaukee, Wis.] dissolved in 0.5 ml of toluene. A Nile Red/toluene solution is prepared by dissolving 1 mg of Nile Red per 1 ml of toluene. 0.01 ml of the Nile Red solution is added to 1 ml of the monomer solution.

PBA sensors are prepared from a solution of 0.4 g of poly(1,4-butylene adipate) in 1 ml of chloroform to which 0.2 ml of Nile Red chloroform solution (1 mg/ml) is added.

Pentiptycene-derived phenylenecthynylene polymer 1 [SeeYang and Swager in *J.Am.Chem.Soc.* 120:11864–11873 (1998)] sensors are intrinsically fluorescent and do not require dye additions. These sensors are prepared from a solution of 1.2 mg of polymer in 1 mL of chloroform.

For each of the above sensor compositions, sensors are prepared on conventional substrates by applying approximately. 0.2 mL of the monomer or polymer solution mixture evenly over a 3 cm×3cm area of a glass substrate The solvent is allowed to evaporate, leaving the substrate coated with dye. The polymer is cured at room temperature.

Fiber substrate sensors are typically fabricated by applying approximately. 0.2 mL of dye, dye-polymer, or fluorescent polymer solution evenly over a 3 cm×3cm area of substrate material. The solvent is allowed to evaporate, leaving the fibers of the substrate coated and infiltrated with dye. The polymer is cured at room temperature. A sensor element is prepared by cutting an approximately 4 mm×4 mm piece of dyed substrate to cover the face of a photodiode. A template representing the photodiode array configuration and photodiode placement is used to position the sensor element on a glass cover slip. The sensor is then held in place by taping the edges. Other methods of securing the sensor are also possible, such as employing glue or mechanical clamping.

Dow/Alumina sensors are prepared from a solution of 0.062 g of dimethyl siloxane dispersion coating (Dow Corning, Midland, Mich.) dissolved in 2 ml of toluene. A Nile Red/toluene solution is prepared by dissolving 1 mg of Nile Red per 1 ml of toluene. 0.05 ml of the Nile Red solution is added to 1 ml of the monomer solution.

PDPO/Alumina sensors are prepared from a solution of 0.2 g of poly(2,6-dimethyl-1,4-phenyleneoxide) (Aldrich Chemical, Milwaukee, Wis.) dissolved in 1.5 ml of chloroform. A Nile Red/toluene solution is prepared by dissolving 1 mg of Nile Red per 1 ml of toluene. 0.375 ml of the Nile Red solution is added to 1 ml of the monomer solution.

PC/Alumina sensors are prepared from a solution of 0.19 g of polycaprolactone (2,6-dimethyl-1,4-phenyleneoxide) (Aldrich Chemical) dissolved in 1.5 ml of chloroform. A Nile Red/toluene solution is prepared by dissolving 1 mg of Nile Red per 1 ml of toluene. 0.05 ml of the Nile Red solution is added to 1 ml of the monomer solution.

For each of the above polymer/alumina sensor compositions, sensors are prepared on conventional substrates with alumina power additions. 150 mesh alumina powder (Aldrich Chemical) is treated with a 1 mg/ml solution of Nile Red in toluene. The alumina is washed in toluene to remove excess dye and allowed to dry overnight. A droplet of the dye-monomer-solvent solution is applied to a glass coverslip substrate and the Nile Red stained alumina powder is sprinkled over the monomer solution droplet. The monomer-alumina mixture is then polymerized at room temperature.

The Celluse/Alumina/Cellulose fiber optic sensors described in Example 4 are prepared from the ethyl cellulose solution described above. Fiber ends were dipped in the ethyl cellulose preparation, allowed to air dry for 1 min, and dipped in the Nile Red treated alumina powder. After air drying for 1 min, the fiber was dipped in the ethyl cellolose solution again and air cured.

The PC/PSAN/Alumina fiber optic sensors described in Example 4 are prepared from a 0.2 ml solution of 0.2 g of polycaprolactone dissolved in 2.0 ml of chloroform and a 0.2 ml solution of 0.2 g of poly styrene-acrylonitrile dissolved in 2.0 ml of chloroform. A fiber end is dipped in the polymer mixture, allowed to air dry for approximately 1 min, and then dipped into the Nile Red treated alumina powder (see above) and cured at room temperature.

The Cellulose/PDPO/Beads fiber optic sensors described in Example 4 are prepared from a 0.2 ml solution of 0.2 g of poly (2,6-dimethyl-1,4-phenyleneoxide) (Aldrich Chemical) dissolved in 1.5 ml of chloroform and a 0.2 ml solution of the ethyl cellulose solution described above. The beads were 80–100 mesh alumina stained with a 1 mg/1 ml solution of Nile Red in toluene and washed in toluene. A fiber end is dipped in the polymer mixture, allowed to air dry for approximately 1 min, and then dipped in the treated alumina beads and cured at room temperature.

The RMS-044 fiber optic sensors described in Example 4 are prepared from a solution of 0.746 g of 4–6% (methacryloxyproply) methyl-siloxane, dimethyl siloxane copolymer (United Chemical Tech.) in 1.8 ml of chloroform to which 60 mg of BEE photoinitiator is added. A fiber end is dipped in the polymer solution and the polymer is photopolymerized by exposing the fiber end to 4500 mW/cm$^2$ of ultraviolet light for 17 seconds. The photo-polymerization method was described previously [see J.White, et al., *Anal.Chem.* 68(13):2191–2202 (1996)].

The PS901.5 fiber optic sensors described in Example 4 are prepared from a solution of 0.5 ml poly (acryloxxypropylmethl) siloxane in 0.5 ml of chloroform to which 20 mg of BEE photoinitiator is added. A fiber end is dipped in the polymer solution and the polymer is photo-polymerized in the same manner as the RMS-044 sensor above.

The PS802/PS901.5 fiber optic sensors described in Example 4 are prepared from a solution of 0.6 ml of (80–85%) dimethyl (15–20%) acryloxypropyl) methylsiloxane copolymer in 0.4 ml of chloroform to which 60 mg of BEE initiator is added. 0.1 ml of this solution is mixed with 0.1 ml of the PS901.5 solution (see above) and a fiber end is dipped in the copolymer solution. The copolymer mixture is photo-polymerizeds in the same manner as the RMS-044 sensor above except the exposure time was 20 seconds.

II. Sensing System

The innovative sensor and sensing system of the present invention provides for a rapidly responding, relatively inexpensive, dynamically configurable, intelligent, portable artificial sampling device. Innovative features of the device and method of the present invention include innovative sensor substrates for enhancing response signals, improved analyte sensitivity and discrimination, real-time ambient environment sampling, smart training and sampling modes, and intelligent, real-time modulation and control of the sampling and detecting methods and hardware components for adaptive learning and optimization of sampling conditions for specific sampling environments and target analytes.

The innovative device delivers analytes (odors) in a controlled, pulsatile manner (sniff) to fluorescence-based sensor array and detector array system that generates analog electrical signals. The number of sensors, detectors, and sampling time points are arbitrary and can be made larger or smaller depending on the classes of analytes that are being targeted for detection. These analog signals are amplified and filtered by a pre-amplifier/amplifier module and digitized to 12 bits by an analog/digital conversion module for storage in a computer memory module. All attributes of the sensing process, including odor delivery, sampling, analysis, detection and identification are under programmable software control via a computer.

The sensing device must be trained in order to recognize specific analytes. Training consists of delivering a known set of various analytes to the device, one analyte at a time, and storing matrices of values that are a spatio-temporal signatures of each analyte in memory. When an unknown fluid is to be sampled after training, it is delivered to the device and a matrix of values acquired from the unknown is compared to matrix templates for the variety of analytes stored in memory during the training phase. The best match between the unknown and the library of stored matrices is then determined using a number of different algorithms. In one embodiment, the algorithm looks for the best match after calculating the sum of the squared differences between each point in the stored and unknown matrices.

Figure 20:
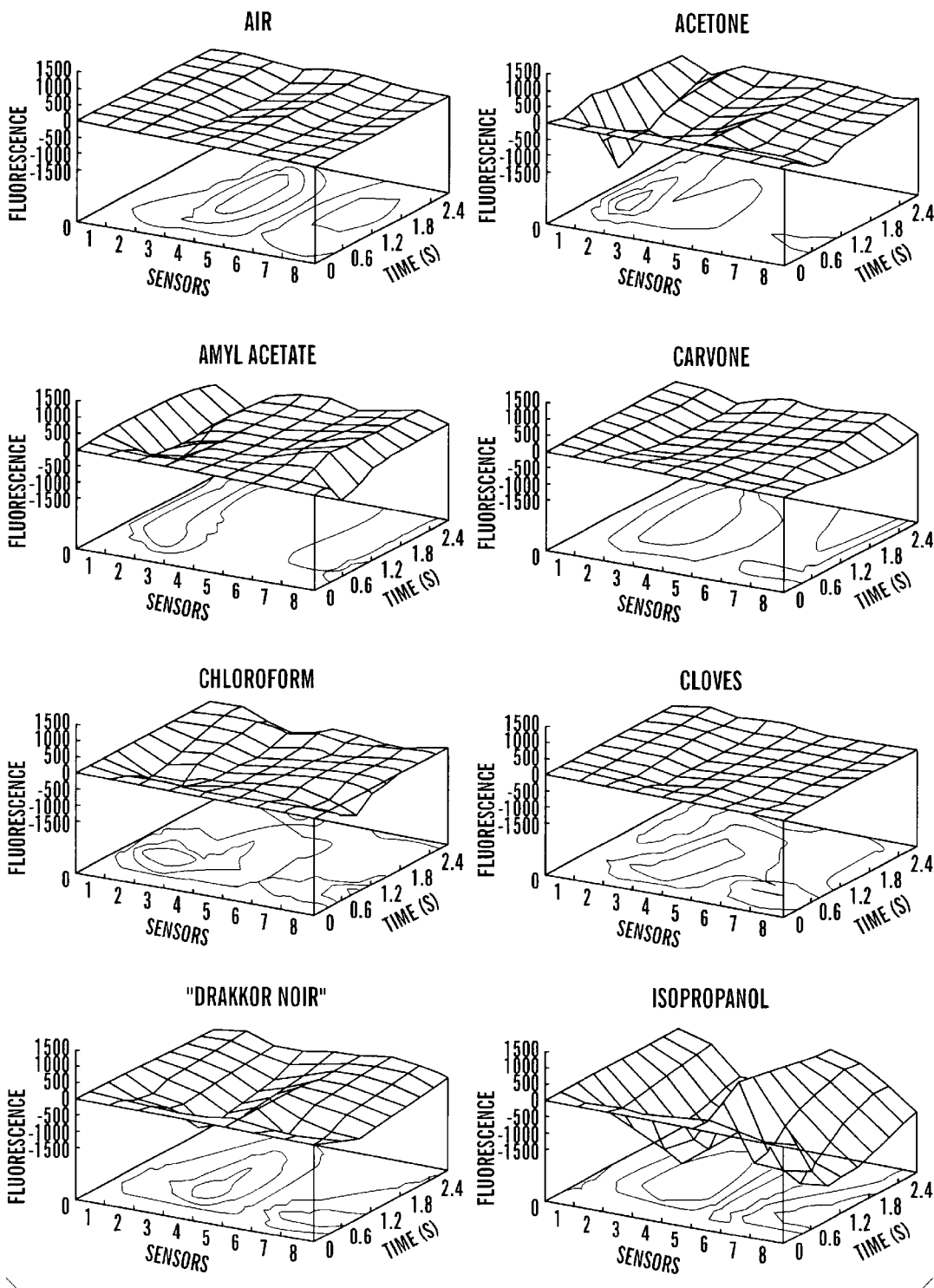
FIG. 20 show time-sensor contour plots of fluorescence intensity for a nine element sensor array of the present invention when exposed to various analytes.

The sensing system provides output results in a variety formats including, but not limited to screen displays, plots, printouts, database files, and synthesized voice messages. typical sensor output is shown in FIG. 20 where a plot of the unique spatio-temporal fluorescence responses of the array sensors to various analytes is provided.

A. Device Overview

The sensing device of the present invention comprises a sampling chamber housing an analyte delivery system and a multi-channel array comprising light emitting diodes (LEDs) focussed through an array of excitation filters onto individual sensor elements of a sensor array. An array of photodiodes, filtered with an array of emission filters, detects emitted light energy produced by illuminating the sensor elements with LED excitation light during interaction with analytes that are drawn into the sample chamber by the analyte delivery system. The ambient temperature, humidity, and particulate levels in the sample chamber may be controlled for improved reproducibility in sampling under a variety of environmental conditions.

The changes in emitted light detected by the photodiode array for each sensor element are digitized by either 12 bit or, alternatively, 24 bit analogue-to-digital converters and stored in a computer memory module. Analyte sampling, detection, and identification are controlled by a programmable microcontroller directed by smart sampling and detection algorithms. The device provides for fast, high gain, low noise, real-time sampling, detection and identification of a variety of vapor analytes with high sensitivity and low detection limits, typically in the sub ppm to ppb concentration range. The innovative device further provides for intelligent sampling and detection through real-time, dynamic modulation of sampling conditions and detection criteria with real-time feedback control for optimizing device sensitivity, discrimination, and detection of a variety of analytes.

B. System Components

The sensing device of the present invention provides for generating optimized signals for different dye/polymer combinations by using different excitation and emission wavelengths for different sensor types. Unlike conventional sensing devices, with the present invention, this can be achieved simultaneously while sampling the entire array of sensing elements in parallel using an array of individual LED-sensor-photodiode sensing channels operating at appropriate wavelengths for a variety of sensor-analyte combinations.

The sensing device generally provides the basic function comprising analyte delivery and control (i.e. manipulation of spatial and temporal distributions; control over temperature, humidity, and duty cycle), detection by a sensor array and transduction of sensor signals into a manipulatable format, analysis of transduction output events, and dynamic feedback control over analyte delivery, detection and analysis for intelligent sampling and detection and optimization of sensor sensitivity and analyte discrimination.

Figure 3:
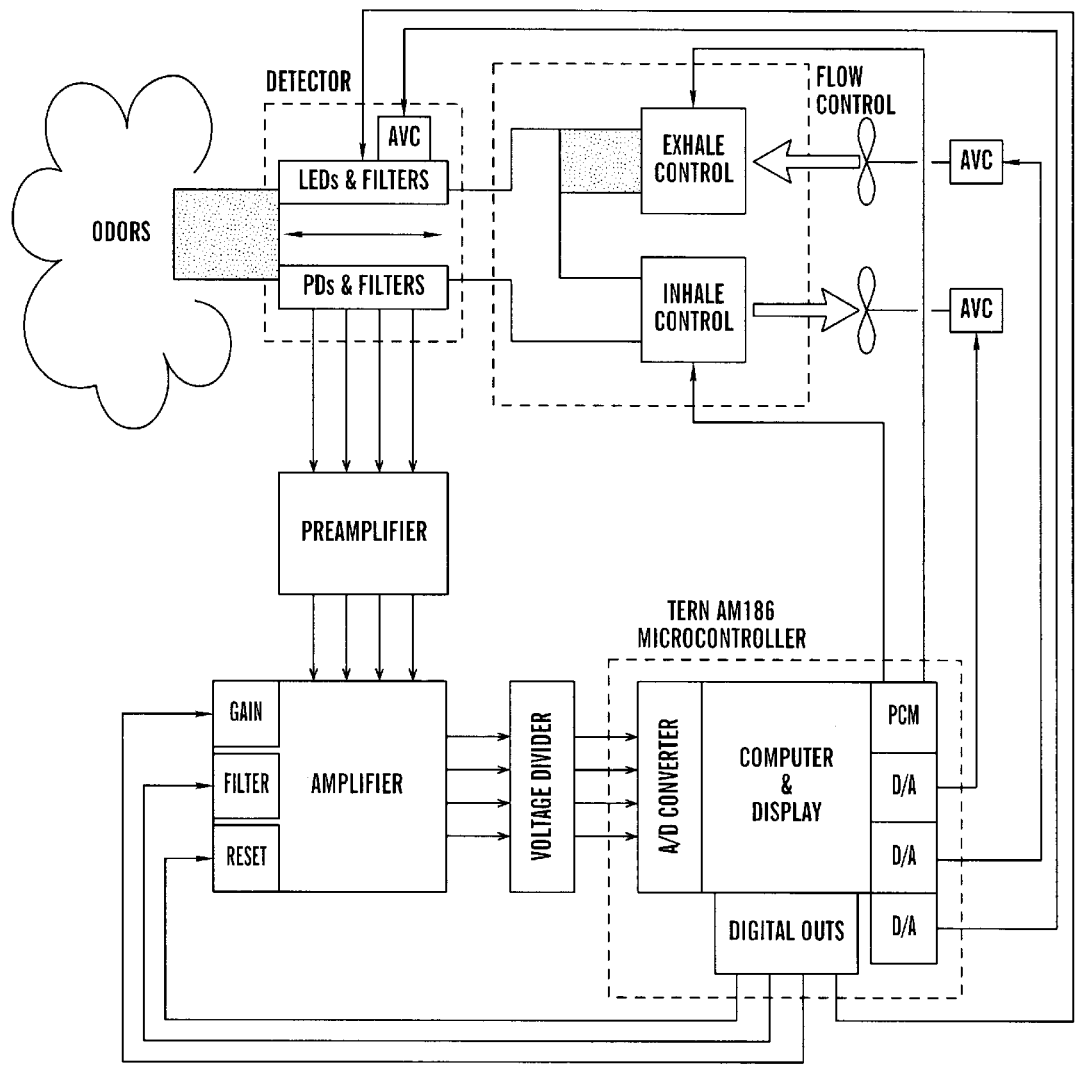
FIG. 3 is a block diagram showing hardware components of the sensing system of the present invention.
Figure 4:
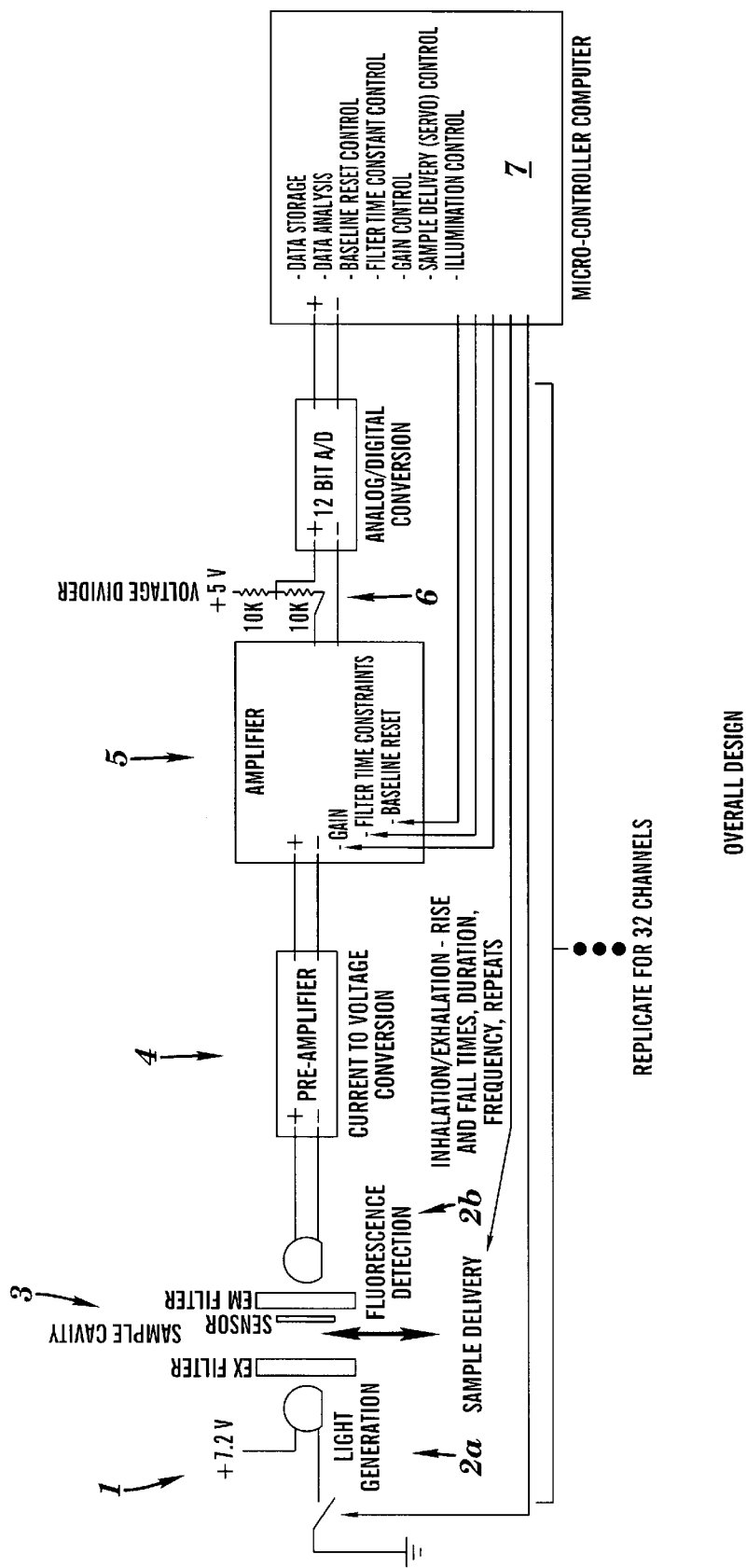
FIG. 4 is a block diagram of electrical component modules of the sensing system of the present invention.

FIGS. 3 and 4 provide schematic block diagrams showing the general modular design and configuration of the sensor array and sensing system components. Details of the sample or analyte delivery module are shown schematically in FIGS. 6a–b. A detailed schematic of the sensor array configuration of LEDs, excitation filters, sensor elements, emission filters, and photodiodes is provided in FIG. 8. The relative locations and configuration of LEDs, sensor elements, photodiodes, and emission/excitation filters are shown in FIG. 13. Detailed circuit schematics are provided for LED array controls (FIG. 5), analyte delivery fans and control valve controls (FIG. 7), photodiode preamplifier module (FIG. 9), amplifier module (FIG. 10), connections into analog to digital conversion module (FIG. 11), and computer control module and pre-amp/amp power board (FIG. 12).

These modular components are described in detail in the following sections.

C. Analyte Delivery

1. Overview

For reliable and reproducible sampling of ambient fluids, it is important to standardize sampling and sensing conditions by controlling the delivery and presentation of analytes to the sensor array. In a preferred embodiment, the analyte deliver system provides feedback control over sample temperature, humidity, flow-rate, and the rise and fall times, duration, and frequency of analyte delivery.

One embodiment of the analyte delivery system is shown in FIGS. 6a–b and FIG. 8. Generally the sensing chamber consists of a rectangular tube through which the analyte vapor passes. The sensing array with opposed light emitting diode light sources and photodiode photodetectors with sensor elements is placed within a sample chamber. In this configuration the incoming fluid stream generated by a gated negative pressure (i.e. a sniff pump such as a fan, pump, 'mesopump', bellows, or their equivalents) causes the fluid stream to be drawn into the sensing chamber and to be expelled to the ambient environment by the negative pressure source. In this manner, analyte vapor pulses are delivered to the sensing array from ambient pressure sources. The sensing chamber can be of the form of a simple tube, as described above, or may assume any shape that may improve or optimize the delivery of the analyte pulse to the sensor array, including complex shapes modeled after the structure of the nasal cavity of animals. In one embodiment, complex cavities with multiple baffles are used to prevent ambient light and ambient air movements from interfering with the generation of standardized pulses of analyte to the sensor array.

Generally, the sensing chamber includes: a) a means for controlling temperature, humidity, flowrate, rise and fall times and frequency of the applied vapor pulses; b) a means for controlling the surface properties of the sensing and non-sensing areas of the chamber (liquid, mucus, or gel lining) in order to impart chromatographic surfaces to the sensing area and/or humidify, dehumidify, or distribute the analyte to the sensory surface, or to optimize response of the sensing chemistry; c) a means for aerodynamic control over chamber shape which may either be held constant for the duration of analyte delivery or modulated by feedback control during analyte delivery; and d) a means for active, dynamic feedback control over shape, duration, flowrate, temporal envelope, and frequency of analyte sampling (sniffing). Such feedback may be derived from examining the spatio-temporal response patterns from the sensor array produced by prior analyte sampling.

2. Sensor Chamber Design

A cross-sectional view of a sampling chamber embodiment showing 9 detection sites is provided in FIG. 8. In designing the sampling chamber, it was necessary to configure the chamber, sensors, LEDs and photodiodes to comply with focal length dimensions of the integral lenses that were incorporated into the LEDs and photodiodes. Focal lengths of the integral lenses were measured and, based on these dimensions, the width of the sample chamber and the positions of the sensors within the sample chamber were arranged such that the sensors were optimally illuminated by the LEDs and optimally observed by the photodiodes at their respective appropriate focal distances.

The present invention provides for control over the sensing chamber environment where, for example, ambient light levels, aerodynamic flow conditions, sample humidity and temperature can be measured, standardized, controlled, adjusted, or modulated for different analyte detection tasks.

The sensing chamber can be optimized for its aerodynamic properties by placing the detectors in cavities of various shapes. In one embodiment, the sensors may be placed at a bend in the flow path. In an alternative embodiment, the sensors may be located on the side of the straight flow path. Since the present device is unique in its use of ambient flow sniffing and dynamic information gathering, the present invention provides an opportunity to exploit the aerodynamic properties of complex spaces for improved sampling performance. For example, the chamber space may be configured to mimic the actual shape of the mammalian nasal cavity, or, alternatively, it may be configured to provide preferred fluid flow or aerodynamic design features. These embodiments would complement the design capability of the present invention which provides for static and dynamic control and modulation of inhalation and exhalation during sampling.

In one embodiment, humidification of the chamber and analyte sample is achieved by humidifying the incoming (inhalation) air stream in the entry nozzle and outgoing (exhalation) air stream in the exhaust pathway, both of which pass over the sensor array. In one method, humidification is accomplished by placing an absorbent material, such as filter paper, within the air tubing. The absorbent surfaces are connected by wicks to vials of water, thereby keeping them moist. In alternative embodiments, the humidity of the source may also be modulated by spraying water mist on the sampling area before sniffing. This will frequently increase the volatility of odors and improve detectability. While other humidification methods may be employed, the primary objective is to provide a means for balancing the humidity levels of the ambient air with those of the analyte source. In a preferred embodiment, precise control of humidity in the chamber could be accomplished by using specific chamber sensors to detect humidity levels which supply feedback to a moisture metering system.

3. Sniffing Fans and Valve System

Figure 7:
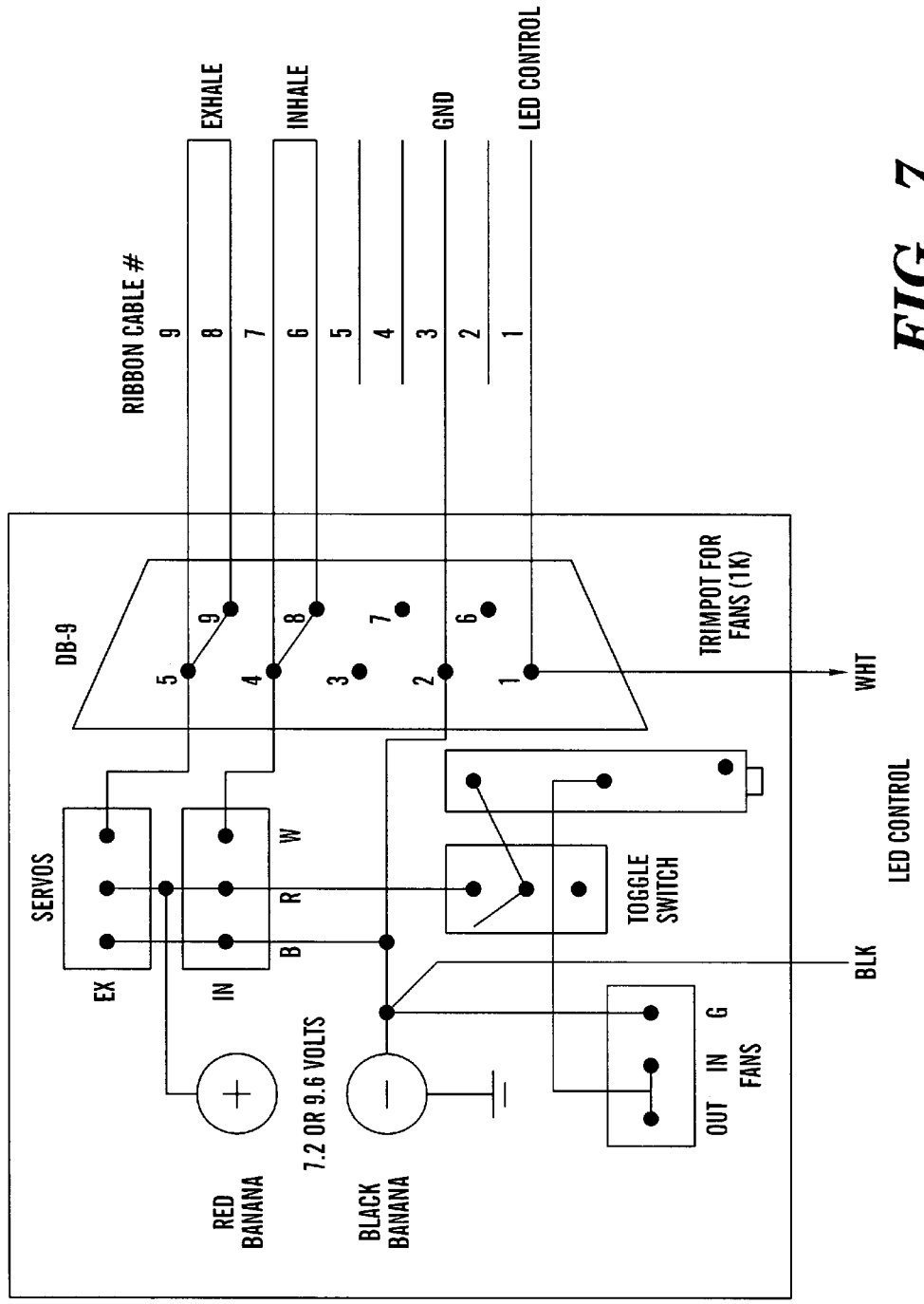
FIG. 7 is a schematic of an electrical control circuit for the sample delivery module of the present invention.

Ambient odors are drawn into the sampling chamber (made in house) in a pulsed fashion by two continuously running fans (for example, Panaflo DC, brushless, 12 V, 270 mA, 19.7 cfm)—one for generating inhalation (see FIG. 6a), one for exhalation (see FIG. 6b) through the sampling chamber. The inhalation or exhalation flows are gated by butterfly valves (made in house), controlled by servo motors (Hobbico, high power, mini servo CS-35 from Tower Hobbies, PO Box 9078, Champaign, Ill. 61824-9078) governed by the computer under software control. During inhalation, flow from the inhalation fan is connected to the sensing chamber (via standard 1" ID PVC plumbing materials) and flow from the exhalation fan is connected to exhaust (see FIG. 6a). During exhalation, flow from the exhalation fan is connected to the sensing chamber and the inhalation fan is connected to exhaust (see FIG. 6b). This control valve arrangement prevents the build up of pressure pulses and keeps flow rates reasonably constant for both in- and ex-halation and for rapid switching between the two. Computer control of the servo motors determines the duration, rise and fall times, and frequency of sniffing. It is important to note that these parameters (along with the others described below) can be changed in real time during data acquisition in order to optimize the signals of interest. FIG. 7 shows the interface board between the servo motors and computer.

D. Sensor Array

1. Sensor Elements

As discussed elsewhere, sensing elements are composed of either dye, dye compounds, or dye-polymer mixtures applied to removable sensor substrates. In one embodiment, thin films of either dye, dye compounds, or dye-polymer mixtures are deposited on a flat plastic or glass substrate. In preferred embodiments, dye, dye compounds, or dye-polymer mixtures are deposited directly onto fibrous supports made from natural or synthetic cellulose, polymers, glasses, ceramics, metallic, or other materials. The use of fibrous dye substrates dramatically increases the magnitude of the response signals, which improves analyte detection and discrimination of the device. In an alternative embodiment, thin dye-polymer films or dye-containing fiber supports can be suspended freely across a perforated removable solid substrate which is placed in the center of the air flow stream, thereby exposing both sides of the sensor to vapor phase analyte.

An innovative feature of the sensing device is the use of interchangeable, removable sensor substrates. Supporting the sensor array on easily removable substrates, facilitates rapid changing of sensing sites during sampling for improving the sensitivity and discrimination for specific analytes in a variety of sampling applications. This feature further provides for rapid screening of dyes, dye compounds, and dye-polymer mixtures for evaluating new sensor materials and analytical detection algorithms.

The size, thickness and surface area of sensor element sites may be modified to optimize sensitivity and discrimination and to efficiently couple sensor elements to light sources and detectors. Generally, a larger sensor geometric area and a close matching of the sensor element geometric area with photodetector area will provide better sensitivity.

2. Array Configuration

The cross-reactive sensor array of the present invention may comprise either analyte-specific or broadly responsive sensor elements. The number of sensor array elements can be configured for specific sampling applications requirements. Specific sensors for defined analytical tasks can be chosen from among the many possible sensing element sites present in the array. Sensor and array configurations may be modified through the addition of additional LED-sensor-photodiode-filter channels depending on the requirements of a particular analyte discrimination task.

In one preferred embodiment, multiple sensor arrays and array substrates may be deployed in the sampling chamber. Such multiple arrays may comprise a series of hierarchically organized sensor arrays such that the first interaction and sampling of the analyte is with a broadly responsive sensor array and, subsequently, the analyte sample is automatically diverted for additional sniffs, on the basis of analytical information fed back from the computer, to specific second order arrays designed to detect and identify the specific type of analyte. Thus, a plurality of sensing arrays may be arranged hierarchically so that ever finer discriminations can take place successively along the pathway. Additionally, the longevity of sensors can be extended by redundant arrays that are protected from exposure until needed; by delivery of analytes as short pulses, and by reducing light exposure by rapidly pulsing LEDs. Low light excitation levels can be used if high sensitivity photodetectors such as avalanche photodiodes are employed. Rapid short pulsing of analytes prevents sensing surfaces from ever reaching equilibrium.

For enhanced, smart mode operation, the number of array sensors used in sampling or detecting an analyte may be modified, in real-time during either actual sampling or post-sampling data analysis using "on-the-fly" intelligent feedback control. By way of example, if a specific sensor is unresponse to a particular analyte sample, the corresponding sensing channel may be automatically removed from consideration by a smart sampling or analysis algorithm provides feedback control to the microcontroller. In addition, the weighting of individual sensors in the analysis and detection algorithm may be adjusted based on the signal contribution of individual sensors. Given that individual sensors have different breadths and peaks of response, sensor weighting will vary for different analytes.

In one preferred embodiment a 32 channel sensor array is employed. It is anticipated that an array of thirty-two sensor elements should have the capability of detecting at least 1000 different analyte types, as long as the sensors materials employed provide sufficient diversity in their analyte detection capability and are appropriately broad in their spectra of response. While the results presented in Examples 1 through 4 were generated for array sizes ranging from nine sensor elements to thirty-two elements, one skilled in the art may increase or decrease both the size of the sensor array and number of sensing channels, following the teachings disclosed herein, for meeting specific sensing application requirements.

E. Optical Detection System

Typically, epi-illuminating optics are employed with conventional optical sensing systems. Epi-illuminating optics require relatively complex dichroic mirror arrangements for each channel where a different excitation and emission wavelength is used. Thus, in the epi-illumination format an excitation filter, a dichroic mirror, and an emission filter are required for each wavelength. The sensing system of the present invention employs a trans-illumination configuration where only excitation and emission filters are needed. Since the epi-illumination mode typically requires critical optical component alignment and is sensitive to vibration and movement, the trans-illumination mode of the present invention is advantageous for robust, compact, portable sensing devices for field sampling of ambient environments.

A schematic diagram of the optical detection system of the present invention is provided in the block diagram of FIG. 3. FIG. 8 provides a cross-sectional view of the sampling chamber that schematically shows the configuration and relative orientation of individual LED-photodiodes-optical filters-sensor pairings within the sampling chamber housing. For simplicity, the cross-sectional view in FIG. 8 shows only three sensing channels, comprising three LED-photodiode-filter-sensor channel pairings. A schematic exploded view of a nine sensor array configuration is shown in the inset of FIG. 8. It is important to note that the partial array configurations shown in FIG. 8 are merely used to demonstrate, by way of example, the relative orientation and positioning of the sensors, filters, photodiodes and LEDs in the sampling chamber and are not intended to indicate any limitation in the size of sensor arrays that may be employed in the present invention. The actual sensing device of the present invention may employ larger or smaller arrays and any number of sensing channels with corresponding LED-photodiode-filter-sensor parings. For example, in one preferred embodiment, 32 LED-photodiode-optical filters-sensor channel parings are employed. The number of sensor array channels may be increased or decreased depending on specific sampling applications and analyte discrimination requirements.

1. Array Components Configuration

Figure 13A:
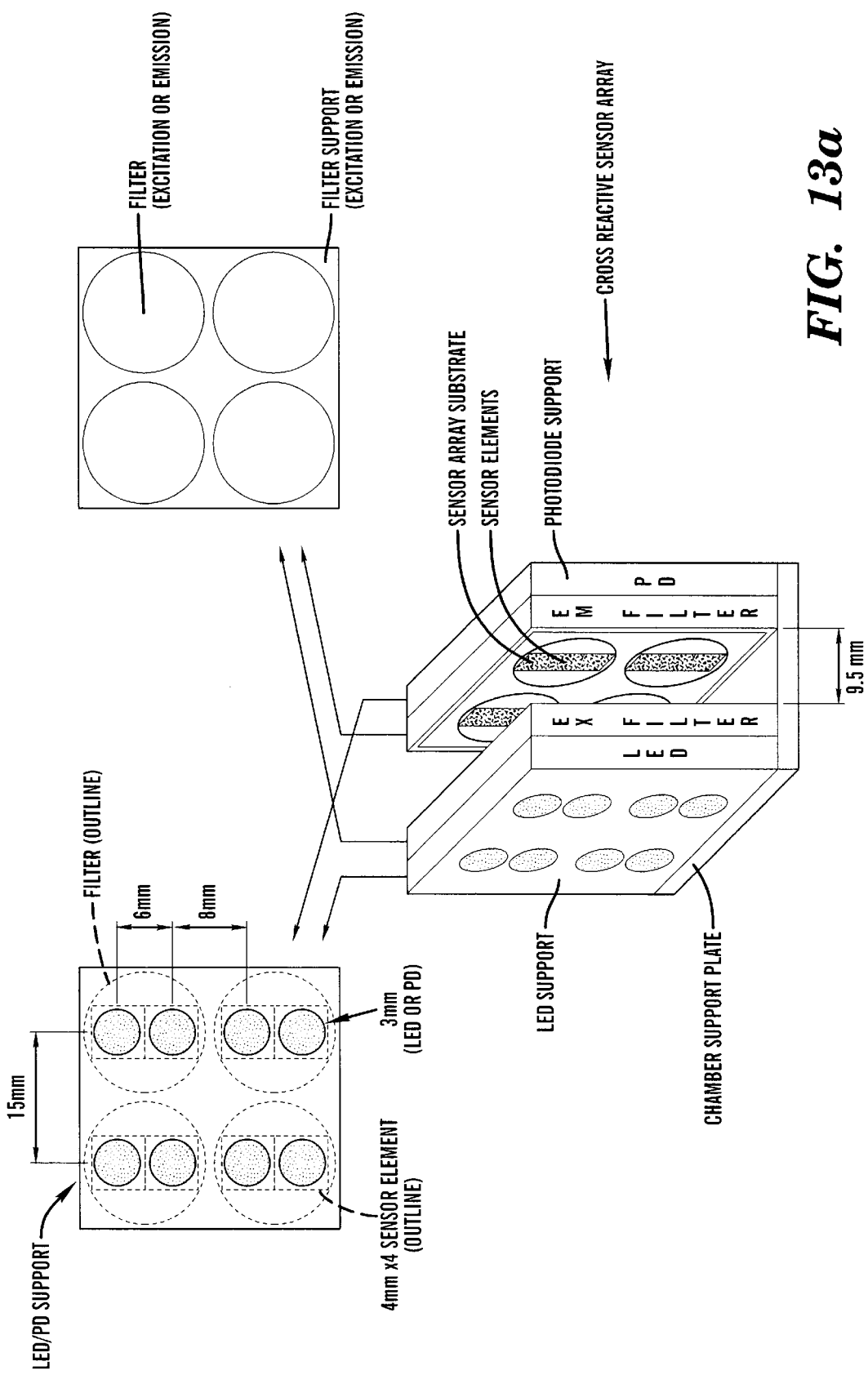
FIGS. 13a–b are schematic diagrams showing a typical sensor array module configuration for the sensor of the present invention.
Figure 13B:
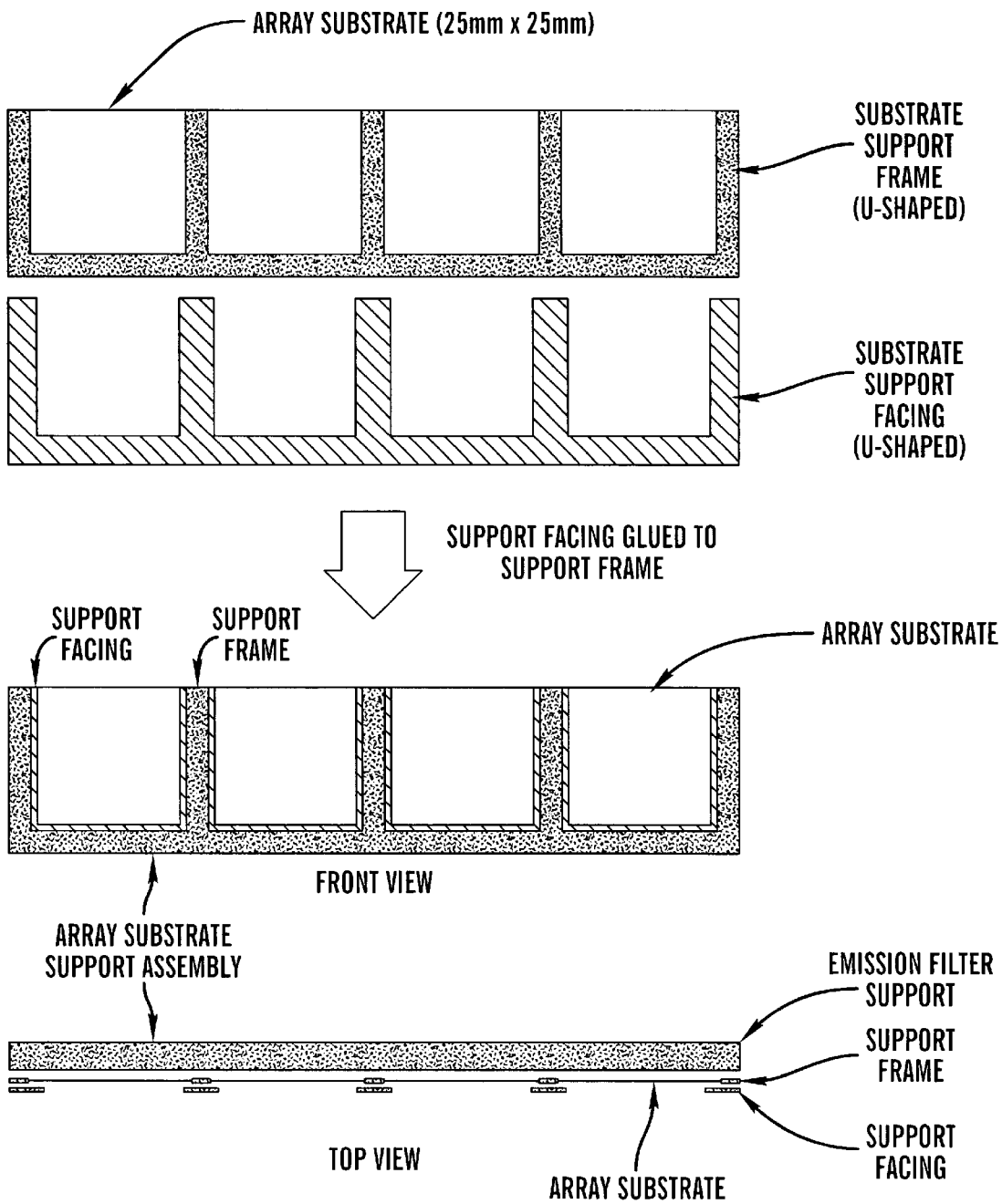

The configuration and relative orientation of LEDs, photodiodes, excitation filters and emission filters, sensors and sensor array substrate is shown schematically in FIGS. 13*a–b*. While an eight sensor-LED-photodiode-filter module is shown in FIG. 13*a* by way of example, larger and smaller modules and arrays may be constructed based on specific sampling and detection needs. For example, in one preferred embodiment, a 32 element sensor array may be assembled from four modules aligned side-by-side with eight sensors in each module. As shown in FIG. 13*a*, a plurality of LEDs are mounted on a nominally 30 mm×30 mm×6 mm black plexiglass support by drilling two columns of four 3 mm holes in a 2×4 array configuration. The LEDs are press fit into the mounting holes and may be readily removed for replacement. A photodiode support with the same dimensions is used for mounting a plurality of eight photodiodes in a 2×4 array configuration. Both the LED and photodiode arrays are mounted in columns with pair row spacings of 6 mm center to center and interpair spacings of 8 mm center to center. Column spacing for both the LED array and photodiode array is 15 mm center to center.

As shown in FIG. 13a, 12.5 mm (½") diameter excitation filters are mounted on an approximately 30 mm×30 mm×6 mm excitation filter support formed by drilling four ½" holes in a black plexiglass support plate to accommodate the filters in a 2×2 array configuration. Other filter assembly configurations, containing a larger or smaller filter array with larger or smaller filters may be employed in other embodiments. A similar emission filter support with the same dimensions as the excitation filter support is fabricated for mounting four emission filters. The emission filters and excitation filters are mounted to their respective supports with conventional set screws. The resulting excitation filter support assembly is attached directly to the front face of the LED support assembly and the emission filter support assembly is attached directly to the front face of the photodiode support assembly with conventional mounting screws.

A plurality of sensor elements are applied either directly to a transparent sensor array substrate, for example a glass coverslip, as coatings or droplets. Alternatively, where porous or fibrous sensing elements are employed, these may be taped, glued, or clamped to a transparent sensor array substrate, or suspended over openings or perforations in an array support substrate which may be either transparent or opaque. As shown schematically in FIG. 13b, removable, interchangeable sensor array substrates, or array support substrates, are mounted flush with the front face of the emission filter support using an substrate support holder. The substrate support holder is formed by gluing a U-shaped substrate support frame and a U-shaped substrate support facing to the front fact of the emission filter support. The sensor array substrates, or array support substrates, are slidably mounted in a slot or channel formed by the substrate support frame, support facing and front face of the filter support as shown in FIG. 13b. The substrate support assembly provides for rapid removal and replacement of the interchangeable array substrates or array support substrates.

The sensor array may comprise either a single sensor array module, as shown in FIG. 13a, or a plurality of sensor modules aligned edge-to-edge to form a multi-module array containing a large number of sensor elements. The bottom edge of both the LED-excitation filter module support assembly and the photodiode-emission filter-sensor module support assembly are secured to a chamber support plate with conventional mounting screws. In this configuration, the excitation filter side of the LED assembly faces the sensor array side of the photodiode assembly. The LED and photodiode modules, or plurality of modules, are preferably aligned parallel to one another with spacing between the two modules adjusted to optimize illumination of the sensor array elements by the LED array. In one preferred embodiment shown in FIG. 13a, this spacing is approximately 9.5 mm. In one preferred embodiment, a 32 sensor array is formed by mounting four eight sensor modules ton the chamber support plate. Other configurations using larger or smaller sensor modules and a fewer or greater number of modules may be employed to accommodate smaller or larger arrays by adjusting the size of the LED, photodiode, filter and sensor supports and chamber support plate and adjusting the spacing between opposing LED and photodiode modules to optimize illumination of sensor array elements by the LED array.

2. Excitation/Emission Filters

Commercially available, optical bandpass excitation filters for LED light sources and emission filters for photodiode detectors were obtained from Andover Corp. (Salem, NH). While these filters are available in ¼ to 1½ inch sizes, ½ inch filters were used in preferred embodiment. By way of example, FIG. 13 shows schematically the relative orientation, configuration and spacing of excitation and emission filters for an embodiment which employs 32 sensors and sensing channels. For simplicity, FIG. 13 shows only one of four eight-sensor modules employed in a 32 channel sensor array. In this embodiment, with four sensor modules, 16 Excitation filters are arranged in a 2×8 array with a center to center distance of 15 mm. With this embodiment, each emission filter covers a pair of two adjacent photodiodes having a 6 mm center to center spacing. In this particular embodiment, the 32 sensor elements in the array were aligned with the center of the LED-photodiode pair sight line. Other embodiments are envisioned where each sensor channel has its own individual excitation and emission filter or where more than two sensor channels share each excitation and emission filter.

The excitation and emission filters that were utilized for specific sensor materials in one preferred embodiment are listed below. Note that the filters are designated by center wavelength, followed by "FS", then the bandpass at 50% amplitude.

1. Nile Red:
excitation - 533FS40
emission - 600FS10, 610FS10, 620FS10, 633FS10, 640FS10, 650FS10, 660FS10
2. Nile Red + Poly(N-vinylpyrrolidone):
excitation - 533FS40
emission - 600FS10
3. Nile Red + Poly(ethyl cellulose):
excitation - 533FS40
emission - 610FS10
4. Nile Red + Poly(dimethyl siloxane):
excitation - 533FS10
emission - 633FS10
5. Nile Red on Millipore glass filter:
excitation - 533FS40
emission - 650FS10
6. Pentiptycene-derived phenylenecthynylene polymer 1:
excitation - 460FS10 // 430FS10
emission - 488FS10, 500FS10 // 470FS10, 510FS10
7. 4-(dicyanovinyl)julolidine (DCVJ):
excitation - 460FS10 // 430FS10
emission - 488FS10, 500FS10 // 470FS10, 510FS10

3. Excitation Light Sources/LEDs

Illumination of sensor elements with excitation light energy may be accomplished with any appropriate light source. Thus, filtered light emitting diodes (LEDs), solid state lasers, or incandescent light sources of the appropriate wavelengths for the dye indicators being used may be employed. In a preferred embodiment, each LED light is passed through an excitation filter matched to a specific sensor element dye excitation wavelength. Where excitation filters are employed, broad band ("white") LEDs with appropriate wavelength filters may be used.

Unlike conventional sensors, by providing individually filtered sensing channels, the present invention enables simultaneous sampling at multiple excitation wavelengths and multiple emission wavelengths with different sensor elements. The present invention uniquely provides for individual control over the amplitude, duration, and duty cycle of illumination for each sensing channel in the array. Control over noise is exerted by feedback. Control over response to ambient light and optimization of signal detection, including reduction of dye bleaching, is accomplished by switching and modulating LED output and coordinate amplifier detection at various frequencies, ranging from kilohertz to megahertz. Control over ambient light interference may be achieved by phase locked LED flashing and photodiode detection.

In the present invention, sensor elements are illuminated directly by focussed, light emitting diodes (LEDs) of the correct wavelength for each sensor dye material. Other advantages achieved from using LED excitation light sources are low power requirements, cooler operating temperatures, and high light output over small area. Additionally, by employing LED light sources for each array sensing channel, each LED channel can be rapidly and independently switched electrically without use of a mechanical shutter. The LED channels can be individually modulated electrically at high rates by feedback from the microcontroller. In addition, the LED channels can be individually filtered for presenting different excitation wavelengths in parallel, thereby avoiding serially and mechanically switching filters during array measurements.

For delivering green light with a peak at 530 nm, E903 Megabrite LEDs (Gilway Technical Lamp, Woburn, Mass.) run at maximum current are used. With this LED model, excitation of the dye Nile Red has been achieved both without excitation filters, using the raw LED output and with excitation filters with peaks at 532 nm–+10 nm. For blue light with a peak at 430 nm, cat. #25-346 blue LEDs manufactured by Everlight (Hosfelt Electronics, Inc., Steubenville, Ohio) run at maximum current are used. Excitation of fluorescent detector materials in the blue have used filters from Andover with a peak at 430 nm+–10 nm.

The LED's are turned on and off under computer control. Since these devices can respond at high speeds, up to megahertz frequencies, they are typically flashed at kilohertz frequencies in order to reduce bleaching. Such switching speeds cannot be achieved using mechanical shutters. The rapid switching capacities of LED's are utilized to flash them on and off in order to reduce sensor bleaching during data acquisition. This is achieved by pre-bleaching sensors before sample sniffs and by reducing total light exposure by shortened duty cycle during sample sniffs. This is accomplished by rapidly flickering the LED so that light is only on during the time when data are being taken and then turned off between data points and between trials.

Figure 5:
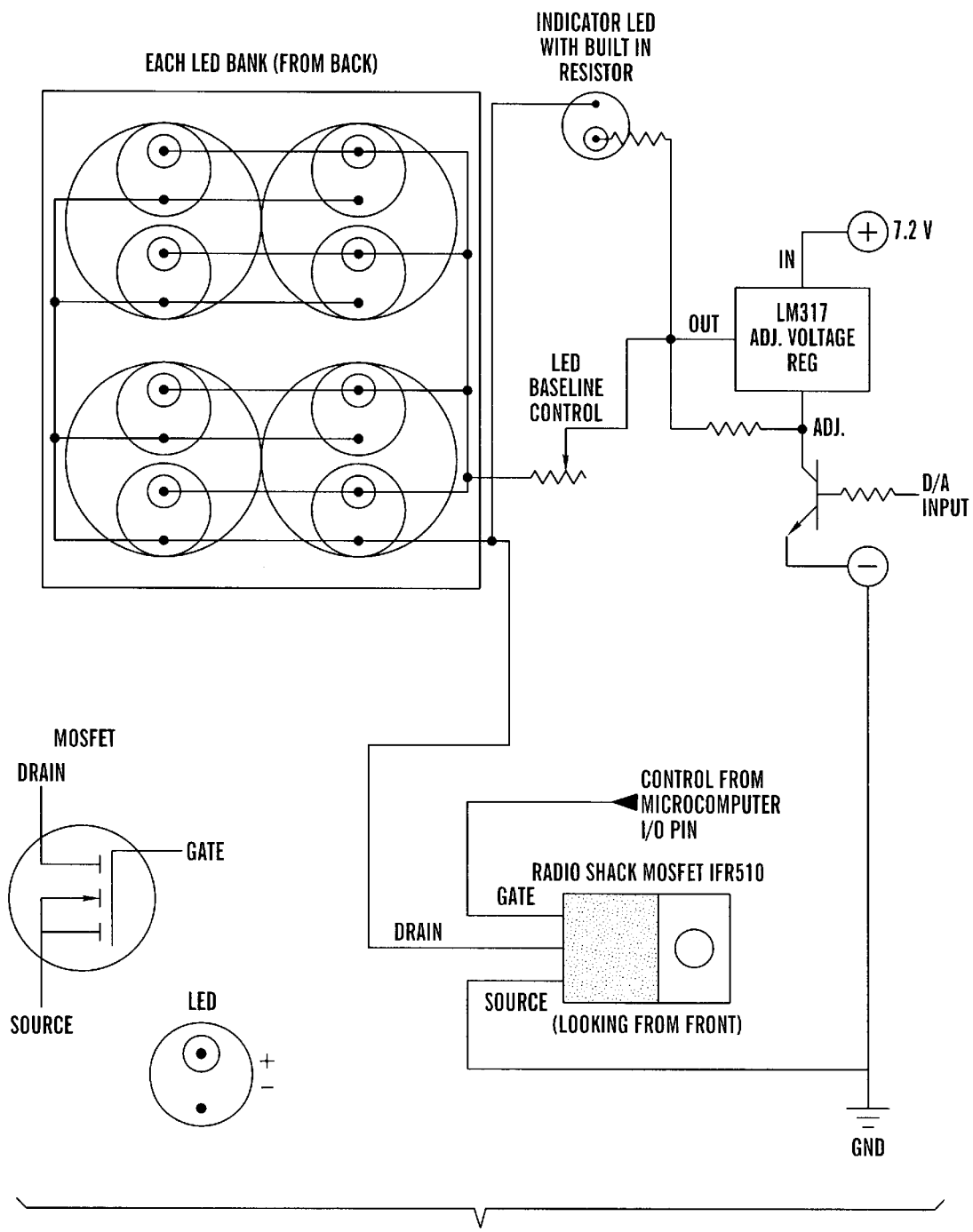
FIG. 5 is a schematic of an electrical circuit of the light generation module of the present invention.

The electrical circuit controlling the LED's, which are connected in parallel, is shown in FIG. 5. In this circuit a Radio Shack power IFR510 MOSFET (Tandy Corp., Fort Worth, Tex.) is controlled by one of the input/output lines (see pin 35 of connector J2 from the computer in FIG. 12) under software control.

4. Detectors/Photodiodes

While a variety of photodetectors such as photomultiplier tubes (PMTs), charge-coupled display device (CCD) detectors, photovoltaic devices, phototransistors, and photodiodes may be used for detecting sensor response signals, in a preferred embodiment, filtered photodiode detectors are employed. In another preferred embodiment, highly sensitive avalanche photodiodes may be employed. Photodiode detectors have distinct advantages compared to conventional CCD camera detectors since they enable independent control and modulation of individual channel optical filtering, current/voltage conversion, signal amplification, and temporal filtering. Other specific advantages are low power consumption, relatively simple electronic circuitry, high sensitivity, configurability, multiple array formats (e.g. circular, square, or linear arrays), fast high frequency response at megaHertz frequencies, low noise, wide dynamic range, and use with low frequency circuits.

In the sensing device of the present invention, an array of filtered photodiodes is employed where each filtered photodiode is either aligned with one filtered LED or, alternatively, groups of filtered photodiodes may be illuminated by a single filtered LED. The individual photodiodes are each aligned with an individual sensor element site with an optical emission filter that is appropriate for the specific dye employed by the individual sensor. Different emission filters may be used for each photodiode or, alternatively, one emission filter may be shared by multiple photodiodes. Photodiode signal noise is controlled by feedback. Additionally, feedback control is exerted over the signal sampling duration and time course. Differential signal inputs may be employed with a separate control sensor and individual sampling sensors. In one preferred embodiment, highly sensitive avalanche photodiodes may be used to permit lower required LED intensity for sensor of excitation and for reducing detector noise.

In one embodiment commercially available EG&G VTP 1232 photodiodes (EG&G, Inc, Gaithersburg, Md.) and commercial 12.5 mm emission filters (Andover Corp., Salem, N.H.) were used. Specific emission filters used in conjunction with the photodiode detectors are discussed above.

While sensors may share the same LED, photodiode and excitation/emission filters, in alternative embodiments, separate LED, photodiode, sensor, and excitation/emission filters may be employed for each of sensor element and sensing channel. In one embodiment, Individual sensor elements and sensing channels may employ different sensing materials, different excitation wavelengths, and/or different emission wavelengths simultaneously. While the results provided in Examples 1 through 4 were generated for array sizes ranging from nine sensor elements to thirty-two elements, one skilled in the art may increase or decrease both the size of the sensor array and number of sensing channels, following the teachings disclosed herein.

The changes in fluorescence as a result of the odor interacting with the sensing material is detected by a photodiode and current to voltage (I/V) converter (FIG. 9) originally designed by Warner Instruments (Hamden, Conn.) and now commercially available from Red Shirt Imaging Inc. (Fairfield, Conn.). There is one I/V converter (FIG. 9) and amplifier/filter (FIG. 10) for each detector channel. The unique feature of this converter/amplifier configuration is that when the LEDs are activated prior to sample delivery, the background fluorescence signal produced by the sensor elements may be offset by resetting the amplifiers to a baseline value so that a full range of high gain amplification may be used to observe small changes in the signals generated by analytes during sampling. In addition, the innovative amplifier board has the option for software control to be exerted over the gain and the filter time constants for all the channels (see connector J2 in FIG. 12). Thus, in addition to being able to manipulate the onset and duration of the illumination and of the sniff as described above, the time constants and gain of the amplifiers can also be controlled in real time during data acquisition. These hardware features offer distinct advantages for optimizing the response of the sensing device for detection, discrimination and identification of analytes or odors of interest.

F. Electronics—Analytical and Control Circuitry

1. Analytical Circuits

Generally, the sensing system of the present invention analyzes spatial-temporal patterns of data output (see FIG. 20) from sensor arrays in order to characterize and identify the delivered sample or its analyte components. Useable information from the sensing array is generated from the pattern of sensor response activity generated by all sensor elements over time and is evaluated using statistical measures such as information theory. Pattern recognition algorithms including template comparison, neural networks, principal components analysis, etc. may be implemented either in conventional digital CPUs, in neuronal network simulator chips, or in analogue neuronal network computers. Additionally, algorithms based on biologically based neuronal connections from the olfactory system and other neuronal circuits in the brain may be employed. The innovative analytical circuits of the present sensing device provide the requisite hardware support for the detection, discrimination and identification capability of the sensing system.

In one preferred embodiment The circuits comprise current to voltage converters for each photodiode (FIG. 9) and photodiode amplification (FIG. 10) with variable gain controlled both manually and by feedback from the computer (FIG. 12). Amplifiers are reset after LEDs are switched on to start the data conversion process at zero volts, as set by a voltage divider on the amplifier output. This permits both positive and negative differences in fluorescence to be recorded. Time constants of each amplifier channel are controlled both manually and by feedback from the computer (FIG. 12). 12 bit, or alternatively, 16 or 24 bit, analogue to digital (A/D) conversion of signals from each sensing photodiode is provided. Multiplexing of multiple sensing channels is provided via the microcontroller computer (FIG. 12).

Figure 9:
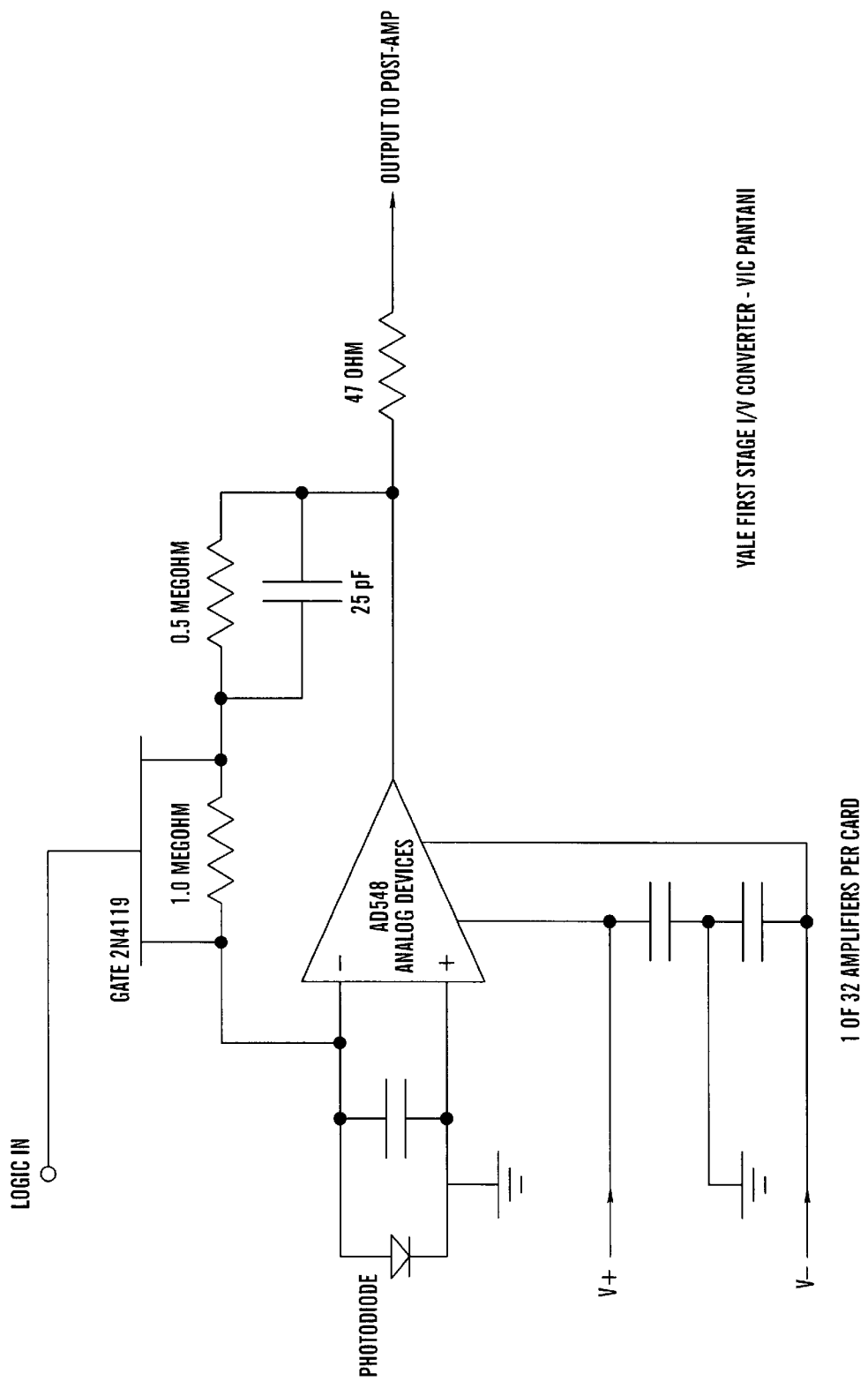
FIG. 9 is a schematic of an electrical circuit of the preamplifier module of the present invention.

FIG. 9 shows a standard current to voltage (I/V) converter using an Analog Devices AD548 operational amplifier with a choice of feedback resistors of 1 or 0.5 megohms controlled by a software switched gate (2N4119) to control the frequency response and noise properties of the I/V board. This circuit converts current changes in the photodiodes resulting from different levels of light exposure to voltage changes that are fed to the amplifier circuit shown in FIG. 10.

Figure 10:
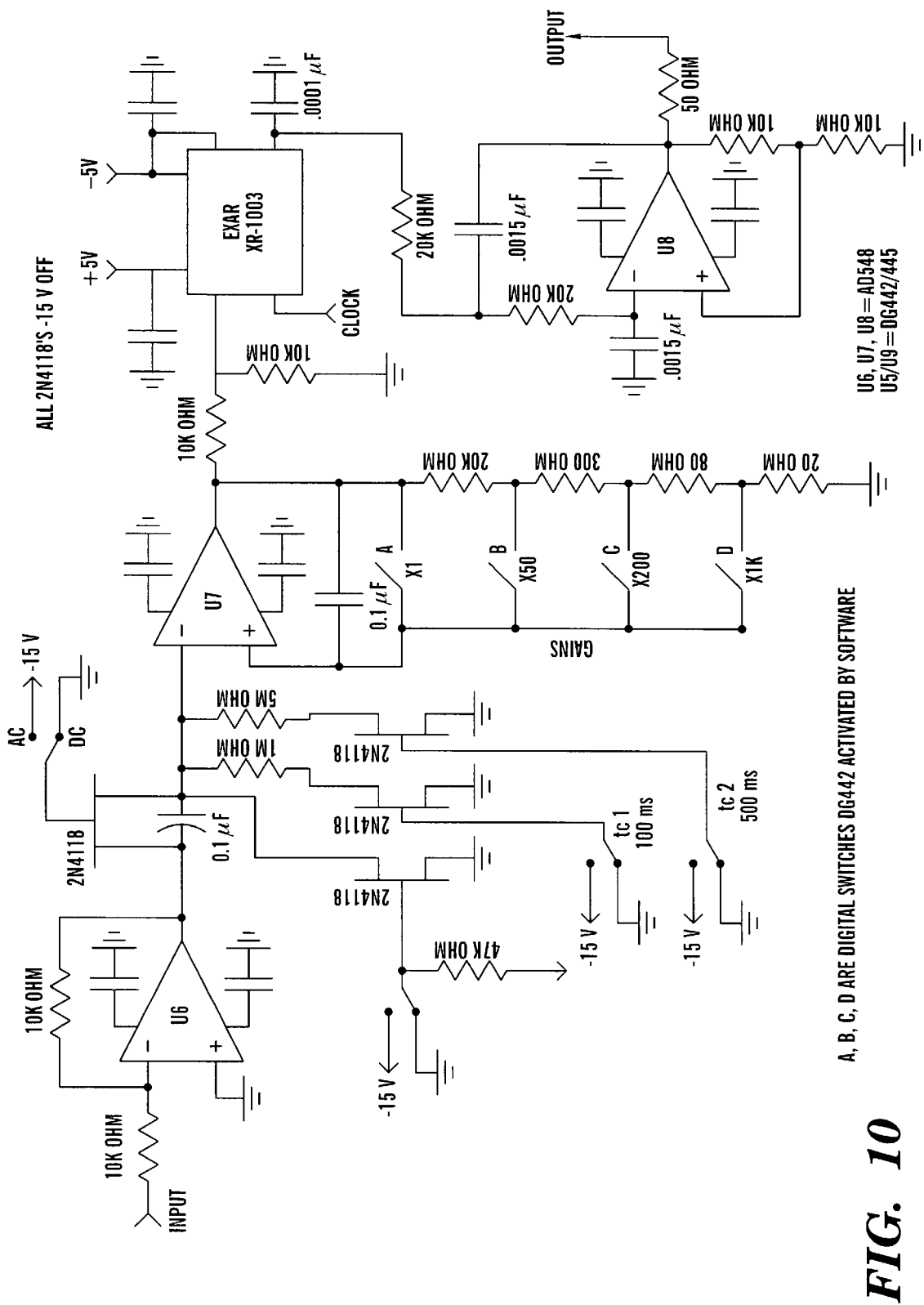
FIG. 10 is a schematic of an electrical circuit of the amplifier module of the present invention.

The standard amplifier circuit in FIG. 10 consists of operational amplifier transistors (AD548) in circuits which provide 1) a choice of time constants (DC, 500 ms, 100 ms); 2) resetable baseline; 3) and a choice of gains (1×, 50×, 200×, 1 k×). All of these attributes are under software control via input/output (I/O) control lines from the computer via the 2N4118 gates. The filter section of the amplifier is run by a clock line from an oscillator on the computer control and amplifier control board shown in FIG. 12.

FIG. 5 shows the circuits to control illumination of the LEDs. The gate of the MOSFET, IFR510, is controlled by one of the computer I/O lines under software to turn the LEDs on and off at the time designated by the program. The LM317 is an adjustable voltage regulator that determines the voltage delivered to the LED bank and therefore determines the intensity of the LEDs. The LM317 is controlled by an output digital to analogue line from the computer under software control.

Figure 11:
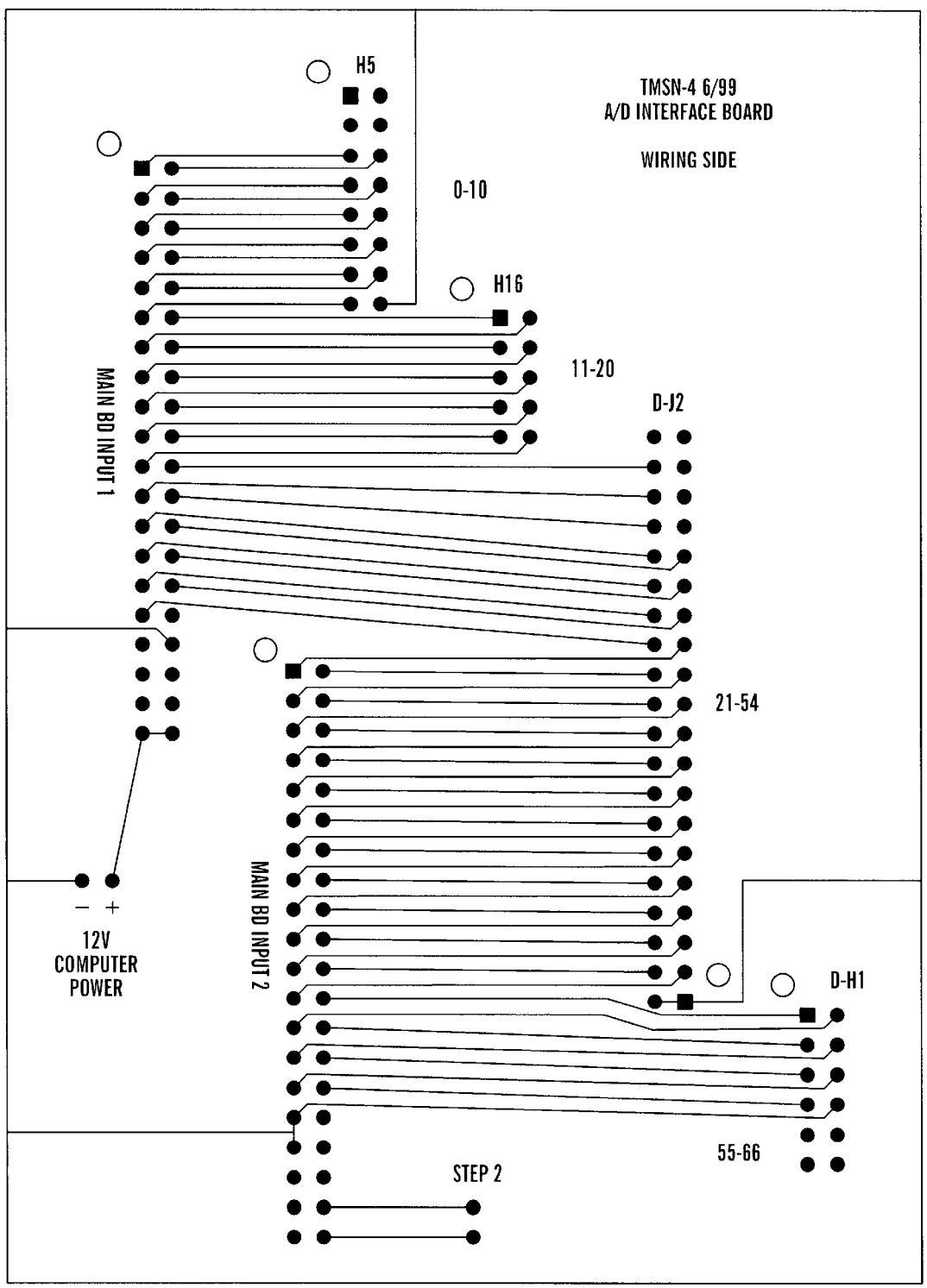
FIG. 11 is a schematic of the electrical circuit connecting the channel output lines from the amplifier and input lines of the A/D converter in the microcontroller computer.
Figure 12A:
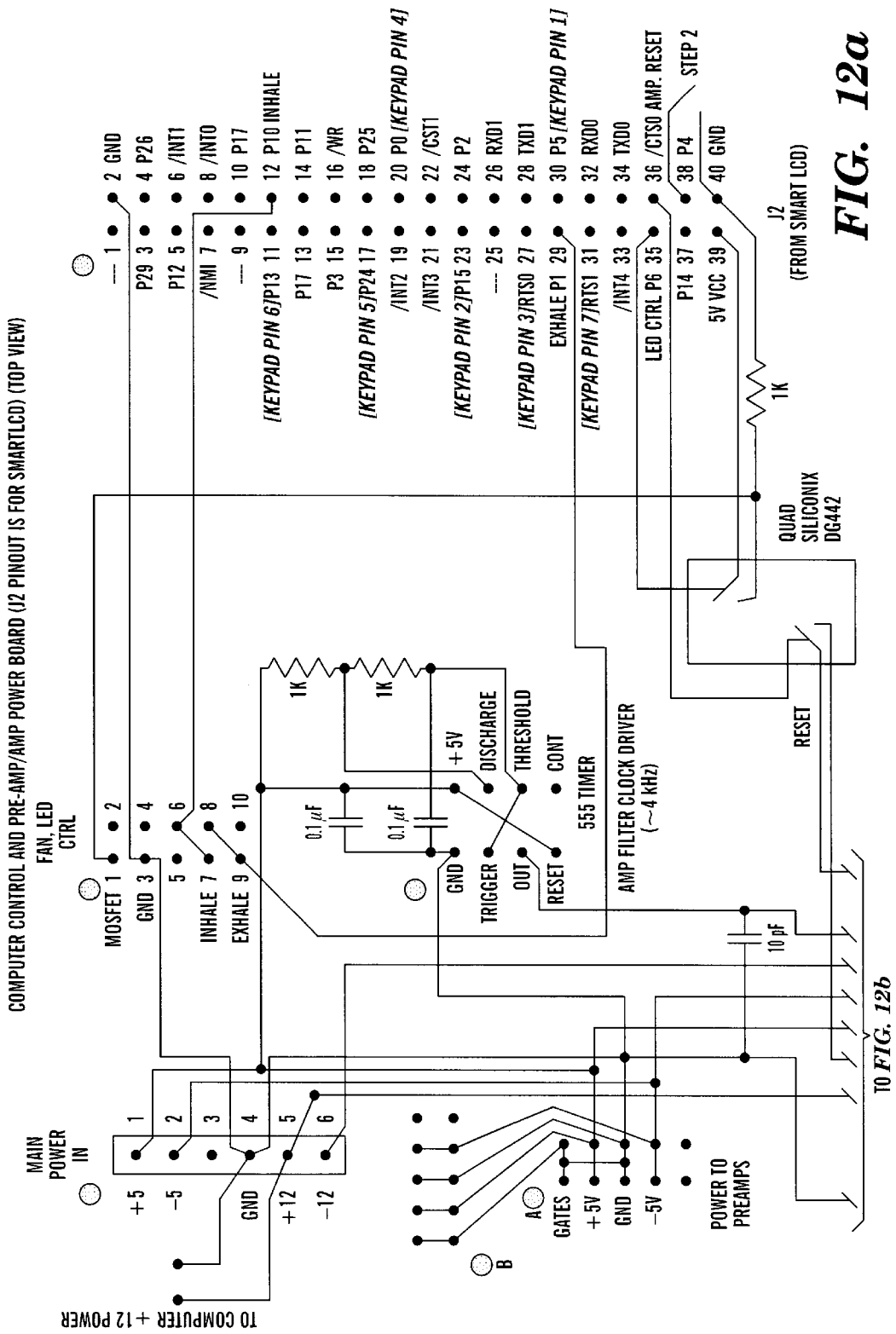
FIGS. 12A and 12B show a schematic of an electrical circuit for the micro-computer control module of the present invention.
Figure 12B:
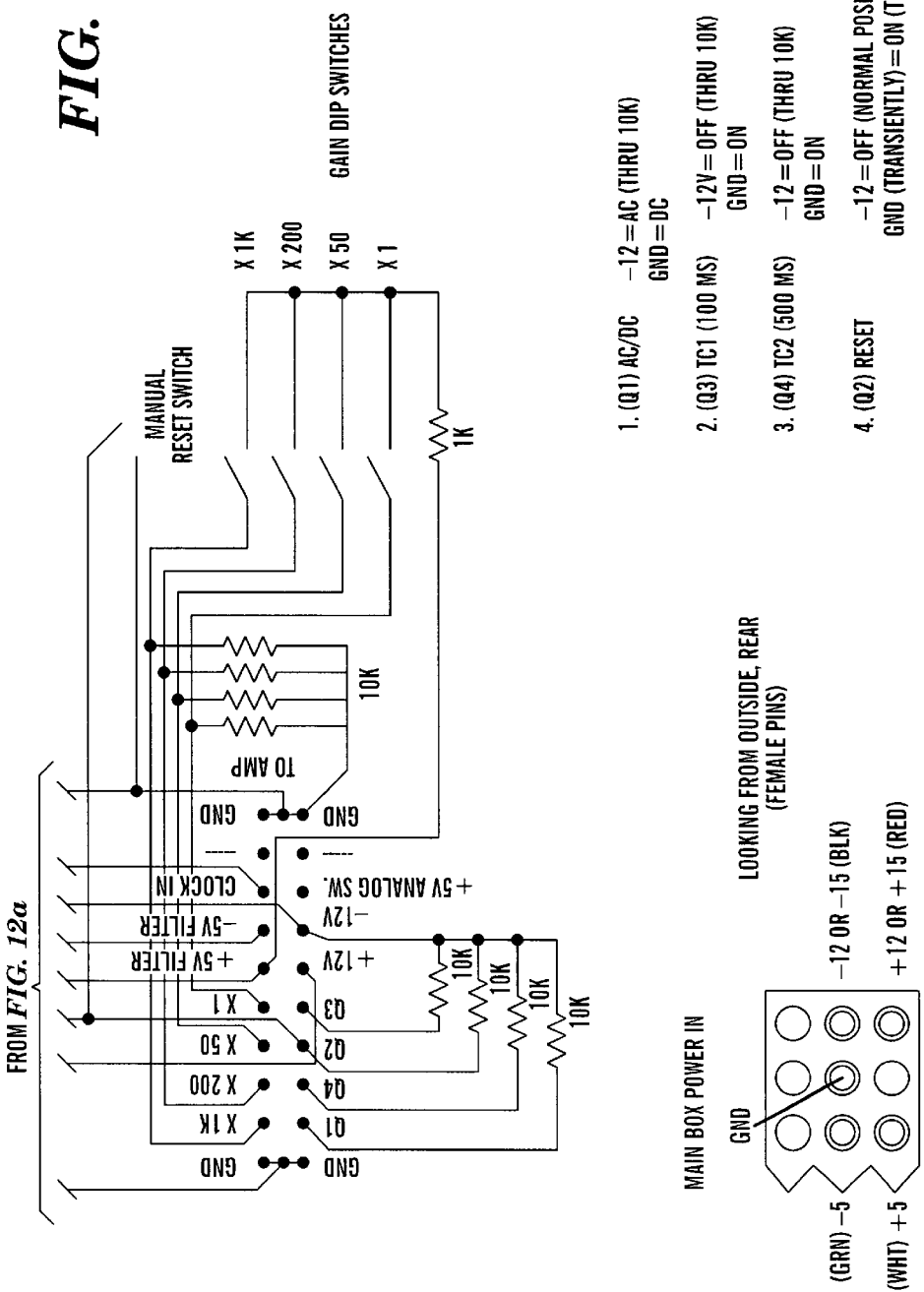

FIG. 11 shows how the output lines from the amplifier channels are connected to the appropriate input lines of the analogue to digital converters in the microcontroller computer. There are no active electronic components here, only wired connections.

FIG. 12 shows how the I/O lines from connector J2 of the SmartLCD computer control the various function of the device and how power is provided to the preamplifier and amplifier boards. Regulated + and −12 v. and regulated + and −5 v come in through the main power connector in the upper left of the Fig. These voltages are distributed appropriately to the power connectors for the preamp and amplifier boards. The J2 connector provides I/O line control for the MOSFET that controls the LEDs (as described for FIG. 5) through the 'LED/fan' control connector. The inhale and exhale valves are also controlled by I/O lines going to this connector. The remaining I/O lines from J2 control the gates (as described for FIG. 10) that control the time constants, the reset, and the gains on the amplifier board. The 555 timer generates the appropriate clock signal (~4 kHz) for the filters on the amplifier board. The Siliconix DG442 is simply an intermediate software controlled switch that interfaces the I/O lines with the reset line on the amplifier board.

FIG. 12 shows the interface circuit that allows the mircocontroller computer to control the LED's, the fan valves (inhalation and exhalation), the amplifier reset, and the amplifier gain and time constants from connector J2. As shown in FIG. 4, in one embodiment, 32 channels are digitized to 12 bits after going through a voltage divider such that, after the light is turned on and the amplifiers reset, fluorescence differences in both positive and negative directions can be detected. The number of sensing channels may be increased or decreased by replicating or removing the individual channel circuits shown schematically in FIGS. 4, 5, 9, 10, 11 and 12.

The device is controlled by a TERN Smart LCD microcontroller (Tern, Inc., Davis Calif.) computer running at 40 MHz with 512 K RAM, 66 channels of 12 bit A/D, and programmed in 'C' programming language. In alternative embodiments, a faster computer may be employed (e.g. PIII-730 with 1 GB RAM) to yield shorter detection times.

All electronic parts and circuit components are conventionally known and readily available at standard electronic suppliers such as Radio Shack or DigiKey. The I/V (FIG. 9) and amplifier boards (FIG. 10) were designed and built by Warner Instruments (Hamden, Conn.) but are made from conventional, commercially available components from electronic suppliers.

For the standard electronic parts employed in the described embodiments there are many interchangeable substitutes which are known and used in the electronics art. One skilled in the art could substitute many equivalent programmable microcomputer controllers as long as they provide a minimum of at least 12 bit or greater analogue to digital converters, an easy input device (e.g. keypad) and a simple output device (e.g. LCD display).

III. Sensing Method

A. Overview

An innovative feature of the present invention is the use of temporal control over stimulus presentation and the examination of the resulting changes in sensor output over time. Unlike conventional designs, with the present invention analyte presentation to the sensing sites is carried out by negative pressure 'sniffing', rather than by conventional positive pressure pulsing which requires samples to be enclosed in confined containers. An additional innovative feature of the present invention is that sniffing parameters can be electronically modulated by feedback from via computer control and flow rate, sniff duration, and temporal profile can be adjusted and modulated for specific sampling environments and target analytes to detect ambient odors drawn into the sensing chamber. Sampling modulations can be carried out in real time so that subsequent sniffs can be modified by the preceding ones. With the smart sampling mode capability of the present invention, a computer turns the sniff on and off and can modulate and control sniff parameters during a sampling.

B. Training Runs

Figure 15:
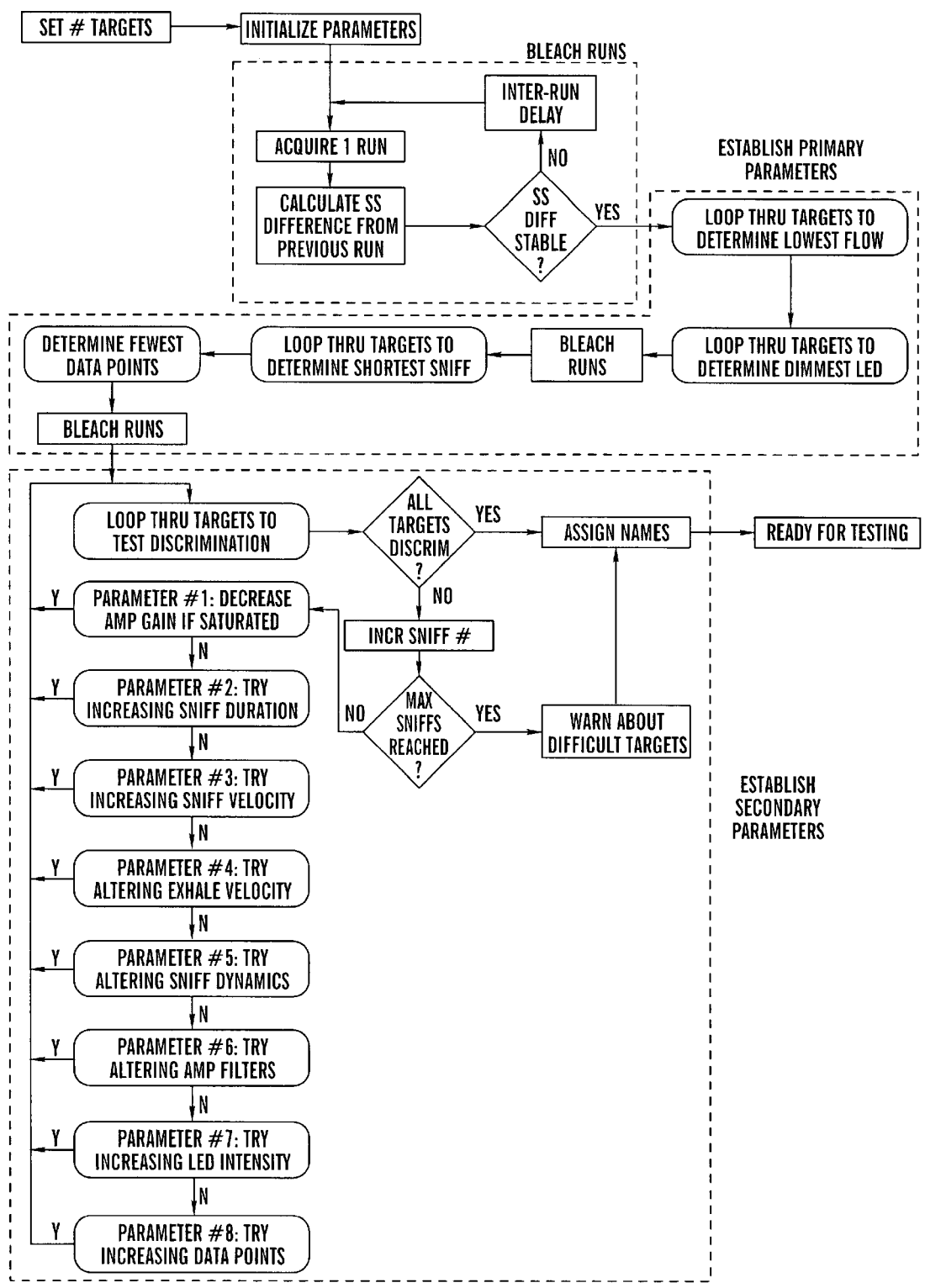
FIG. 15 is a schematic flowchart of a sensor training method employed in the sensing method of the present invention.
Figure 21:
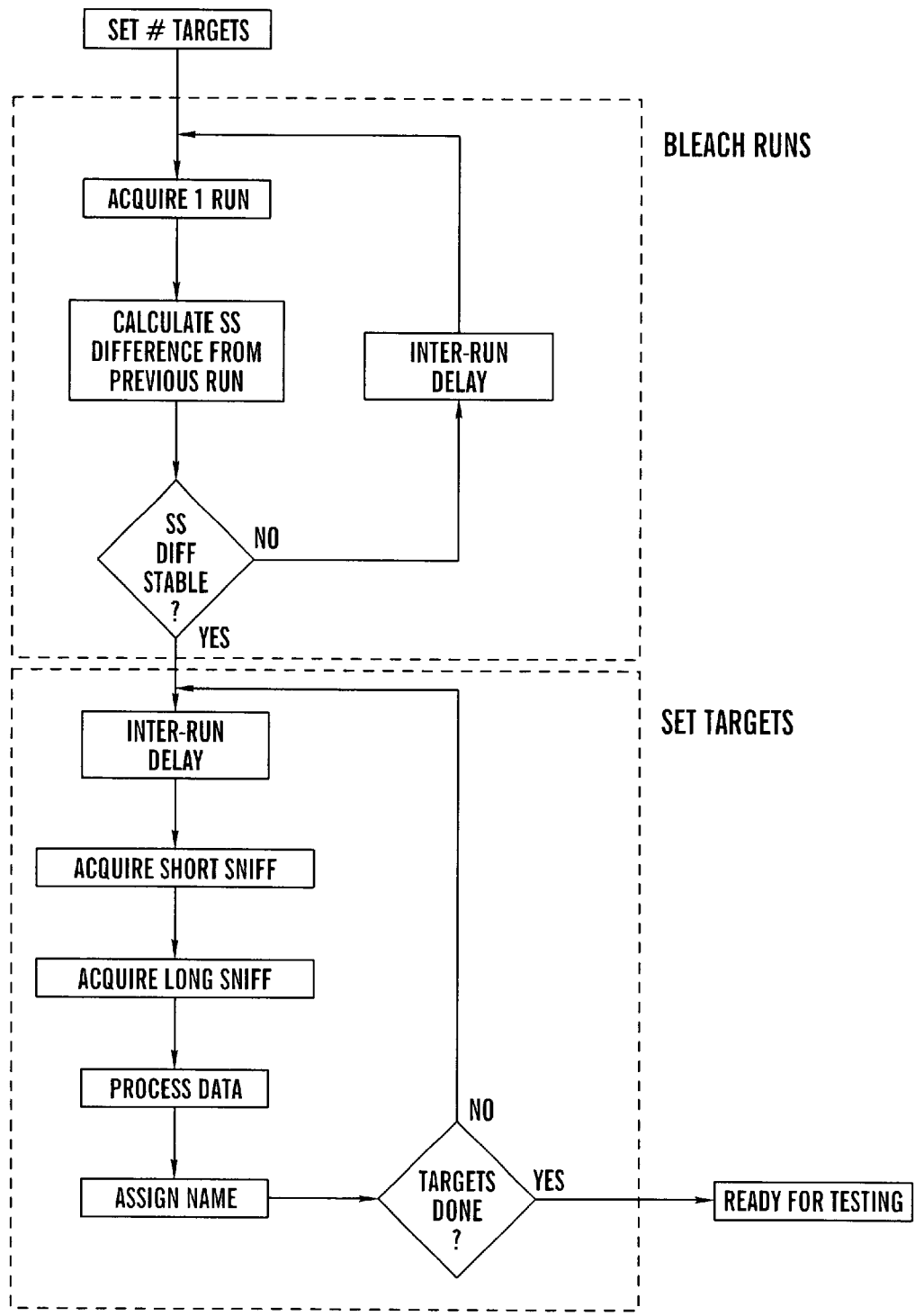
FIG. 21 is a schematic flowchart of the sensor training method employed in the smart sensing method of Example 3.

FIGS. 15 and 21 provide schematic flowcharts of typical training methods employed with the sensing device of the present invention. Further details of smart mode training are discussed in later sections and details of one training embodiment are described in Example 3.

Target samples of known analytes (odors), either pure compounds or complex mixtures, are required for training the sensing device and identifying unknown analytes in sampled fluids. Training samples are typically provided in small, disposable, plastic screw top jars which are vapor tight. A small paper cup insert may be employed with the sample jars as a disposable liner to facilitate cleaning. For typical target training samples, two cotton balls are placed in paper cup that is positioned inside the sample jar and analyte odor-generating material is typically added either as a liquid or solid (e.g. camphor, chocolate, cloves, and orange peels). The cotton provides a high surface area for promoting evaporation and prevents unrestrained liquid samples from spilling.

For all training runs, initially a clean air test sniff is first taken by initiating the automated sampling sequence which provides for turning on the LEDs, taking digitized data from the photodiodes, measuring background fluorescence and storing this in memory, turning on the sniff pump, turning off the pump, terminating data acquisition, and turning off the LEDs. The device is then trained for target analytes by placing the target analyte sample container into position and initiating the automated sampling sequence. The sequence of sampling and data acquisition events for target analytes is the same as for the air baseline sample. This training sequence is repeated for each target analyte of interest and response data are stored in the microcontroller computer RAM memory module.

C. Sampling Runs

Figure 16:
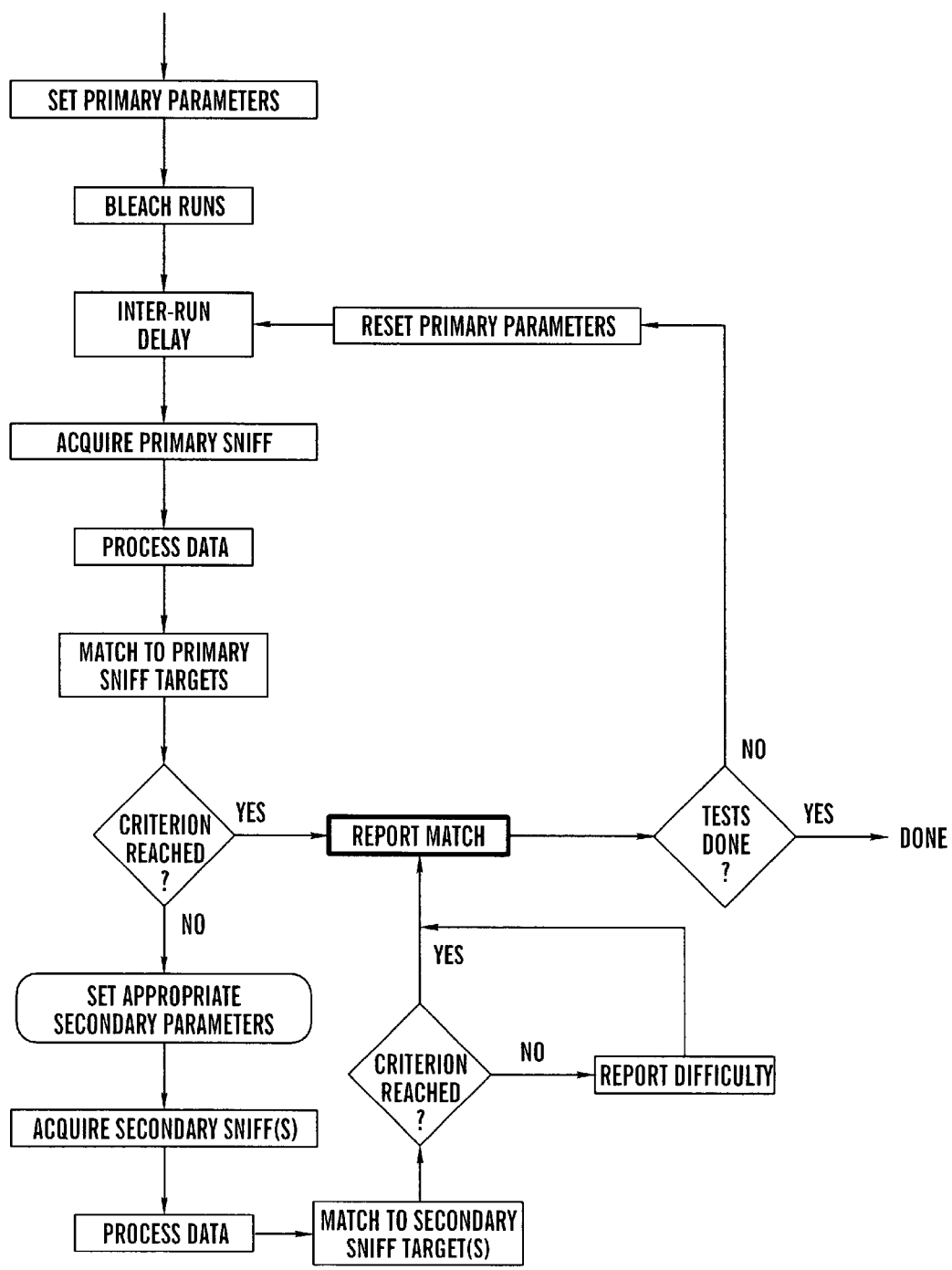
FIG. 16 is a schematic flowchart of an analyte test method employed in the sensing method of the present invention.
Figure 17A:
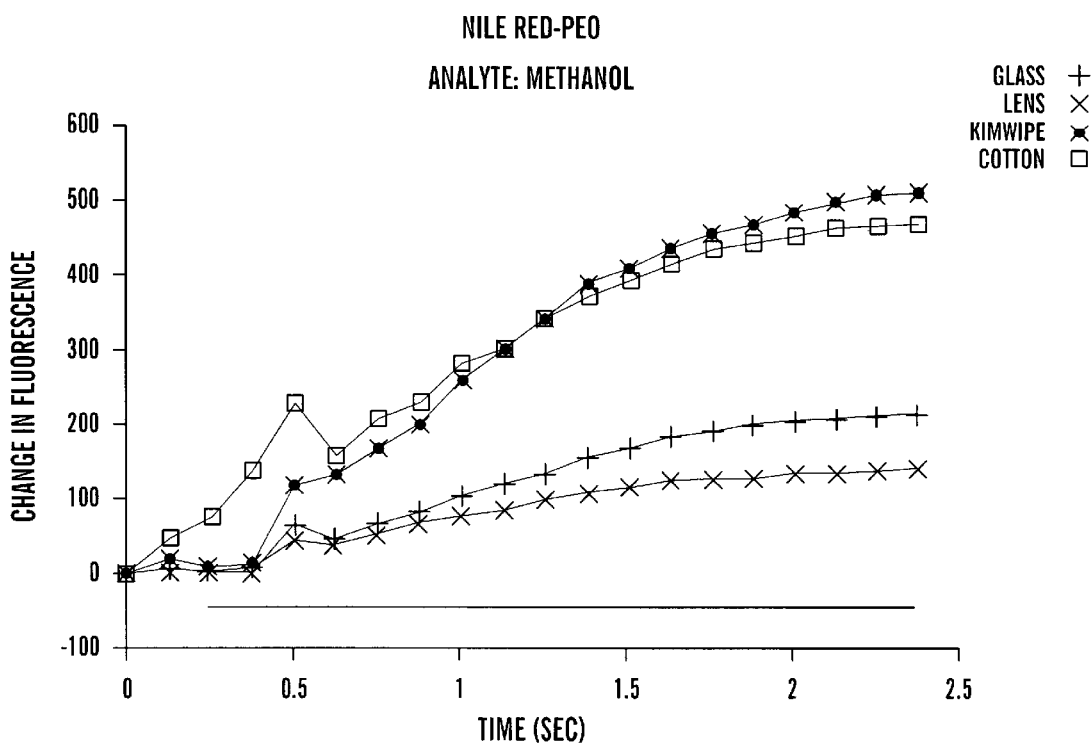
FIGS. 17a–d show comparative changes in fluorescent sensor response to methanol, amyl acetate, acetone and dinitrobenzene analytes with conventional glass sensor substrates and innovative sensor substrates of the present invention.
Figure 17B:
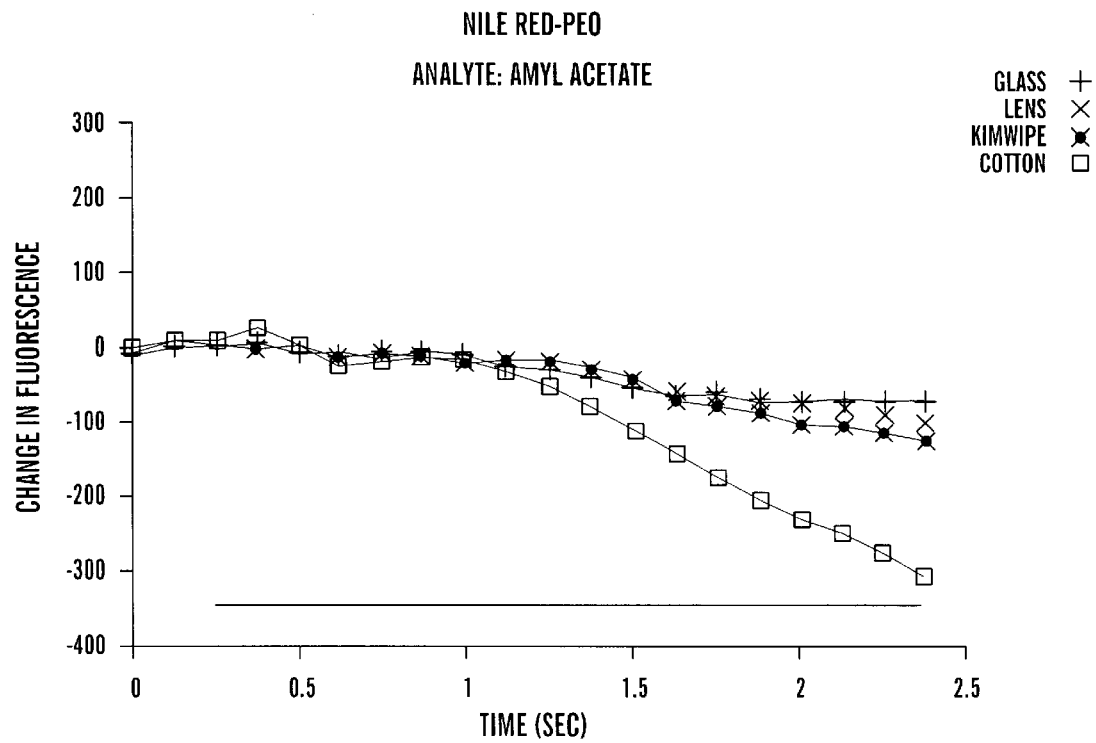
Figure 17C:
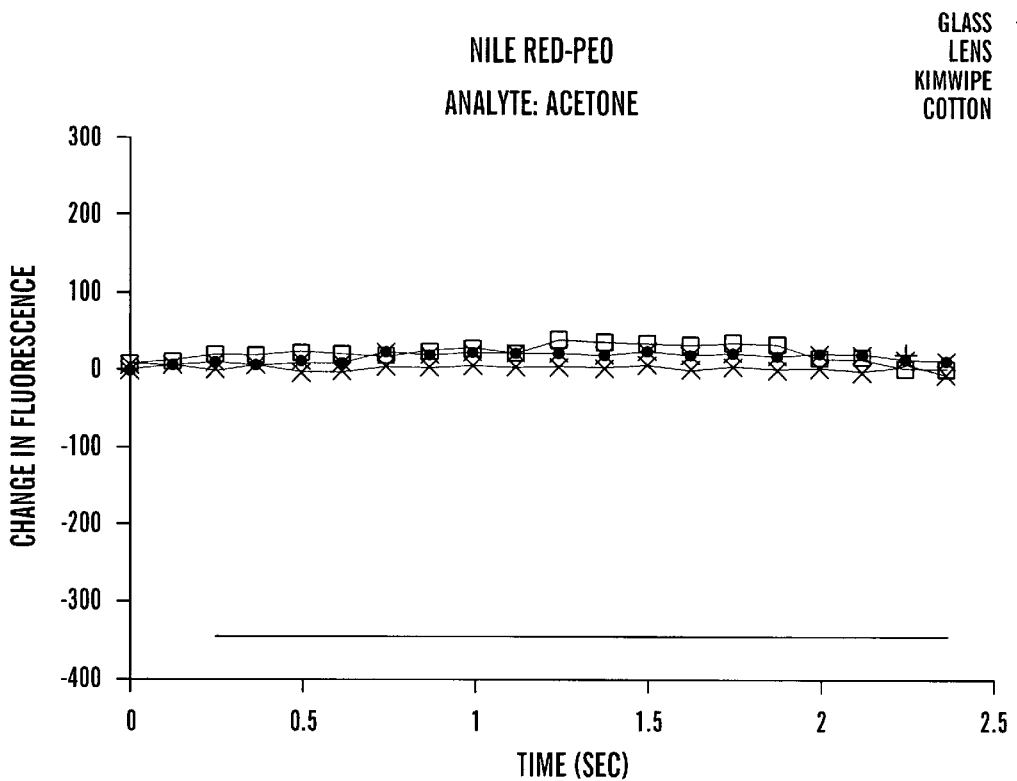
Figure 17D:
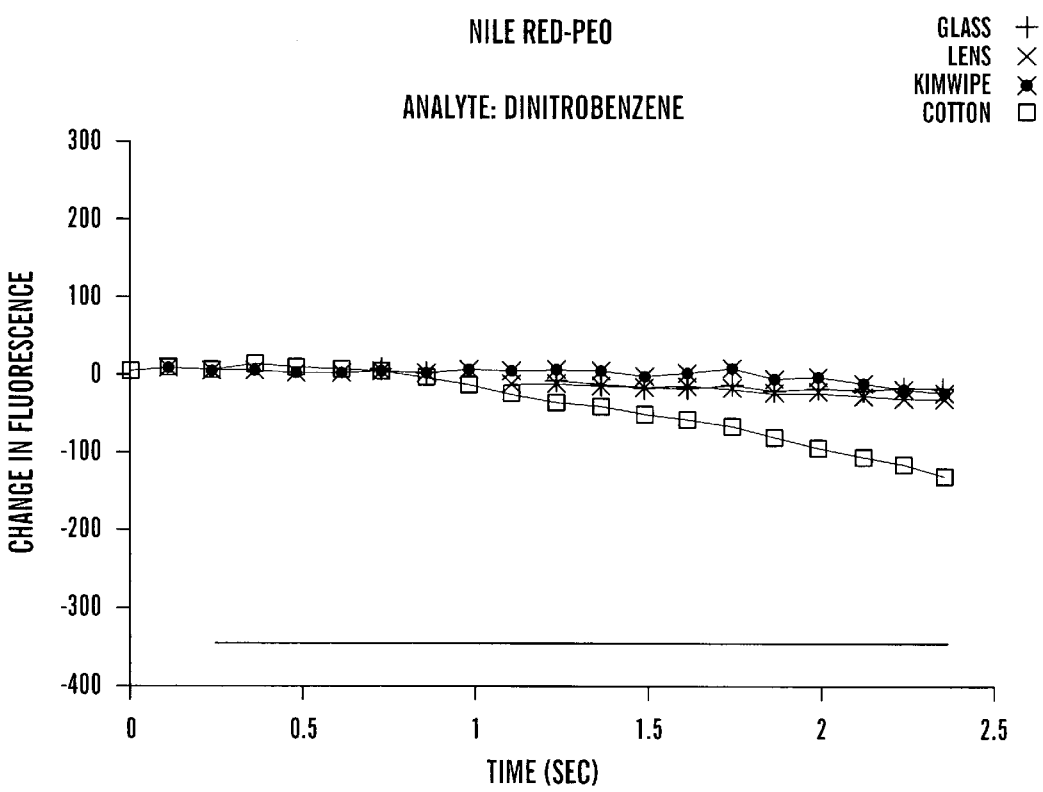
Figure 22:
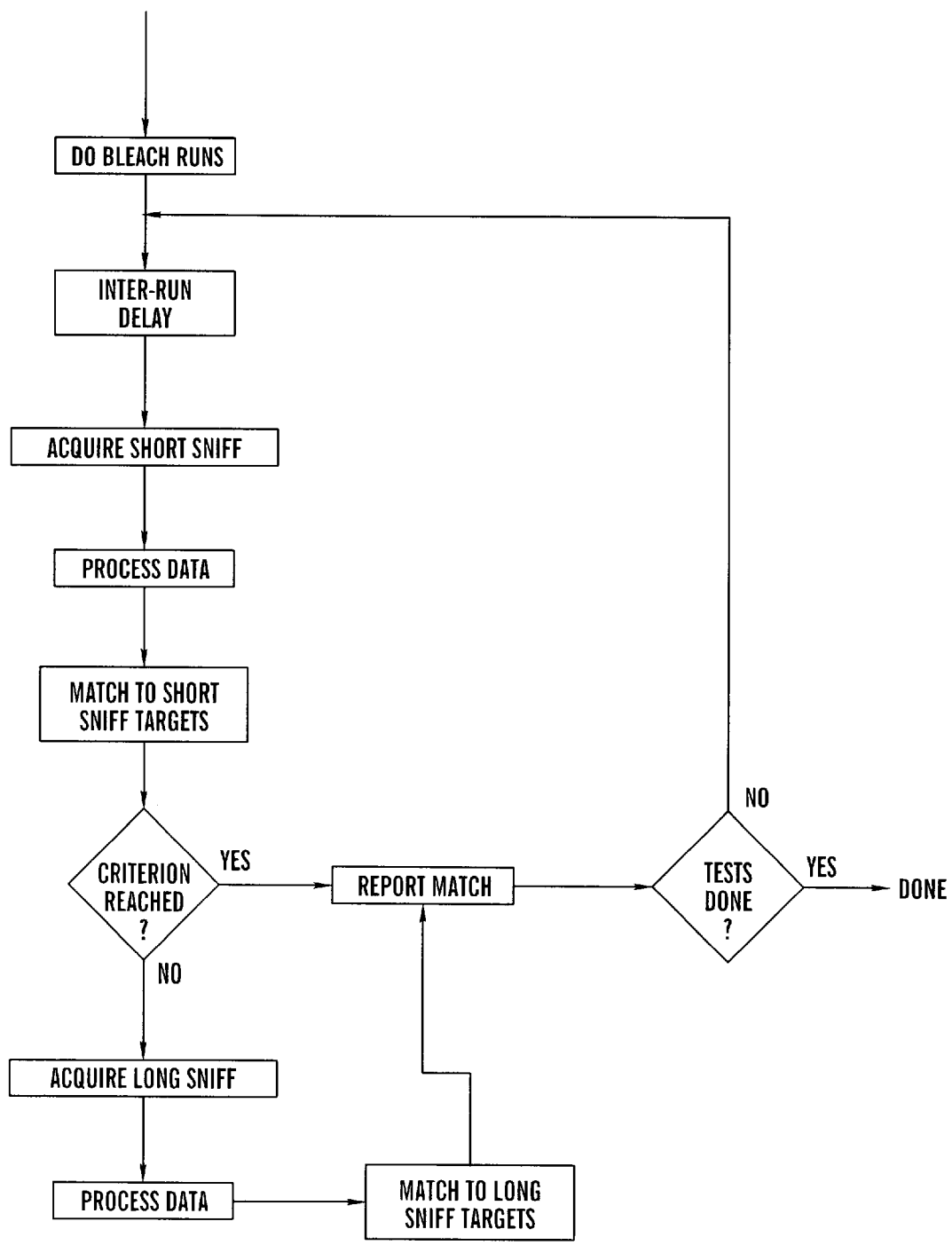
FIG. 22 is a schematic flowchart of the analyte test method employed in the smart sensing method of Example 3.
Figure 23A:
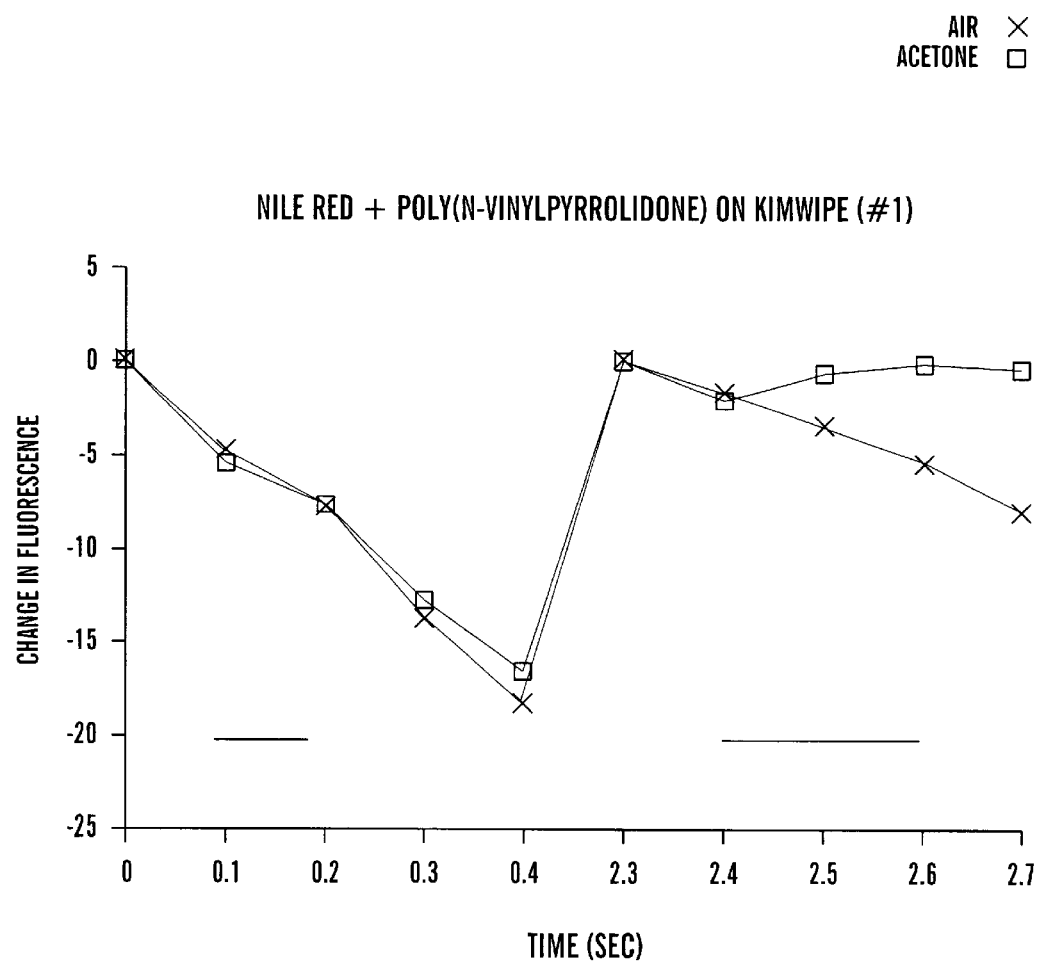
FIGS. 23a–d are plots of sensor fluorescence responses to acetone and air target analytes with short and long sniffs when using the smart training method of Example 3.
Figure 23B:
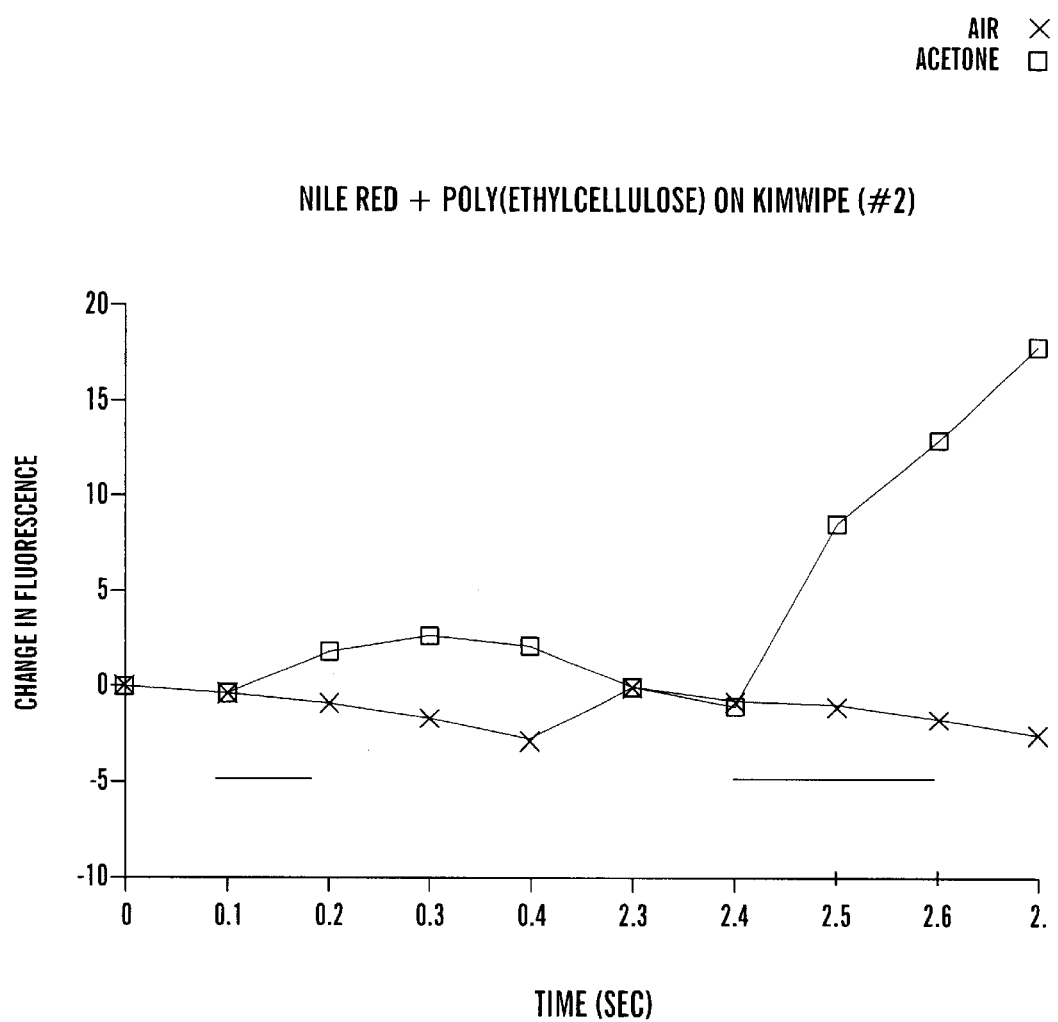
Figure 23C:
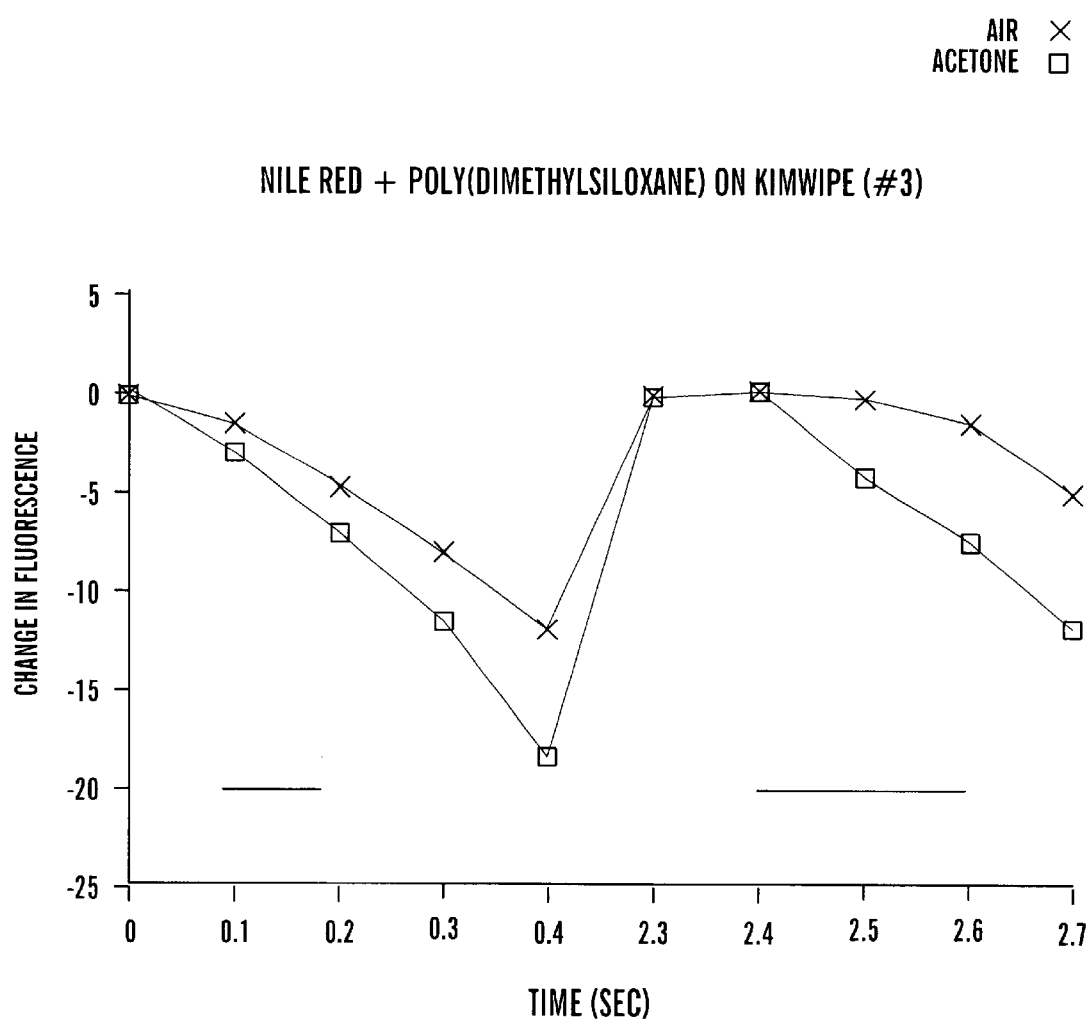
Figure 23D:
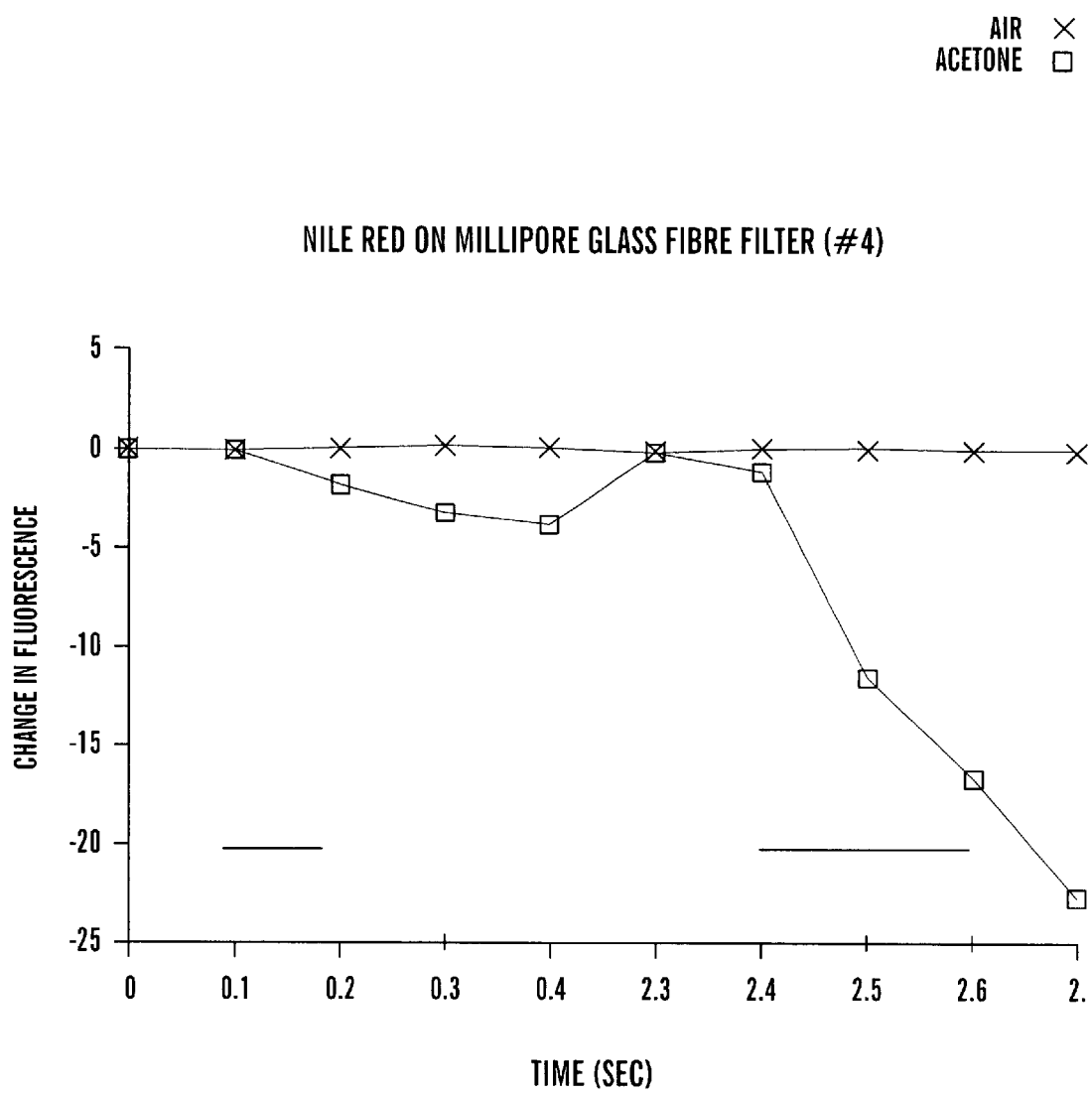

FIGS. 16 and 22 provide schematic flowcharts of typical sampling procedures employed with the sensing device of the present invention. Further details of smart mode sampling are discussed in later sections and details of one sampling method embodiment are described in Example 3.

Figure 14:
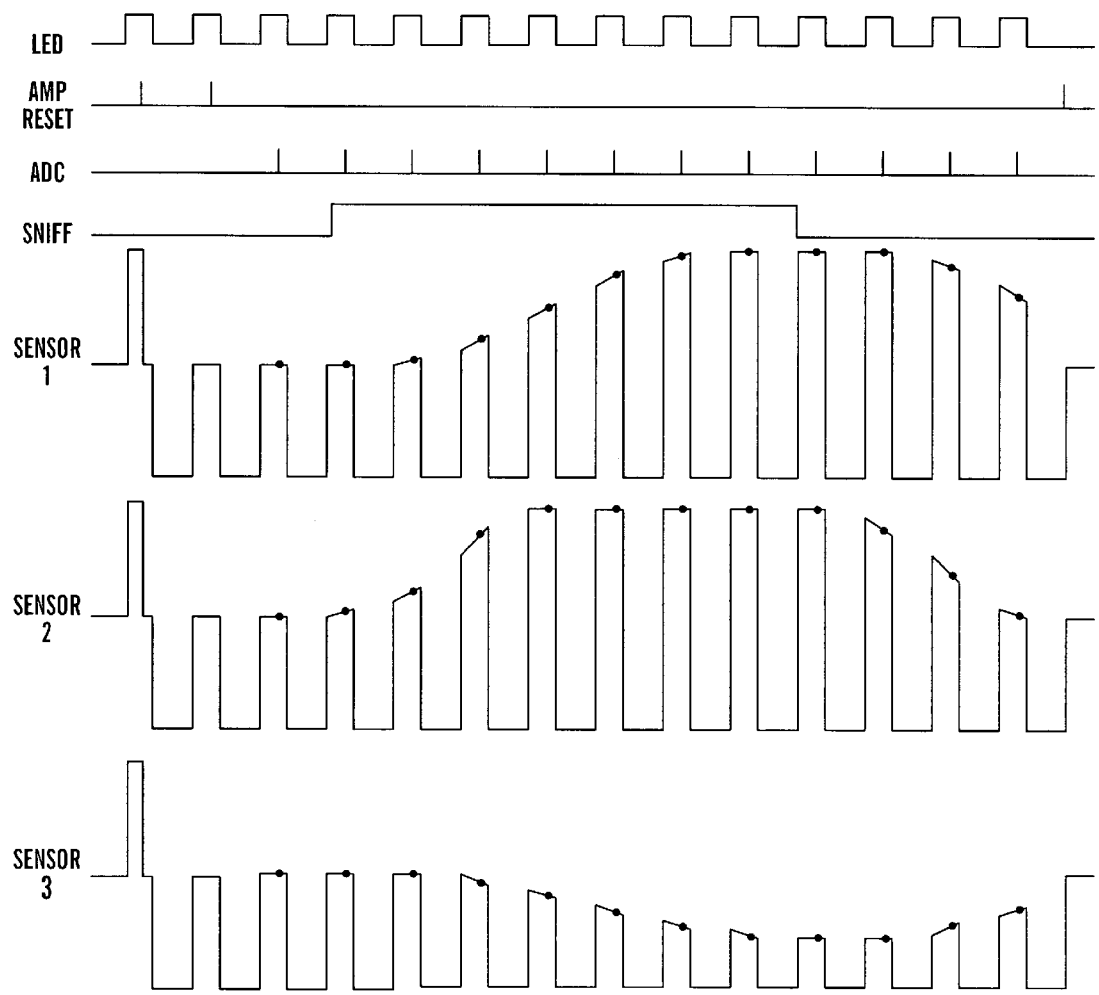
FIG. 14 is a schematic of a data acquisition timing diagram used in the sensing method of the present invention.

The sequence of steps for sampling analyte-containing fluids are similar to the training runs described above. A typical sampling sequence is shown schematically in FIG. 16 and discussed in more detail in later sections. The entire sampling sequence is controlled by an microcontroller computer embedded in the sensing device. The sample timing sequence is shown in FIG. 14. A typical sampling run sequence is as follows:

1. Set inhalation and exhalation fan valves in partial exhale mode to prevent uncontrolled diffusion of ambient analytes into sample chamber.
2. LED's are turned on for 100 ms.
3. Amplifier baselines are reset while LED's are on (this zeroes out the background fluorescence).
4. LED's turned off
5. Wait 150 ms
6. Steps 1–3 repeated 5 times to insure amplifier reset is stable.
7. Analyte response run begins
8. Turn on LED's for 100 ms
9. Take an analog data point from each sensor, convert to digital value with 12 (0–4095) bit accuracy, place digital value in memory
10. Turn LED's off
11. Wait 150 ms
12. Repeat steps 8–11 one time (this is before analyte presentation)
13. Switch inhalation valve on and exhalation valve off (see FIG. 6a)
14. Repeat steps 8–11 four times (for 1 sec analyte pulse)
15. Switch inhalation valve off and exhalation valve on (see FIG. 6b)
16. Take 4 more data points (repeating steps 8–11)
17. Analyte presentation and data acquisition phases are complete
18. Evaluation circuits and algorithms characterize spatio-temporal response data of the array either via pattern recognition algorithms, template matching, a neural network, statistical analysis, or other analytical methods for analyte identification
19. Results may be displayed on screen, spoken by voice synthesis, or plotted as a three-dimensional response surface of fluorescence changes from each sensor at each time point during sampling. If sensing device is on robotic vehicle, results are processed for feedback control and decision is made to stay on course or execute an appropriate maneuver Optionally, where multiple samples or complex mixtures containing multiple analytes are being sampled, the above sampling steps may be repeated following initiation of the next analyte application with data sampling and acquisition modifications based on intelligent feedback via smart algorithms. Thus, real-time, on-the-fly feedback can dynamically modulate either LED, photodiode, or sniffing hardware settings, or, alternatively, analyte sampling parameters such as, sample duration, rise time, relaxation time, delay from previous sniff, amplifier gain and time constants may be modified. These modifications may be imposed on the next data acquisition within the same sampling trial until detection and identification of the analyte occurs.

D. Data Acquisition

FIG. 14 shows the timing events for a typical data acquisition run during sampling. The smart mode features of the present invention provide for feedback to be applied between or within single sniffs. The top four traces in FIG. 14 represent control signals; the bottom three traces represent signals from three different sensor channels, illustrating different responses to the same analyte. Upward deflections in the "LED" trace indicate when the LEDs are turned on. Upward deflections in the "Amp Reset" trace indicate control pulses sent to the amplifier to reset the baseline to zero. Thus, the first upward deflection for each sensor is the response to illumination; resetting the amp brings this level to zero. When the LEDs turn off, the sensor signal goes to a negative value (only two amplifier resets are shown here for simplicity—we typically reset five times). The upward deflections in the "ADC" (analog-digital conversion) trace indicate when data points are collected, digitized, and stored in computer memory. These data points are represented by dots on the sensor traces. The upward deflection in the "Sniff" trace indicates when inhalation occurs and analytes reach the sensors. "Sensor 1" shows a slowly responding sensor that shows an increasing fluorescent signal to a saturating level with analyte, "Sensor 2" shows a rapidly responding sensor that quickly saturates, and "Sensor 3" shows a slowly responding sensor that shows a decreasing fluorescent signal, but does not saturate.

As shown in FIG. 14, LEDs are pulsed (LED trace) to reduce problems with sensor photobleaching. The amplifier reset (Amp Reset trace) is critical during sampling to providing zero offset so that small response signals can still be detected where there is high background fluorescence. Analog/Digital conversion (ADC trace) occurs each time data is collected from sensor element channels in the array. While each sensor element/detector combination within the array will have temporal response pattern, only response timings for three sensor channels are shown in FIG. 14. The dots placed on the sensor response signal schematic indicate times at which data points are collected The three schematic sensor signals represent simple examples of possible response types that would benefit from feedback control. Sensor 1 shows a baseline signal condition. Sensor 2 shows a rapidly responding sensor signal where the signal saturates and is clipped with loss of signal information. With feedback modulation of this sensor during sampling, subsequent runs may be set to lower amp gain to prevent signal saturation and data acquisition speed may be increased to yield more data in the rising portion of the sensor signal. Sensor 3 shows a slowly responding sensor signal. With feedback modulation of this sensor during sampling, data acquisition speed may be reduced in subsequent runs to allow the response signal to develop more fully, yielding a larger signal.

The steps taken in training the sensor and testing for analytes, including data analysis and matching, are shown in the flow charts of FIGS. 15 and 16 and the timing diagram of FIG. 14. Both FIGS. 15 and 16 represent the steps taken in software. The "Acquire" steps are the points where the program controls the hardware to take data as shown in the timing diagram of FIG. 14.

The software program explicitly controls the prebleaching phase, the duration for which the LED' illuminate the sensors, the onset of data acquisition, the application of the analyte, the duration of analyte presentation, the cessation of analyte application, the duration of the integration time for each data point, the number of time points, and the interval between time points. All of these parameters can be modulated either by direct operator intervention or, alternatively, by programming the microprocessor with smart algorithms that modify the sampling, data acquisition, or analysis steps through real-time feedback control.

E. Data Analysis

The data are filtered, smoothed, statistically evaluated, compared with libraries of stored templates for odor identification, and/or operated on by any of the algorithms discussed below. The data are typically stored in memory as an array of numbers representing the temporal changes in fluorescence in each sensing channel.

1. Detection Methods and Algorithms

A. Evaluation of Synchrony, Response Signals and Noise Characteristics

To improve the detection and discrimination capability of the sensor of the present invention, additional algorithms may be employed to evaluate "synchrony" of response data across different sensor elements to identify small response signals and reject noise. Evaluation of "synchrony" refers to analyzing how many signals coming from identical sensors are similar in the context of when they occur during the sniff cycle. The field that encompasses analytical algorithms is very large and many analytical approaches are available. Due to the innovative features of the present invention, such as the use of multiple detector channels with different wavelengths, use of single or multi-pulsed analyte presentation, and the ability to acquire data from sensor elements in parallel rather than serially, the design of the present invention enables consideration of a number of alternative algorithms beyond those that are conventionally used in artificial noses. This is what is meant by the term "synchrony". Additionally, in preferred embodiments algorithms which are based on biological circuits may be employed [see J. White, et al., *Biol. Cybern.* 78:245–251 (1998); J. White, et al., *Anal.Chem.* 68(13):2191–2202 (1996); and S. R. Johnson, et al., *Anal.Chem.* 69(22) :4641–4648(1997), which publications are incorporated herein by this reference]. The device of the present invention may employ synchronously occurring signals in some embodiments since sensor response data are acquired simultaneously in parallel.

B. Detection Algorithms

The degree to which the response matrix of a test substance corresponds to one of the target analyte library matrices stored during the sensor training phase can be evaluated in a number of ways.

In one preferred embodiment, a sum of the squared differences between each value in the test matrix and the training matrix are generated. These sums may be evaluated by subtracting the test matrix from all of the stored matrices. The smallest sum may be used to identify the best target analyte match. This method was used for the specific embodiments described in Examples 1–4.

In an alternative preferred embodiment, a supervised, for example back propagation, neural network approach may be employed. Examples of these methods are provided in J. White, et al. "Rapid Analyte Recognition In A Device Based On Optical Sensors And The Olfactory System", *Anal. Chem.* 68(13):2191–2202 (1996) and S. R. Johnson, et al., "Identification Of Multiple Analytes Using An Optical Sensor Array And Pattern Recognition Neural Networks", *Anal Chem.* 69(22):4641–4648(1997).

In another preferred embodiment, analytical circuits based on the olfactory system may be employed as disclosed by J. White, et al., "An Olfactory Neuronal Network For Vapor Recognition In An Artificial Nose", *Biol. Cybern.* 78:245–251(1998).

In another preferred embodiment, unsupervised neural networks may be used. Principle component analysis and multidimensional scaling are, in effect, unsupervised statistical methods for reducing dimensionality. Generally, unsupervised neural networks organize high dimensional input data into lower dimensional representations. For example, assuming one embodiment of the present device with 32 sensors and 20 time points, a total of 640 data points may be collected. In this embodiment, each analyte presentation can thus be thought of as a point in 640-dimension space, which, while difficult to visualize, may be mathematically manipulated. By averaging across sensors and time, the data dimensionality may be reduced, but typically data dimensionality above about four dimensions is rather difficult to visualize.

Self-organizing maps (SOMs) are unsupervised neural networks that accomplish similar things. Such SOM methods are attractive for representing artificial olfactory system data because they give a visualization of "odor space". In other words, a map of relationships among various analytes can be produced during training; then during testing, the location of a test analyte on the 'map' indicates the relationship of the analyte with respect to this 'space'. Thus, SOMs may help to visualize relationships among analytes, rather than simply indicating the similarity of an unknown analyte to a target. Examples of SOM approaches which may be particularly useful for analyte detection, discrimination and identification are disclosed by T. Kohonen. et al., "SOM-PAK: The. Self-Organizing Map Program Package", Report A31, Helsinki University of Technology, Laboratory of Computer and Information Science, Espoo, Finland (1996) and T. Kohonen, *Self-Organizing Maps*, Series in Information Sciences, Vol. 30, 2$^{nd}$ ed., Springer-Verlag, Heidelberg (1997), which publications are incorporated herein by this reference.

C. Sampling and Detection Parameter Modulation

Upon evaluation of the response matrices generated by the standards used for training, modifications in sniffing parameters, gain settings, and/or filter settings may be made for actual sampling of ambient fluids. In a standard operating mode, these modifications may be made through interventions of an operator who manually changes sampling and data acquisition parameters through the programmable microcontroller or by keyboard entry. In alternative smart operating modes described in subsequent sections, these modifications may be made automatically, on-the-fly by smart sampling and detection algorithms that direct mircocontroller operations.

Whether and how much such modification improve sensing performance may be evaluated by examining sensor responses after feedback and determining, by some predetermined or analytically-derived criterion, whether current sample data are better or worse than data obtained on a previous run. Modifications may also consist of differentially weighting the influence of sensors, so that those sensors that give the best signals have a greater impact in the recognition algorithms. This can be done in a number of ways, such as eliminating sensors that give little or no signal so as to reduce noise, normalizing the remaining signals to some standard value in order to use the maximum range available, or changing analyte sampling and stimulus acquisition paradigm to optimize sniff sampling parameters.

D. Smart Mode Operation

Example 3 provides one example of an embodiment of the smart mode sampling capability of the present invention where the number and duration of analyte samples taken during a sample session are controlled by way of real-time feedback and control loops for improving detection, discrimination and identification of analytes. In other embodiments, alternative smart mode parameters and device sampling configurations may be manually or automatically selected during training and sampling via device menu options. Smart mode sampling configurations may be used alone or in a variety of combinations and permutations. In one anticipated embodiment, an automated training algorithm may be employed to optimize parameter selection and sampling configuration in order to provide the best detection and discrimination capability for specific analytes of interest. Specific examples of alternative smart mode sampling options and parameter configurations are described below.

1. Sampling Parameters

A. Sniff parameters.

i) Sniff duration. This parameter variation is discussed in Example 3 where significant improvements in detection accuracy are realized.

ii) Number of sniffs. In the simplest implementation, signals across multiple sniffs may be averaged to improve signal-to-noise. However, different sensors exhibit different long-term responses to multiple sniffs (providing either increasing signal, decreasing signal, or constant signal over a series of sniffs). Monitoring these changes over sniffs (rather than simply averaging the signals) could provide additional information for analyte discrimination.

iii) Sniff dynamics (rise time, fall time). The rate and extent of sample chamber valves opening and closing may be controlled to modify sampling (sniff) dynamics. Changing the sniff dynamics may enhance differences in the rising and falling phases of the sensorresponse.

iv) Sniff velocity. In one anticipated embodiment, a digital-to-analog line may be used to control a transistor that could change the voltage supplied to the sniff fan and alter fan velocity. Changing sniff velocity, in conjunction with changes in sniff duration, may provide optimized exposure of the sensors to particular analytes.

v) Exhalation velocity. As with changing sniff velocity, a change in exhalation velocity would alter the rate at which analyte is purged from the sensors and the dynamic sensor response may then be monitored in subsequent sniffs for improved analyte discrimination.

B. LED intensity. While higher LED intensity leads to more rapid photo-bleaching and sensor degradation, it also tends to yield larger sensor response signals during analyte exposure. In one smart mode embodiment, normal sampling would be made at lower LED intensity and, where small response signals are present, LED intensity may be increased incrementally until reliable response signals are produced for analyte detection. This smart mode would tend to extend sensor lifetime by operating at minimum LED intensity to reduce photobleaching.

C. LED wavelength. The excitation wavelength of the LED may be modulated. LEDs are commercially available that produce three separate wavelengths. The wavelength of conventional LEDs may be modulated by changing applied voltage and flicker frequency. The capability for changing LED wavelength may permit the device to optimally excite the sensors and to change that excitation over sniffs to improve discrimination.

D. Amplifier gain settings. Under typical sampling conditions, the highest gain settings are employed. Under such a condition, some analytes produce sensor signals that saturate the amplifier. By providing for adjustment of gain settings during smart mode sampling, if an amplifier channel saturates, an additional sniff at a lower gain setting would provide more accurate time course and amplitude information.

E. Amplifier temporal filter settings. In general, changing temporal filter settings may not be entirely straight-forward since sensor LEDs are typically flashed during sampling to reduce light exposure. As shown in FIG. 14, data acquisition and A/D conversion are closely correlated with LED pulse timing. However, since some detection enhancement may be achieved by modifying the timing of data acquisition during an LED pulse for improved signal discrimination for specific analytes, modulation of this parameter may improve detection and identification of certain analytes.

F) Gain and temporal filter settings for individual channels. While one current embodiment of the amplifier electronics allow manipulation of gain and filter settings globally (i.e. gain and filter changes apply to all channels simultaneously), in alternative sensor embodiments, individual sensor channels may also be manipulated for smart mode sampling and detection.

Smart mode training and sampling procedures using these and other parameter variations are discussed in greater detail below.

2. Smart Mode Training

FIG. 15 provides a schematic flowchart for smart mode training procedures. Smart mode training is divided into two main sections: first, the parameters defining the "primary" sniff are determined, followed by a determination of parameters for any "secondary" sniff(s) that may be necessary. The constraints for the two sets of parameters are different: The primary sniffs are applied at regular intervals over long periods of time and should have minimum impact on sensor lifetime since they expose the sensors to as little light as possible to reduce photobleaching and to as little analyte as possible to prolong sensor lifetime and shorten recovery time. Secondary sniffs are intended to generate signals that allow better discrimination to take place.

A. Photobleaching and Bleach Runs

Exposing a fluorescent sensor to excitation light produces photobleaching, decreasing the fluorescent output of the sensor. This fluorescence recovers over time after the excitation light is turned off. When sensors are exposed to excitation light during acquisition of response data at variable intervals, there appears to be more variability in sensor response. Preferably, response data are acquired at regular intervals within 15 second periods. Sensor bleach runs establish this regular interval before data are actually acquired. The bleach runs are repeated until the signals from the sensors stabilize.

Bleach runs are acquired without sniffing or taking a sample. The response matrices from these runs are compared to the previous run by calculating the sum of squares (SS) difference for all data points. For the first run, the comparison is to a matrix of zeroes. If the SS difference is stable, where successive SS differences change little, training target sampling is initiated. If the SS difference is unstable, an 15 second inter-run delay time is used and then the bleach run is repeated. While the operator may evaluate the SS difference stability visually, this process may be automated by setting a criterion which provides for minimum changes in successive SS differences; when that criterion is reached, the program continues and training target sampling is initiated.

B. Establish Primary Parameters

Device parameters are initialized to settings that should give discriminating signals upon analyte exposure. For example, the LEDs are turned up to the highest intensity by sending the highest voltage possible out the D/A line (FIG. 3) to the LED controller (FIG. 5) and a long sniff at high flow is acquired by sending a voltage signal through the D/A control line (FIG. 3) through an LM317 circuit to control the inhale servomotor and fan and shown in FIGS. 3 and 6a. This section of the program finds the minimum values for these parameters that leads to discrimination of analyte signals from air. In the flow chart shown in FIG. 15, the rectangles with rounded corners represent subroutines of several steps that are described below. The "criterion" referred to here is initially determined through experimentation with a particular set of sensors and can be subsequently incorporated into the programmable microcomputer for automatic control.

1. First, sensors that do not respond to any of the analytes are found. Data from all analytes and air are acquired. For each sensor, the SS difference between air and each analyte is calculated. If a sensor does not produce a SS difference value above criterion for any of the analytes in the training set, that sensor is removed from consideration for subsequent training and testing.
2. Second, the lowest permissible sniff flow is determined:
   a) Take single sniffs of all analytes and air.
   b) Calculate SS differences between response matrices of each analyte and air
   c) If SS difference values are all above a criterion, reduce sniff flow velocity by 10% (i.e., reduce voltage of D/A by 10%) and repeat from step 1, otherwise increase flow velocity by 10% (unless flow is already maximal) and stop.
   d) All data are saved to flash (non-volatile) memory for possible later use.
3. Third, a similar procedure is used to determine the dimmest LED setting:
   a) Take single sniffs of all analytes and air.
   b) Calculate SS differences between response matrices of each analyte and air
   c) If SS difference values are all above a criterion, reduce LED intensity by 10% (i.e., reduce voltage of D/A by 10%) and repeat from step 1, otherwise, increase LED intensity by 10% (unless LED intensity is already maximal) and stop.
   d) All data are saved to Flash Memory for potential use later.
   e) Because the level of excitation light is likely reduced by the preceding steps, another set of bleach runs is then taken.
4. Fourth, the shortest sniff is determined:
   a) Take single sniffs of all analytes and air.
   b) Calculate SS differences between response matrices of each analyte and air
   b) If SS difference values are all above a criterion, reduce sniff duration by half (i.e., open sniff valve for half the time) and repeat from step 1, else double the sniff duration (unless sniff duration is already maximal) and stop.
   c) All data are saved to Flash Memory for possible later use.
5. Fifth, the fewest time points to collect is determined. Start with the short sniff data stored in the previous step (it is not necessary to collect new data here):
   a) Start by considering data up to the time point just after the sniff begins.
   b) Calculate SS differences between response matrices of each analyte and air
   c) If SS difference values are all above a criterion, stop. Else consider 1 additional time point (unless the number of time points is already maximal) and repeat from step b.
   d) Because the number of time points to collect is likely reduced by the preceding steps, another set of bleach runs is taken.

The result of the "Establish Primary Parameters" section is now the lowest flow, dimmest LEDs, shortest sniff, and fewest time points necessary to discriminate analyte signals from air.

C. Establish Secondary Parameters

The goal of this section is to determine the parameters of one or more subsequent sniffs, if necessary, that will improve discrimination of analytes that are not discriminating based on the primary sniff alone. The parameter adjustments occur only for the analytes that are difficult to discriminate. The "criterion" referred to here is determined through experimentation with the particular set of sensors used. It may be different from the criterion used in the primary parameters section above.

Step 1. Data from all analytes and air are acquired. If this is the first time through this step, only primary sniffs are defined and acquired. These data are saved as the primary sniff targets. The SS differences between each pair of response matrices is calculated This includes responses to secondary sniffs, if defined. If all SS difference values are above a criterion, all targets are deemed to be capable of discrimination. Names are assigned to the targets and the system is ready for testing (FIG. 16). Otherwise, go to step 2.

All of the following steps are applied only to those analytes that fail to meet the criterion of step 1.

Step 2. If the number of sniffs for the "difficult" target analytes has reached a user-determined maximum, this value will probably be on the order of 3 or so sniffs, warn the user about the difficult targets. Assign names to the targets and go to testing.

Step 3. Increment the sniff number by 1.

Each parameter block attempts to optimize the stated parameter for each of "difficult" targets. The parameter blocks may be ordered as shown so that the first five parameter modulations do not increase the amount of excitation light exposure.

1. Parameter #1—Difficulty in discrimination may be due to saturation of the amplifier channel. This is apparent if the signal from any amplifier channel reaches a value of approx. 2000 or −2000 and stays at that level for 2 or more time points. The Yale amplifier has gains of 1000×, 200×, 50×, and 1×. If saturation occurs, follow the following steps:
    a) Decrease the amplifier gain one step and acquire data from the difficult targets.
    b) If the SS difference between the difficult targets is now above criterion, retain this gain setting for these difficult targets and go to step 1. If the amp gain is at minimum (i.e., none of the lower amp gains improved discrimination), go to step c. Otherwise, repeat from step a.
    c) If any of the gain settings produced some improvement, retain this setting. Otherwise, reset parameter to original value and go to next parameter block.

2. Parameter #2—Since data from longer sniffs may have been acquired in the "Establish Primary Parameters" section, investigate those stored data for improved discrimination. If the SS difference between the difficult targets for any of the longer sniffs is above criterion, retain the best setting and go to step 1. Else, go to the next parameter block. If some improvement was made (but still below criterion), retain the best setting. Otherwise, reset parameter to original value.

3. Parameter #3—Since data from higher sniff velocities may have been acquired in the "Establish Primary Parameters" section, investigate those stored data for improved discrimination. If the SS difference between the difficult targets for any of the higher sniff velocities is above criterion, retain the best setting and go to step 1. Else, go to the next parameter block. If some improvement was made (but still below criterion), retain the best setting. Otherwise, reset parameter to original value.

4. Parameter #4—For a sniff, the valves are normally opened and closed abruptly (i.e., the PWM signal to the servo changes from one position to the other instantly). For some analytes and some sensors, opening and/or closing the valves more slowly may help produce discriminating signals. To open/close the valves slowly, the PWM signal to the servos will be changed in smaller steps over time. In other words, instead of opening the valve fully at a particular time point, open the valve in two steps over two time points by opening the valve half way for the first time point, then fully the next. For an even slower opening, use three steps: open ⅓ at one time point, ⅔ the next, and fully the next. A maximum of 5 steps will likely be sufficient.
    a) Slow sniff on rate by increasing the number of opening steps by 1; acquire data from the difficult targets.
    b) If the SS difference between the difficult targets is now above criterion, retain this sniff setting for these difficult targets and go to step 1. If the number of sniff steps is at maximum (i.e., none of the fewer steps improved discrimination), go to step c. Otherwise, repeat from step a.
    c) Reset number of steps to original value.
    d) Slow sniff off rate by increasing the number of closing steps by 1; acquire data from the difficult targets.
    e) If the SS difference between the difficult targets is now above criterion, retain this sniff setting for these difficult targets and go to step 1. If the number of sniff steps is at maximum (i.e., none of the fewer steps improved discrimination), go to step f. Otherwise, repeat from step d.
    f) If any of the sniff on or off settings produced some improvement, retain the best setting. Otherwise, reset parameters to original values and go to next parameter block.

5. Parameter #5—The amplifier filters are normally set at DC—no high-pass filtering at all. Adding high-pass filtering may help to accentuate the rising or falling phases of the sensor signal, leading to improved discrimination. The filter settings available on the Yale amplifier have time constants of 500 ms, 100 ms, and 30 ms (increasing the high-pass cut-off frequency). These values are set using the digital output lines from the Tern computer (FIG. 3).
    a) Increase the amplifier high-pass cut-off one step and acquire data from the difficult targets.
    b) If the SS difference between the difficult targets is now above criterion, retain this filter setting for these difficult targets and go to step 1. If the filter cut-off is at maximum (i.e., none of the lower filter settings improved discrimination), go to step c. Otherwise, repeat from step a.
    c) If any of the filter settings produced some improvement, retain the best setting. Otherwise, reset parameter to original value and go to next parameter block.

6. Parameter #6—Since data from brighter LEDs may have been acquired in the "Establish Primary Parameters" section, investigate those stored data for improved discrimination. If the SS difference between the difficult targets for any of the brighter LED settings is above criterion, go to step 1. Otherwise, go to the next parameter block. If some improvement was made, but it is below the criterion, retain the best setting. Otherwise, reset parameter to original value.

7. Parameter #7—Since data from more data points may have been acquired in the "Establish Primary Parameters" section, investigate those stored data for improved discrimination. If the SS difference between the difficult targets for any of the increased data points is above criterion, go to step 1. Otherwise, go to the next parameter block. If some improvement was made, but it is below the criterion, retain the best setting. Otherwise, reset parameter to original value.

8. Parameter #8—It is possible that changing exhale velocity between sniffs may improve signals for the second sniff. This parameter block is placed last in order to attempt to add to improvements produced by previous parameter blocks that are still below criterion.
    a) Decrease exhale velocity by 10% (i.e., decrease voltage to exhale fan via D/A lines and LM317 voltage controller) and acquire data from the difficult targets.
    b) If the SS difference between the difficult targets is now above criterion, retain this velocity setting for these difficult targets and go to step 1. If the velocity is at minimum (i.e., none of the lower velocities improved discrimination), go to step c. Otherwise, repeat from step a.
    c) Reset velocity to original value.
    d) Increase exhale velocity by 10% and acquire data from the difficult targets.

e) If the SS difference between the difficult targets is now above criterion, retain this velocity setting for these difficult targets and go to step 1. If the velocity is at maximum (i.e., none of the higher velocities improved discrimination), go to step f. Otherwise, repeat from step d.

f) If any of the velocity settings produced some improvement, retain the best setting. Otherwise, reset parameter to original value. If the program reaches this point without reaching criterion, then none of the parameter changes improved discrimination. Warn the user about the difficult targets, assign names to the targets, then go to testing.

D. Smart Nose Testing

FIG. 16 provides a schematic flowchart for smart mode testing procedures. Smart Nose testing a single analyte can occur in two stages. First, a primary sniff is taken and, if the primary sniff produces a good match to a target, that match is reported. Secondly, if the primary sniff does not produce a good match, one or more secondary sniff(s), if defined by training, are taken. If a match criterion is not reached, the matching difficulty is noted and the closest match reported. If the goodness criterion is reached, the match is reported.

1) Testing begins with parameters determined by "Establish Primary Parameters" section of training.
2) Take bleach runs, as described under Training.
3) After an inter-run delay, acquire a primary sniff and process the data.
4) The primary sniff data matrix is matched to the primary sniff targets by calculating the SS difference to each target (as described above).
5) If "goodness" criterion is reached, report the match. Continue testing.
6) Otherwise, does target with lowest SS difference have secondary sniff(s) defined? If not, note difficulty, report this target and continue testing.
7) Otherwise, set the appropriate secondary parameters.
8) Acquire the secondary sniff(s) and process the data.
9) The secondary sniff data matrix (or matrices, if more than one sniff) is/are matched to the secondary sniff targets by calculating the SS difference to each target.
10) If A "goodness" criterion is reached, report the match. Otherwise, note difficulty, report closest target, and continue testing.

E. Sensitivity Improvements and Other Enhancements

With certain analytes, for example 2, 4 dinitrotuluene (DNT), which is a major constituent of some explosives, the sensing system of the present invention has demonstrated very high sensitivities and detection limits, for example 2–7 parts per billion (ppb) which are at least an order of magnitude lower than the best detection limits reported for conventional fiber optic sensing devices.

The improved sensitivity, detection and discrimination capabilities observed with the sensor of the present invention are due to a number of innovative features. The photodiodes employed in the present invention are intrinsically more sensitive than and have larger dynamic range than individual pixels of conventional CCD camera detectors. The detection surface area of individual sensor photodiodes in the present device is larger than individual pixel areas of conventional CCD camera detectors. Additionally, due to the surface area of the LEDs and photodiodes employed in the present invention, larger sensor element areas may be employed and sampling is conducted over a larger geometric surface area of individual the sensor elements. Furthermore, the innovative liquid permeable, high porosity high surface area sensor substrates of the present invention, further enhance sensor response signals due to a substantial increase in sensor surface area to volume ratios and the volumetric sampling of sensor response signals generated within a three-dimensional substrate-sensor volume.

Another source of increased sensitivity in the present invention is the capability to reset the baseline of the amplifiers after turning on the excitation light in order to look only at fluorescence differences above background, rather than the background illumination itself. Thus we are not limited by having to reduce gain or light intensity to prevent detector saturation as observed with conventional CCD camera detectors. The amplifiers utilized in the present invention are specifically designed for resetting signal baseline in order to look at small fluorescence changes on a large background. In addition, readout from the photodiodes employed in the present invention is intrinsically less noisy than readout from pixels from CCD camera detectors employed in conventional devices because the readout speed per channel with the present invention is lower than that of CCD camera detectors and higher signal-to-noise ratios are achieved.

The enhanced sensitivity of the present sensor may be further augmented by utilizing multiple layers of sensing material 'suspended' in the air stream, employing larger surface area sensor elements and larger surface area photodiodes, and/or using replicates of multiple identical detectors in the sensor array from which signals are combined electronically. Replicates of different sensing materials may be incorporated into different sensor channels. Using replicates provides advantages not only with respect to the duplication of data to verify measurement reproducibility, but also with regard to reducing non-correlated noise from electronic components such as amplifiers.

EXAMPLES

Example 1

Sensor Response Enhancement

For evaluating the impact of substrate materials on sensor response signal enhancement four different sensor substrates were evaluated including:

a) a solid glass coverslip; b) a fine tissue paper (Kimwipe™); c) a porous, low density lens paper; and d) a small ball of cotton. Four substrates were employed with sensor elements fabricated from Nile Red dye and polyethylene oxide (PEO) according to the methods described above. Two substrates were employed with sensor elements made from a pentiptycene-derived phenylenecthynylene polymer 1 ("PDPP1") synthesized according to the method described previously [SeeYang and Swager in *J.Am.Chem.Soc.* 120:11864–11873(1998), which is incorporated herein by reference].

Individual sensor substrate response signals to analyte vapor were simultaneously measured for each substrate during sample runs. For PEO-Nile Red sensors, an excitation wavelength of 533 nm, with a 40 nm band pass, and an emission wavelength of 620 nm, with a 10 nm band pass, was used. For the PDPP1 sensor measurements, excitation wavelengths of 460 nm and 430 nm, with a 10 nm band pass, and emission wavelengths of 488 nm, 500 nm, and 510 nm, with a 10 nm bandpass were employed.

Figure 18:
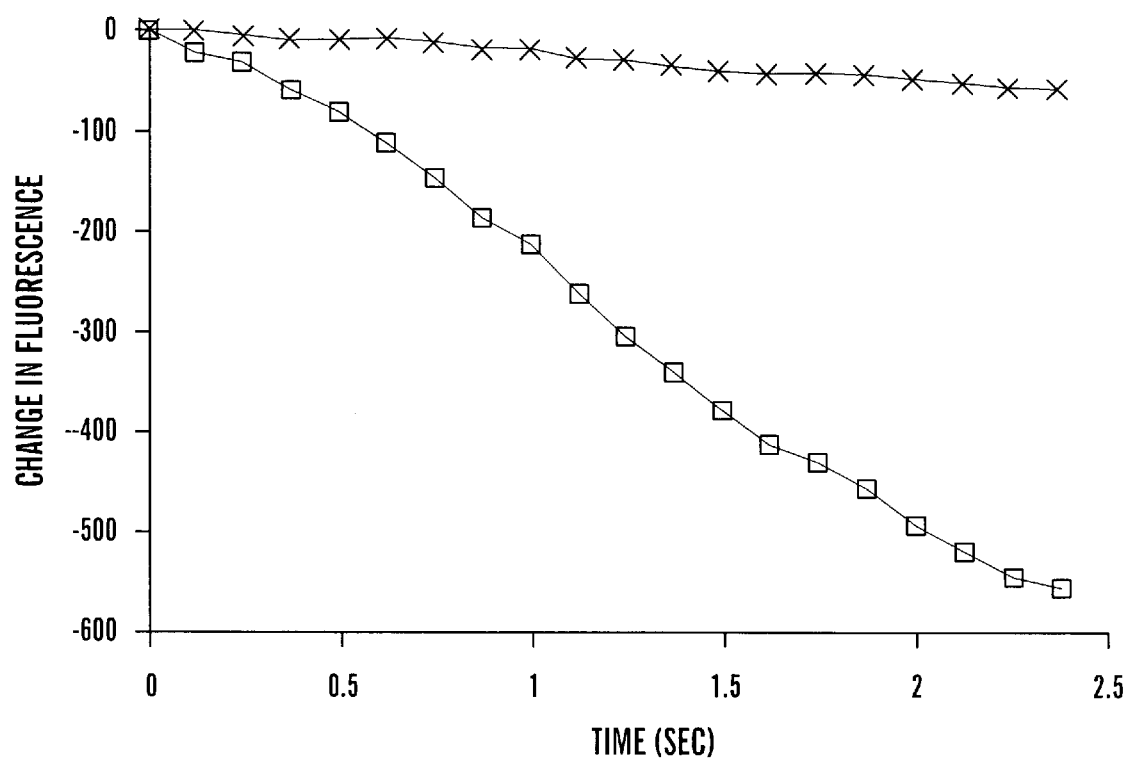
FIG. 18 shows comparative changes in fluorescent sensor response to saturated DNT explosive analyte with conventional glass sensor substrates and an innovative sensor substrate of the present invention.
Figure 19A:
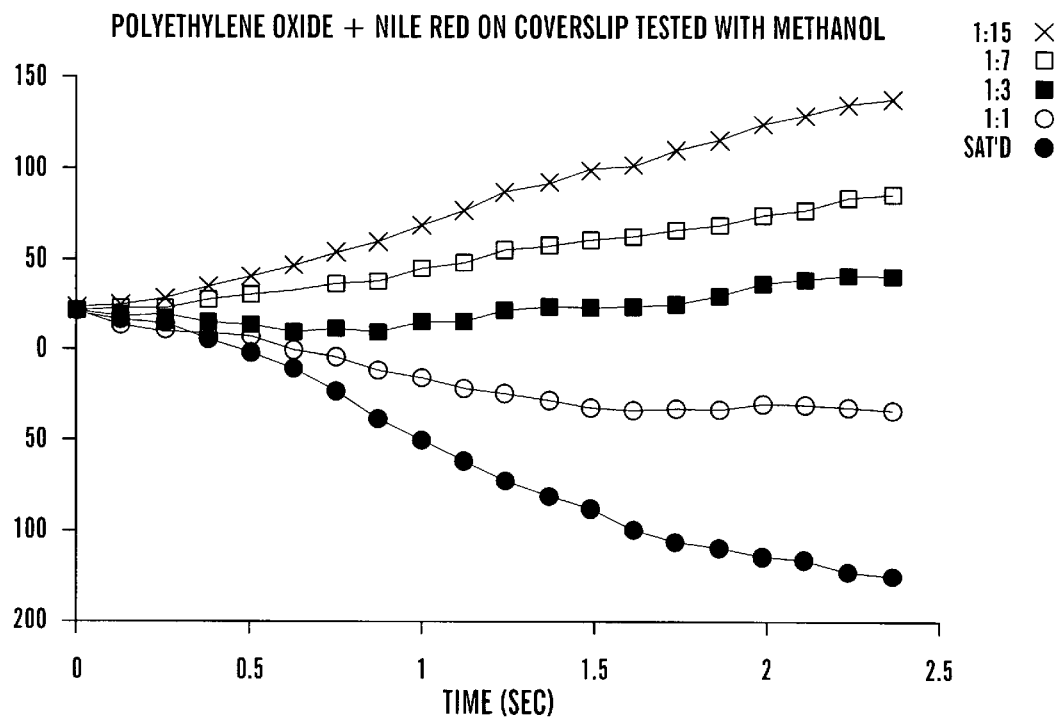
FIGS. 19a–b show comparative changes in fluorescent sensor response to methanol samples at various analyte concentrations with a conventional glass sensor substrate and an innovative sensor substrate of the present invention.
Figure 19B:
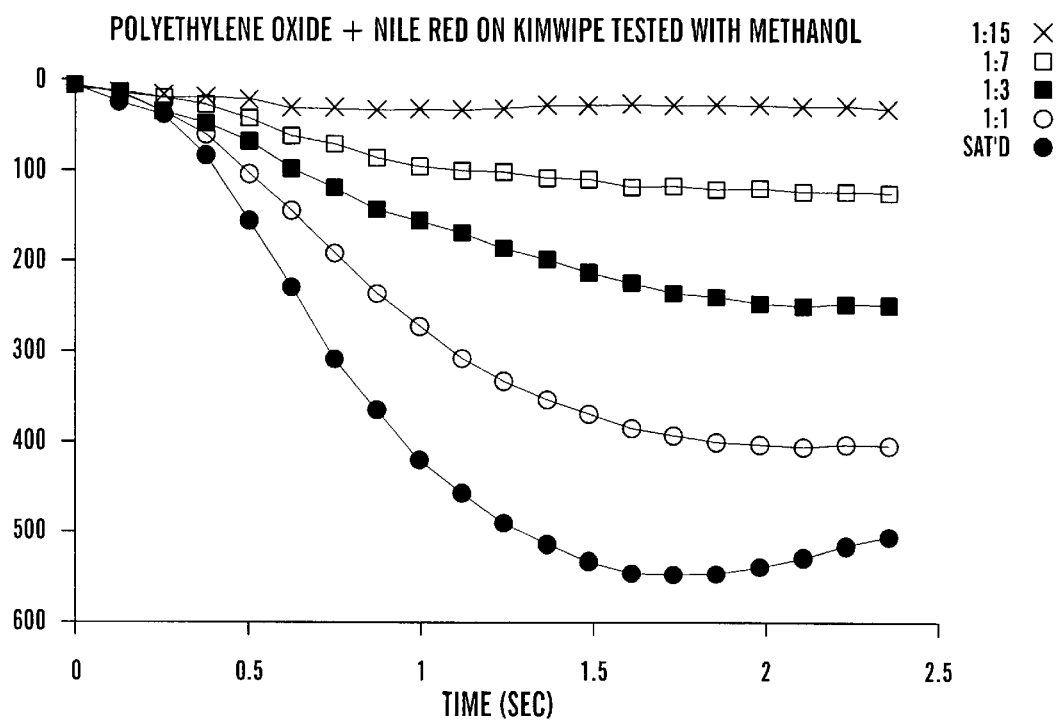

FIGS. 17a–d shows sensor response signals to saturated methanol, amyl acetate, acetone, and dinitrobenzenene analyte samples for PEO-Nile Red dye polymer applied to various substrates. FIG. 18 shows sensor response signals to DNT for the PDPP1 polymer applied to two different substrates. FIGS. 19a–b show sensor response signals to various concentrations of methanol for PEO-Nile Red dye polymer applied to two different substrates. Each trace represents the analyte response with the target air response subtracted. Thus, each trace shows only the signal due to the analyte. Each trace is an average of the signals from two sensors of the same type and from three separate analyte exposures. The traces are not scaled and the y-axis ranges of each plot are the same.

After application of fluorescent dye-polymer materials to each of the substrates, background fluorescence was measured for each sample to verify that any observed signal enhancement was not due to higher background fluorescence. The same excitation and emission wavelengths used in the response signal measurements shown in FIGS. 17a–b, 18, and 19a–b were used for background fluorescence measurements. Voltage measurements were taken from the output of the amplifiers at a test point between the voltage divider and the A/D converters. For background fluorescence measurements, LED intensity was adjusted to a sufficiently low level such that none of the sensors saturated the amplifier. This intensity was much lower than that used during the analyte measurements shown in the plots. For background measurements, the voltages were recorded on a storage oscilloscope while the LEDs were switched on. These measurements represent the difference between the amplifier output before and immediately after the LEDs were turned on before any significant photo-bleaching occurred. Raw output from detector amplifiers was measured in volts. Background fluorescence for each substrate sample were measured as follows:

Glass—0.325

Kimwipe™—0.25

Lens paper—0.275

Cotton—1.2

FIGS. 17a–d shows that both Kimwipe™ and cotton sensor substrates produced substantially enhanced response signals compared to conventional glass substrates. While the background fluorescence measurements indicate that cotton substrates produces the highest background fluorescence, as shown in FIGS. 17a–d, cotton substrate sensor response signal were comparable to Kimwipe™ substrates for methanol analyte and produced the most enhanced response signals with amyl acetate and dinitrobenzene analytes. FIG. 8 shows a dramatic signal enhancement for saturated DNT analyte produced with PDPP1 polymer applied to a Kimwipe™ substrate when compared to glass coverslips. Comparison of the response signals produced by PEO-Nile Red dye polymer on glass and Kimwipe™ substrates are shown for various concentrations of methanol analyte samples in FIGS. 19a and 19b. While no enhancement was observed at dilute concentrations of methanol, a substantial signal enhancement was observed at higher concentration of methanol analyte using the innovative substrates of the present invention.

Example 2

Analyte Response Characteristics

As a demonstration of the analyte detection capability of the sensor of the present invention, eight test samples were prepared from analyte-saturated air. The target analytes comprised an air baseline sample, acetone, amyl acetate, carvone, chloroform, cloves, a commercial cologne (Drakkor Noir™), and isopropanol.

For this experiment, a nine element sensor array was utilized. The methods used for fabricating the sensor elements of the array are described above and in a previous publication [J. White, et al., *Anal. Chem.* 68(13):2191–2202 (1996)]. The sensor element materials employed in this sensor array are as follows:

| 0 | PABS | 1 | PDPO/Alumina |
|---|---|---|---|
| 2 | EC | 3 | Dow |
| 4 | PBA | 5 | PC/Alumina |
| 6 | Dow/Alumina | 7 | PSAN |
| 8 | PC | | |

| | |
|---|---|
| PABS = poly(acrylonitrile-butadiene-styrene) | Poly Sciences |
| EC = ethyl cellulose | Poly Sciences |
| PBA = poly(1,4-butylene adipate) | |
| Dow = a dimethyl siloxane dispersion coating | Dow Corning |
| PC = polycaprolactone | Aldrich |
| PDPO = poly(2.6-dimethyl-1,4 phenylene oxide) | Aldrich |
| PSAN = poly styrene-acrylonitrile | Poly Sciences |
| Alumina = 150 mesh alumina | Aldrich |

Each analyte sample was sampled for 1 second and data was taken over a 2.5 sec data acquisition time with data time points taken every 250 ms. For each analyte, ten samples were measured over a 2.4 second period. For these experiments, all sensors were illuminated at an excitation wavelength of 530 nm (40 nm bandpass) and sensor responses were monitored at an emission wavelength of 620 nm (20 nm bandpass) by application of excitation filters to the LEDs and emission filters to photodiode detectors.

FIG. 20 shows typical spatio-temporal response patterns of a sensor array of the present invention to eight different analyte samples. Each z-axis value in the matrix represents the magnitude of fluorescence above or below the baseline at a specific time point for each specific sensor element. The results shown in FIG. 20 clearly demonstrate the ability of the semi-selective, cross-reactive sensor array of the present invention to detect and discriminate among a wide diversity of analytes.

Example 3

Smart Mode Test Results

To demonstrate one embodiment of the innovative smart mode sampling, detection, discrimination, and identification capability of the present invention, the number of samples taken ("sniffs") and sampling times ("sniff duration") were adjusted and controlled on-the-fly using real-time feedback obtained from prior sampling results.

Since it is generally desirable to provide for sampling at high frequencies and short durations, the sensing device of the present invention provides for frequent and rapid environmental sensing. Two limiting characteristics of dye sensors affect how frequent and how fast samples can be taken. First, fluorescent sensors tend to bleach with long exposure to the excitation light, thereby losing their sensitivity to analytes. Secondly, sensors tend to yield smaller response signals upon long and frequent exposure to analyte and some relaxation or recovery time is generally necessary after such exposure.

Typically, for frequent sampling, it is preferable to make the analyte and light exposures brief. However, brief exposures tend to produce smaller response signals and thus compromise sensor detection limits. These limitations are overcome by smart mode sampling where real-time sampling feedback is applied to optimize sampling time and the number of samples taken. In this mode, short samples are acquired first, results are checked against a defined statistical criteria to determine sample validity, and longer samples are subsequently acquired only where the results of short sampling are ambiguous or unreliable.

To demonstrate this particular implementation of the smart mode sampling capability of the present invention, an eight sensor array comprising two replicates of four dye-polymer sensors were employed for discriminating acetone from air. The sensors used for smart mode sensing are listed below together with their emission and excitation wavelengths. The cellulose fiber substrate used for sensors 1–3 was commercial tissue paper sold as Kimwipe™. The glass fiber substrate used for sensor 4 was a commercial filter paper sold as MilliPore™ Type APFA glass fiber filter (1.6 $\mu$m retention/500–500 um thick). These sensors were fabricated according to the methods described above.

| | | |
|---|---|---|
| #1. | Nile Red/Poly(N-vinylpyrrolidone on cellulose fiber substrate | [ex. 533 nm/em. 600 nm] |
| #2. | Nile Red/Poly(ethylcellulose) on cellulose fiber substrate | [ex. 533 nm/em. 610] |
| #3. | Nile Red/Poly(dimethylsiloxane) on cellulose fiber substrate | [ex. 533 nm/em. 633] |
| #4. | Nile Red on a glass fiber substrate | [ex. 533 nm/em 650]. |

Prior to actual analyte sampling, the sensor was trained for the target analytes according to the methods described previously above. FIG. 21 provides a schematic flowchart of the specific training steps employed in this experiment. Preliminary target data were acquired for each sensor in the array by sampling air and acetone-saturated air for short and long sampling ("sniff") times.

The target sampling results for each analyte and each sensor are provided in FIGS. 23a–d, where responses to both air and acetone are shown for each sensor for both short and long sample times (sniffs). For each analyte, five data points were acquired at 100 ms intervals. Sampling duration was 100 ms for short sniffs and 200 ms for long sniffs. The long sniffs were acquired immediately after the short sniff. It is worth noting that the amplitude of the second sniff response will recover if a long time interval occurs between sniffs. The traces shown in the graphs are the average of two sensor responses for four different runs.

The target data in FIGS. 23a–d are plotted to clarify the temporal relationship between short and long sniffs in the training mode. The horizontal bars toward the bottom of each graph indicate the duration of the two sniffs with the short sniff being first, followed about two seconds later by the long sniff. The dotted lines in the figure depict a two second break in the time axis between sniffs. The two second delay is the amount of time it takes for the embedded computer to process the data from the first sniff and to start up the second sniff. The duration of this delay will vary with the specific hardware configuration employed. This interval may be reduced by either converting most of the data calculations from floating point to integer arithmetic or using a faster computer. Computational power is not a limiting factor. Note that the response intensity range of the y-axis are the same for each figure. The data shown in FIGS. 23a–d are scaled the same way that the embedded computer scales the data during its processing. The most significant features of these plots are the relative signal amplitudes for each analyte and the contribution of each response signal to analyte discrimination.

As shown in FIGS. 23a–d, sensor #1 (FIG. 23a) demonstrated poor discrimination for acetone with short sniff sampling whereas sensor #2 (FIG. 23b), sensor #3 (FIG. 23c), and sensor #4 (FIG. 23d) show marginally better discrimination with short sniffs. With longer sniff sampling, sensor #1 shows improved discrimination, sensor #3 shows marginally similar discrimination and sensors #2 and #4 show dramatically improved discrimination for acetone. In an ideal sampling application, where sensor element response signals are large and noise-free, the sampling system would normally identify target analytes without difficulty. In this example, the less responsive sensors #1 and #3 were chosen to replicate, in a controlled manner, a real sampling situation where the sensing device may become confused due to inconsistent or conflicting response data obtained from multiple sensors and would make errors in identification. For these realistic scenarios, the smart mode sampling would be most useful for detecting, discriminating, and identifying analytes where response signals are either small and/or noisy.

FIG. 22 provides a schematic flowchart of the sampling procedures used for smart mode sampling in this experiment. Initially, short sniffs were acquired every 10 seconds. The measured response was compared to the short sniff targets for air and acetone using a sum-of-squares matching algorithm that is described above. Normally, the target with the smaller match score, or lower sum of least squares, would be reported as the identity of the test analyte. In the smart sampling mode, all target match scores, in this case acetone and air, were evaluated to determine how 'good' the match is. If the match was not 'good' enough, a second, longer sniff was acquired and that match was reported. For detecting target analytes, a 'goodness' criterion was applied to the ratio of the match scores for each analyte. The larger match score may be evaluated by a criterion wherein it must be some threshold number of times greater than the smaller match score. Two examples of this evaluation method is provided below which demonstrate the improvement in acetone recognition using smart mode sensing. Following the approach used in signal detection theory, test matrices are provided in a simplified format which represents the numbers of hits, misses, false alarms (FA), and correct rejections (CR):

```
                              Signal
                              -------
                           Acetone  Air
                           +------+------+
        Decision: Acetone  | Hit  |  FA  |
                           +------+------+
                   Air     | Miss |  CR  |
                           +------+------+
```

In each example, fifty sample runs were made, with 25 runs each of air and acetone. Samples were collected in alternating blocks of five, five air, then five acetone, then five air, etc. For a direct comparison, all data were collected in 'smart nose' mode. For the standard mode representation, only the first short sniff was considered. For the smart mode representation, the final outcome (whether or not one or two sniffs were acquired) was considered.

Example #1:
a) Standard Mode

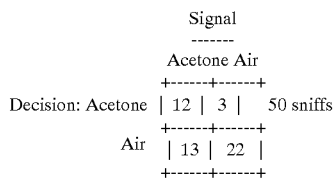

b) Smart Nose Mode

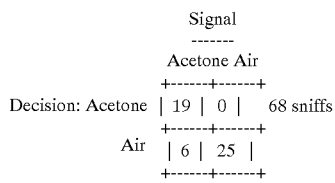

In this example, the 'goodness' criterion was set to two (i.e. the ratio of the larger match score to the smaller match score had to be greater than two). In both modes, the number of correct rejections (reporting air when air was presented) was high. The smart sampling mode improved the number of hits (from 48% to 76%). The smart mode evaluation required 18 additional long sniffs for this improvement.

Example #2:
a) Standard Mode

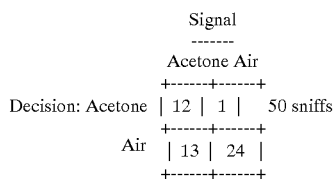

b) Smart Nose Mode

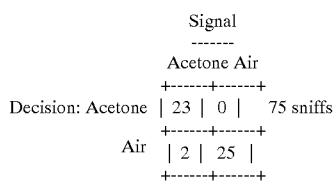

In this second example, the 'goodness' criterion was set to three. Again, the number of correct rejections was high for both modes. The more stringent 'goodness' criterion improved the number of hits to 92%, requiring 25 additional long sniffs.

Example 4

In order to demonstrate the unique sensitivity, detection, and discrimination capabilities of the sensor of the present invention, five vapor mixtures of analyte-saturated air were sampled with a nine element sensor array of the present invention and a sixteen element fiber optic sensor array for comparing the relative sensitivity and discriminating capability of the two sensing devices. Table 4.1 lists the sensor element types employed for each sensor array in the comparative testing. These sensors were fabricated according to the methods described above. The fabrication methods employed for the sensor elements and fiber optic sensor device are described previously [see J. White, et al., Anal. Chem. 68(13):2191–2202(1996)].

The response of the fiber optic sensing device to air, methanol, amyl acetate, acetyl acetate, and xylene analytes was initially evaluated using a CCD camera detection system and an enclosed, positive pressure, sample delivery method described previously (see J. White, et al., Anal. Chem. 68:2191–2202 (1996)). During sampling, the CCD gain was adjusted such that non-saturating signals were obtained from all sensors in the fiber optic array. The maximum gain which would provide detectable responses from less responsive sensors and not saturate the CCD amplifier with highly response sensors was utilized. Unlike the present invention, the fiber optic sensor employs a CCD camera detector that does not provide for adjusting the gain for each sensor element based on the sensor element response signal. This is an undesirable limitation in individual sensor response capabilities since the response signal for each sensor element in the array can not be optimized with this device. In contrast, the present sensing device has the capability for adjusting the gain of individual sensor channels to obtain maximum response signal from each sensor in the array. Such a capability is particularly advantageous when there is a significant difference in the response signals of sensor array elements to specific analytes. By providing for gain adjustment of individual sensor channels, optimum detection, discrimination, and sensor response utilization is achieved by optimizing signal response intensity and signal to noise ratios for each sensor element in the array. This capability for individually adjusting sensor element response signal is essentially impossible to achieve with the conventional CCD camera detectors that are typically employed with fiber optic sensors.

TABLE 4.1

Sensor Elements Employed for Comparative Performance Testing

| Element No. | Present Invention | Element No. | Fiber Optic Sensor |
|---|---|---|---|
| 7 | Dow/alumina | 2 | background-no polymer |
| 4 | Dow | 3 | PS802/20% MMA |
| 1 | PABS | 4 | cellulose/alumina/cellulose |
| 8 | PSAN | 5 | RMS-044/20% MMA |
| 5 | PBA | 6 | (inoperative) |
| 2 | PDPO/alumina | 7 | Dow/alumina |
| 9 | PC | 8 | Dow/alumina/PDPO |
| 6 | PC/alumina | 9 | PS802/PS901.5 |
| 3 | EC | 10 | PS802/10% MMA |
|   |   | 11 | PDPO |
|   |   | 12 | Dow (2 dips) |
|   |   | 13 | RMS-044 |
|   |   | 14 | PS901.5 |
|   |   | 15 | PS802 |
|   |   | 16 | Dow/alumina/Dow |
|   |   | 17 | Dow (5 dips) |
|   |   | 18 | (inoperative) |
|   |   | 19 | PC/PSAN/alumina |
|   |   | 20 | (inoperative) |
|   |   | 21 | cellulose/PDPO and beads |

| Abbreviations | Supplier |
|---|---|
| DOW = a dimethyl siloxane dispersion coating | Dow Corning |
| PC = polycaprolactone | Aldrich |
| PDPO = poly(2.6-dimethyl-1,4 phenylene oxide) | Aldrich |

TABLE 4.1-continued

| | |
|---|---|
| PSAN = poly styrene-acrylonitrile | Poly Sciences |
| Cellulose = ethyl cellulose | Poly Sciences |
| MMA = methyl methacrylate | Aldrich |
| PS802 = (80–85% dimethyl (15–20%) acryloxypropyl) Methylsiloxane copolymer | United Chemical Technologies |
| PS901.5 = poly (acryloxypropylmethyl) siloxane | United Chemical Technologies |
| RMS-044 = 4–6% (methacryloxypropyl) methyl-siloxane, dimethyl siloxane copolymer | United Chemical Technologies |
| PBA = poly (1,4-butylene adipate) | |

While initial sampling tests with the fiber optic sensor employed an enclosed, positive pressure chamber that contained analyte vapors, in order to make a direct comparison of the sensing performance of the two sensing devices, a small port hole was drilled into the sample chamber area of the present invention for positioning the fiber optic sensor. With this configuration, response measurements for both sensing devices could be directly compared using the same analyte sampling pulse generated by the sampling valves and fans of the present invention.

Data were acquired from both the fiber optic sensor and the present sensor while introducing odors to the sample chamber via the valve and fan assembly of the present invention. In this manner, the difference in sensitivity between the two sensors to pulses of analyte generated by the same odor delivery method could be monitored. To avoid interference during data acquisition for each sensing device, the fiber optic sensor excitation light source was turned off when acquiring data from the present sensor and the LED excitation light sources were turned off when acquiring data from the fiber optic sensor Both sensing devices employed the same sensor excitation wavelength of 530 nm (40 nm bandpass) and same sensor emission wavelength of 620 nm (20 nm bandpass) by applying excitation filters to the light source and emission filters to the detection means for each sensing device.

In comparing the fiber optic sensor response to methanol during initial testing, the amplitude of the fiber optic signal obtained within the sample chamber was generally about half the amplitude of the signal obtained using an enclosed, positive pressure sampling container which is typically used when making sample measurements with this device. While reduced response signal could be overcome by increasing detector gain settings, this was not possible with the fiber optic sensor since the CCD amplifier was set at the maximum permissible gain which would avoid CCD detector saturation from the high fluorescence background of the sensor elements. In contrast, the sensor of the present invention produced a much larger response signal to the same methanol analyte pulse. Although very large response signals may saturate the amplifier of the present sensor, it is still possible to use the full range of the A/D conversion for all the sensors in the present array since the baseline intensities for every sensors may be reset to a common value.

For the plots shown in FIGS. 24a–b, 24d, 25a–b, and 26a–c a full-scale y-axis plotting range of 4000 response intensity units was used for displaying the signal response for as a function of time for both sensing devices. This scale approximated the resolution limit for sensor response measurements since all data were digitized to 12 bits which resulted in response data values ranging from 0 to 4096 for both devices. For the fiber optic sensor, data are plotted as pixel values and for the present sensor, data are plotted as fluorescence analog/digital values.

Figure 25A:
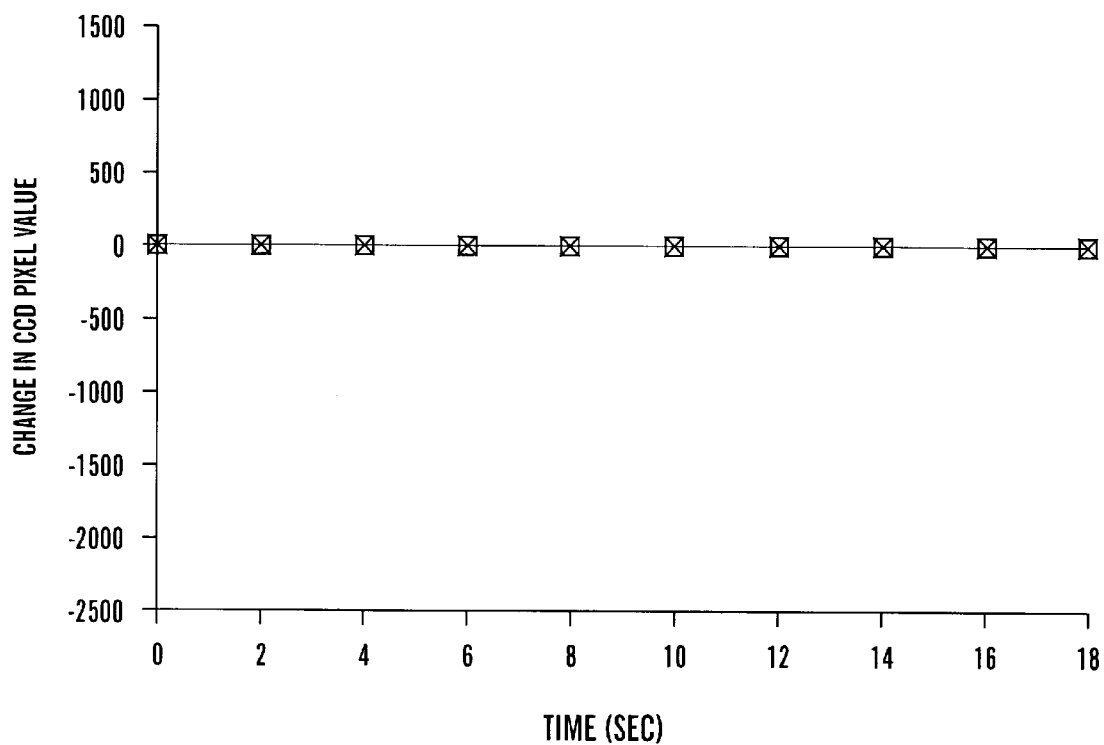
FIGS. 25a–d are plots of typical sensor fluorescence responses of a Dow sensor in a fiber optic sensor array to saturated and unsaturated amyl acetate and xylene.
Figure 25B:
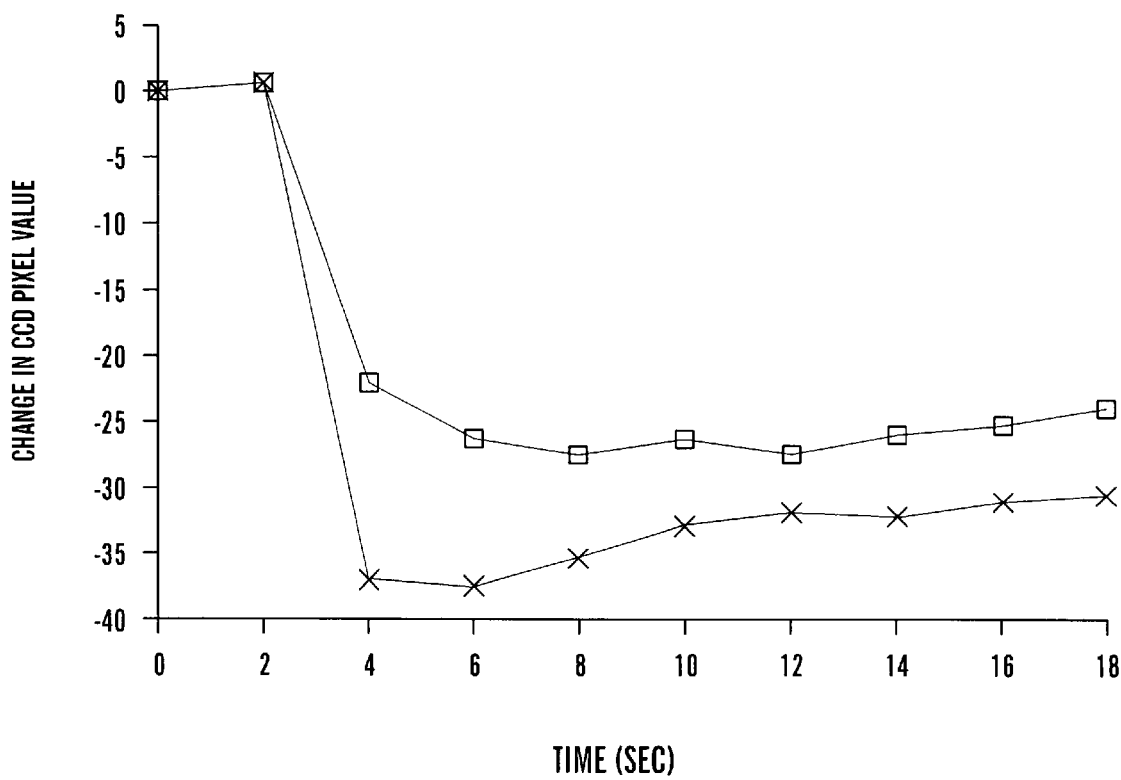
Figure 25C:
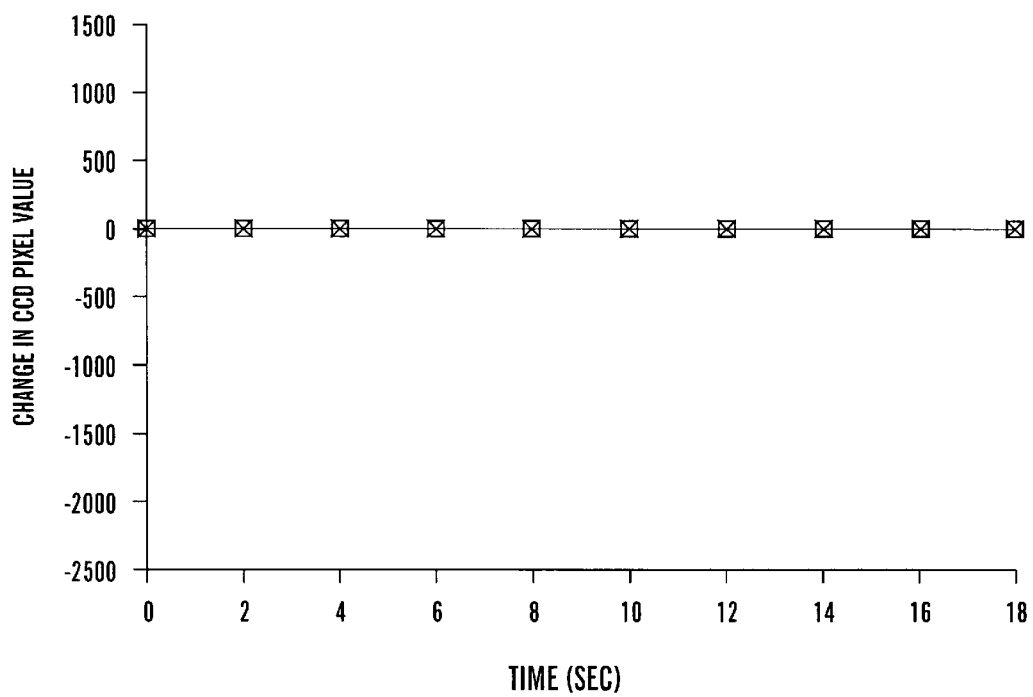
Figure 25D:
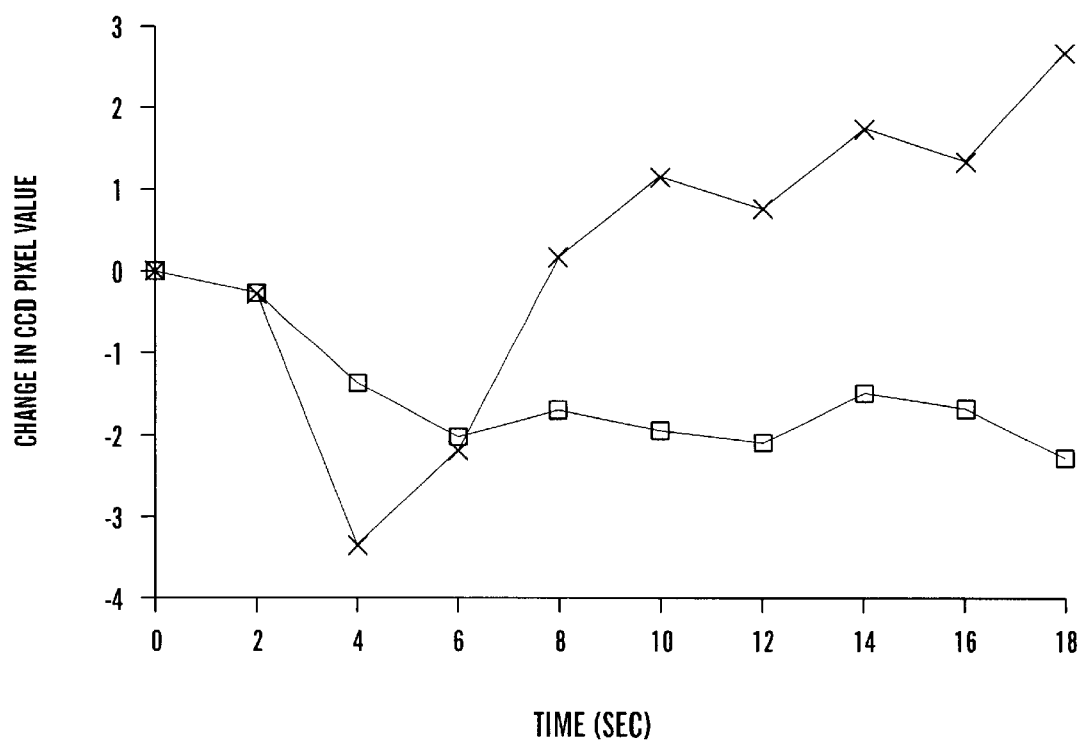
Figure 26A:
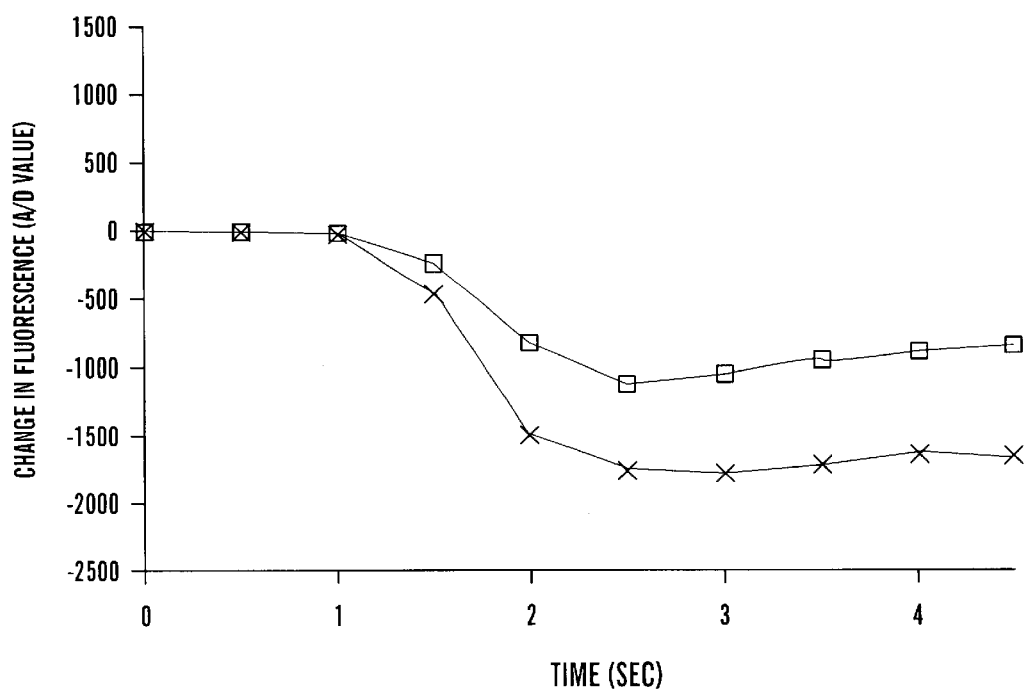
FIGS. 26a–c are plots of typical sensor fluorescence responses of Dow sensor in the sensor and sensing system of the present invention.
Figure 26B:
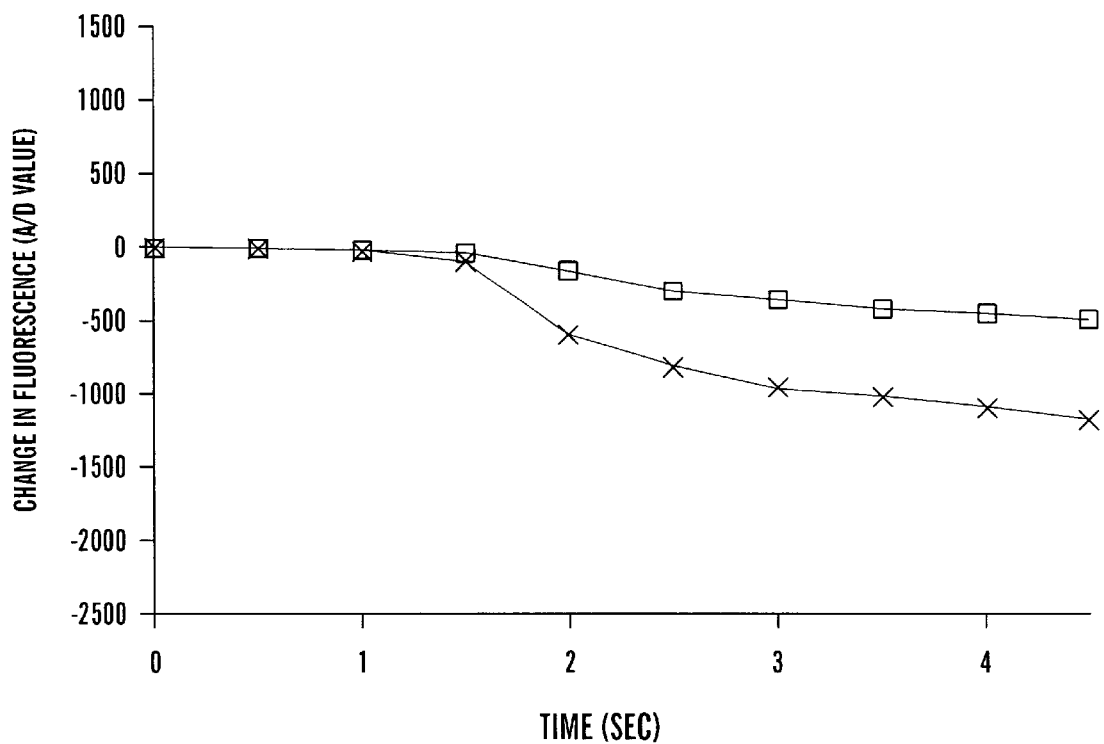
Figure 26C:
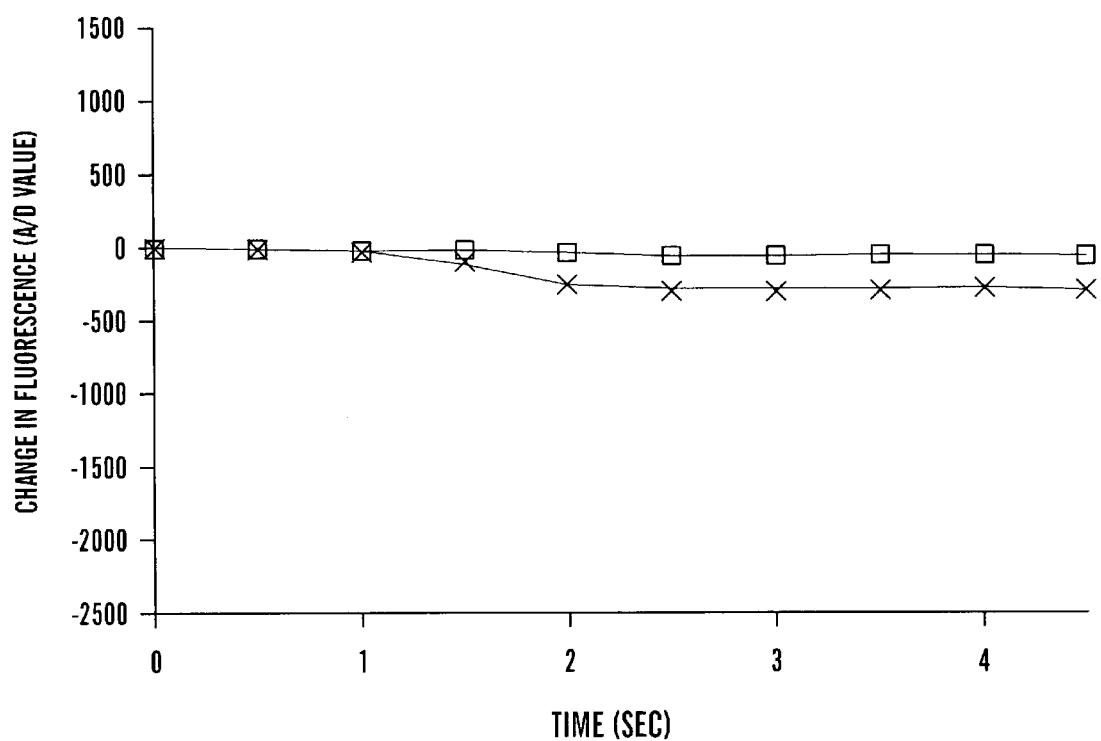

For the plots shown in FIGS. 24c, 24e, and 25c–d, due to the low response signals produced by the fiber optic sensors, a much smaller range is plotted which shows much lower signal changes than the data obtained with the present invention plotted at full scale in FIGS. 26a–c. Due to the typically slower sensor response times.observed with the fiber optic sensor, measurements were made over a 20 second time frame for this device whereas a 5 second measurement period was used for the present invention. In comparing sensing performance of the two sensor devices, the most important parameter is the relative amplitude of the signals obtained for individual sensor elements in response to analytes.

Since, as discussed above, the baseline signal for individual fiber optic sensor elements could not be reset to avoid saturation, the video gain for the fiber optic sensor measurements was set at the maximum gain that prevented the brightest sensors from saturating the CCD. This led to a compromise in response signal response for sensors in the fiber optic array since signal gain for individual sensors could not be adjusted for maximum sensitivity and resolution. Thus, response signals from sensors producing low signal could not be amplified without saturating high signal producing sensors and response signals from sensors producing high signal could not be reduced without risking loss of signal from less responsive sensors. In contrast, since the sensor of the present invention has the capability to both reset response baselines for all sensors in the array and then maximize sensor gain for all sensors, the sensor of the present invention provided much higher response signal, resolution and sensitivity for optimum sensor response to analytes.

Figure 24A:
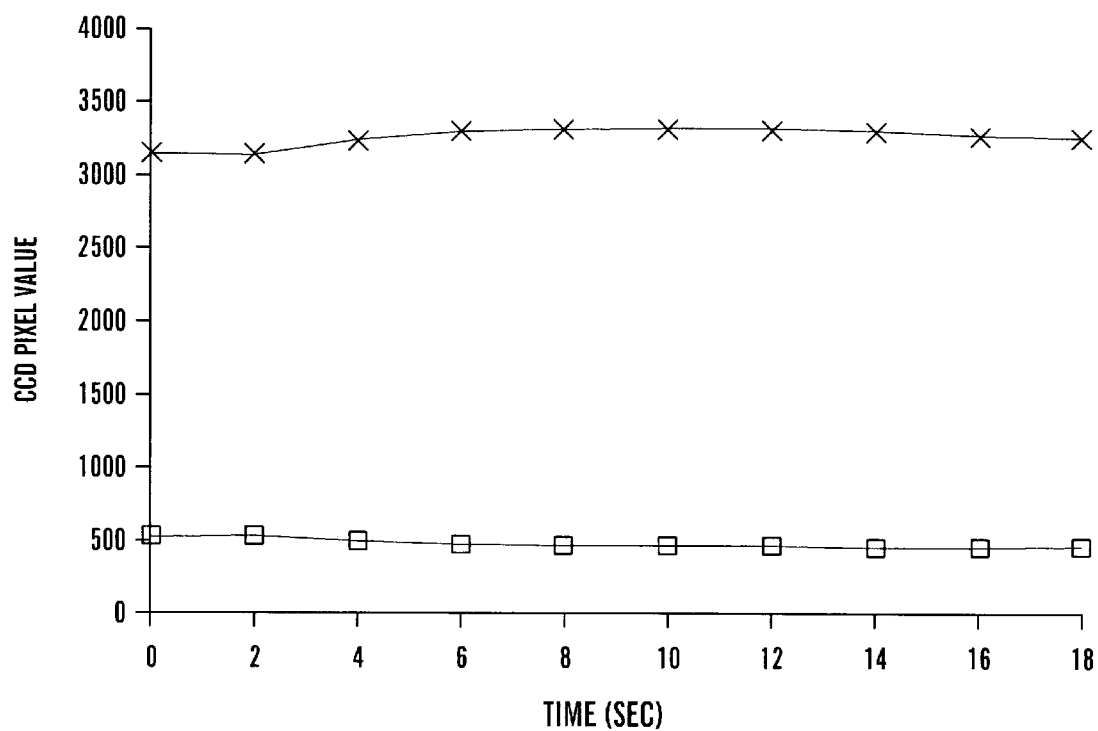
FIGS. 24a–e are plots of typical sensor fluorescence responses of Dow and cellulose-alumina sensors in a fiber optic sensor array to saturated and unsaturated methanol analyte.
Figure 24B:
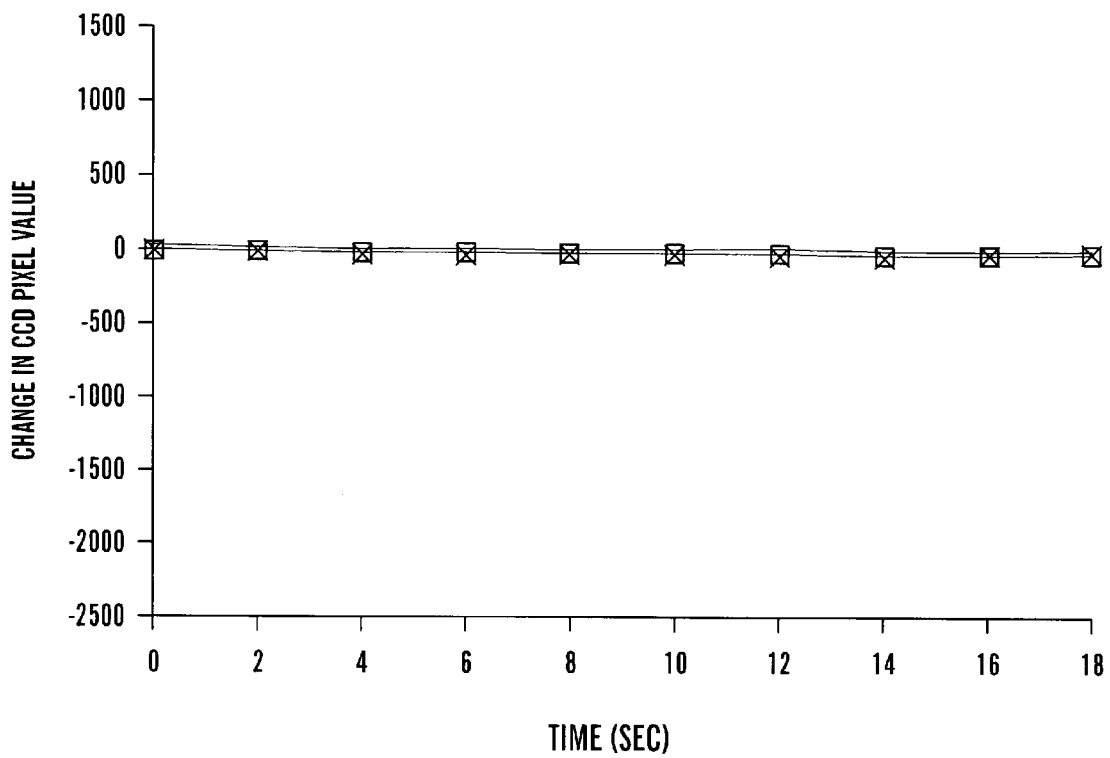
Figure 24C:
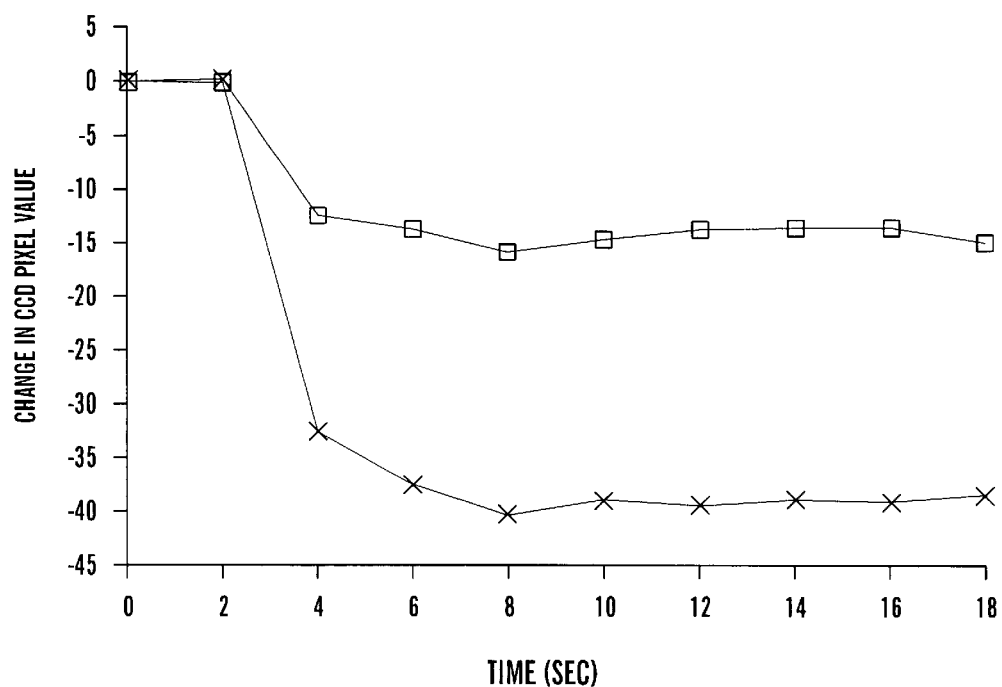
Figure 24D:
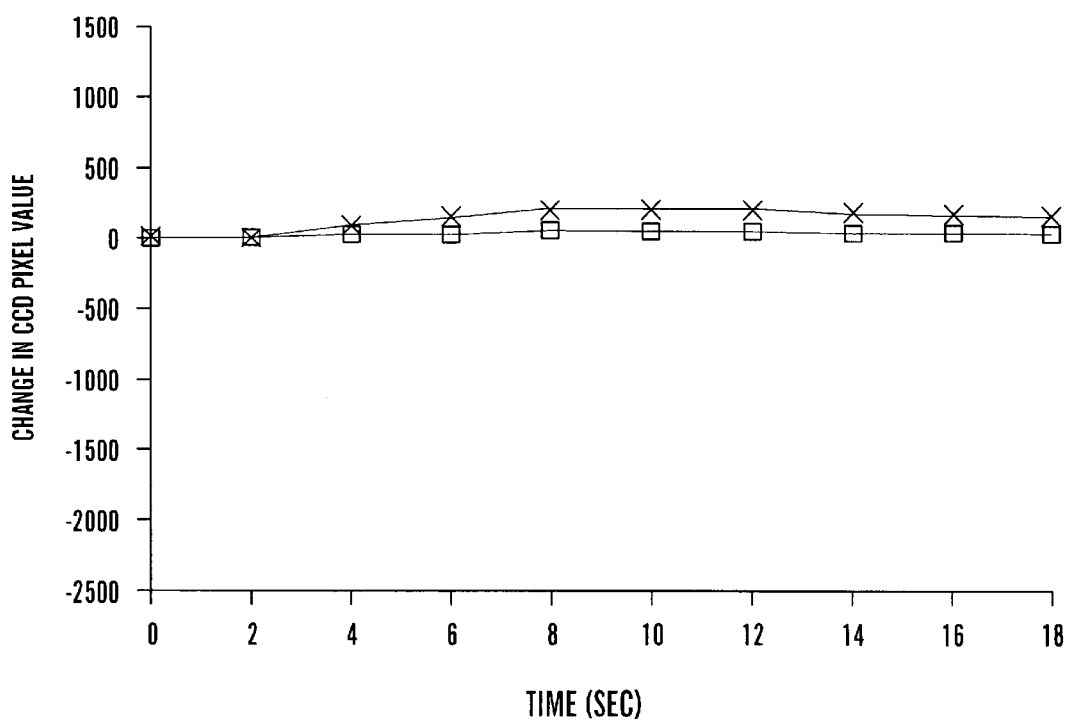
Figure 24E:
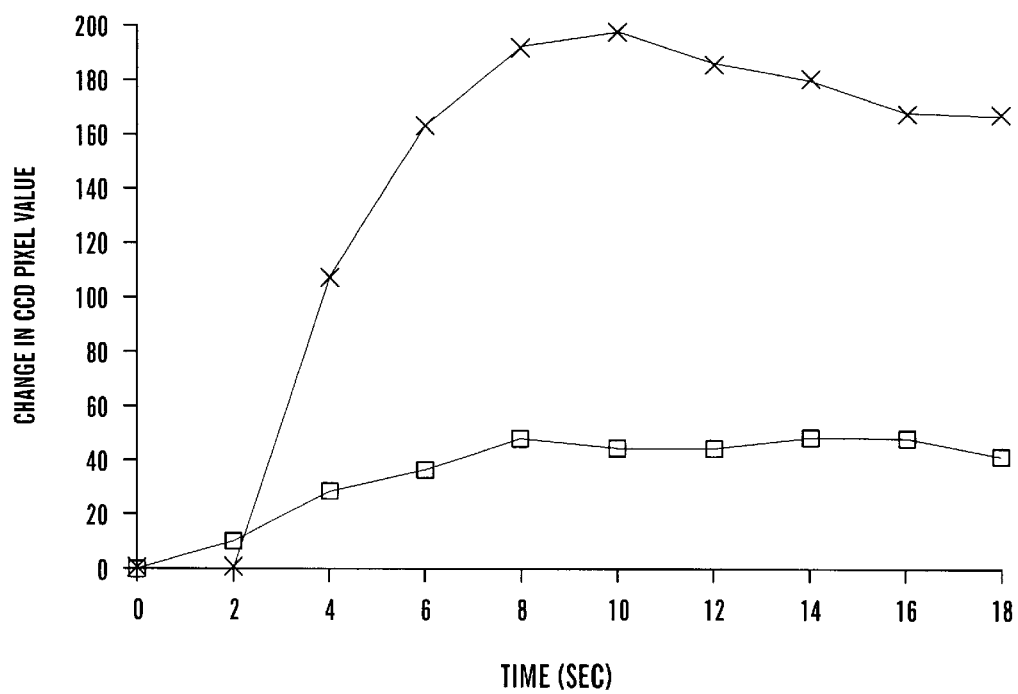

In FIGS. 24a–e, the sensor responses for two sensor elements of the fiber optic sensor, a cellulose-alumina sensor and a Dow sensor, are shown for a methanol-saturated analyte sample and a 1:10 dilution of this analyte sample. The compositions and methods for fabricating these sensors are described above. The cellulose-alumina sensor data represents the most responsive (i.e. bright) sensor observed for methanol with the fiber optic devices while the Dow sensor data represents a typical, moderately responsive (i.e. less bright) sensor. In FIG. 24a, the upper pixel intensity trace is from the bright sensor and the lower trace from the less bright sensor. This plot shows a substantial difference in intensity for the two sensors such that the gain of the Dow sensor cannot be increased without saturating the cellulose-alumina sensor, resulting in the loss of sensor reliability. The full-scale plot of FIG. 24b shows the minimal change in pixel intensity of the less bright Dow sensor upon exposure to methanol as either a saturated analyte sample or a 1:10 sample dilution. These data are replotted in FIG. 24c on a much finer scale and clearly shows the relatively low response signal of this sensor to methanol where a saturated analyte sample produces only about 40 pixel intensity unit change, or 1% of full-scale, while a dilute analyte sample produces only about a 15 unit change, or about 0.4% of full-scale. The full-scale plot of FIG. 24d shows the relatively modest change in pixel intensity of the bright cellulose-alumina sensor upon exposure to saturated methanol analyte solution and a diluted sample solution. These data are replotted in FIG. 24e on a finer scale and show a modest 200 unit increase in intensity, or 5% of full-scale, for the saturated analyte, and less than a 50 unit change, or about 1% change of full-scale, for the dilute analyte sample. In dramatic contrast to the fiber optic sensor response measurements, the increased sensitivity, resolution, and detection capability of the innovative sensor of the present invention to saturated methanol and dilute methanol analyte samples is shown in FIG. 26a where data for the less bright Dow sensor material are provided. With the present sensor, the dilute analyte exhibits about a 1100 unit change in intensity, or 25% of full-scale whereas the saturated analyte shows over a 1700 unit change in intensity, or about 43% of full-scale. With the fiber optic device, the equivalent sensor material produced only from 1 to 10% of the signal of the present invention in response to the same analyte solutions.

Similar results were observed with other analyte samples. FIGS. 25a–b show the minimal pixel intensity change of the fiber optic device to saturated and diluted amyl acetate analyte solutions where a change of only 27 to 38 intensity units was observed with the Dow sensor element. In contrast, FIG. 26b shows the significant intensity change of the present sensor device to saturated and diluted amyl acetate sample solutions where a change of 500 to 1000 intensity units was observed with the Dow sensor element. The fiber optic device apparently produced only 3–5% of the signal of the present invention in response to the same analyte solutions. FIGS. 25c–d show that the fiber optic device has an extremely low responsivity to saturated and diluted xylene analyte solutions where the response signal is relatively noisy and a change of only about three intensity units is observed for each analyte sample. In contrast, FIG. 26c shows the significant intensity change of the present sensor device to saturated and diluted xylene sample solutions where a change of about 50–250 intensity units was observed with the Dow sensor element in response to the dilute and concentrated analytes. The fiber optic device apparently produced only 1–4% of the signal of the present invention in response to the same analyte solutions.

These results demonstrate that the response signal amplitude, resolution, sensitivity, detection and discrimination capability that can be achieved with the innovative sensor of the present invention is substantially better than even the largest signal obtained from the most responsive sensor materials with fiber optic sensor devices. These data unambiguously demonstrate the enhanced detection and discrimination capability of the sensor of the present invention which provides for high signal to noise, increased sensitivity, lower detection and identification limits and greater discrimination in analyte sensing. In addition, from these results, it appears that the response time of the innovative sensor of the present invention is significantly faster than fiber optic sensor devices.

The ability to reset the amplifier in the device of the present invention provides the capability to sense from all sensors in the array simultaneously without compromising signal information from either the most responsive or least responsive elements in the array. Furthermore, this innovative feature of the sensor of the present inventions enables use of higher gain settings and reduced noise, resulting in larger response signals and improved analyte detection and discrimination capability. These response measurement results clearly demonstrate the unique and advantageous sensitivity, detection limits, and discrimination capabilities of the device of the present invention when compared to conventional sensor designs under the same test conditions.

Having described the preferred embodiments of the invention, it will now become apparent to one of skill in the art that other embodiments incorporating the concepts may be used. Therefore, it is not intended to limit the invention to the disclosed embodiments but rather the invention should be limited only by the spirit and scope of the following claims.

What is claimed is:

1. An optical sensor for detecting target analytes in a fluid, said sensor comprising:
    a fluid-permeable, signal enhancing, porous, textured substrate having a high surface area and high surface area to volume ratio, said substrate having a pore size distribution comprising substantially open pores; and
    a sensor material dispersed on a plurality of internal and external surfaces within said substrate, said sensor material providing a characteristic optical response when subjected to excitation light energy in the presence of target analytes, said substrate open porosity and fluid permeability providing essentially free, unimpeded access for transport of analyte-containing fluids to said sensor material, said substrate providing enhanced responsivity, selectivity and discrimination of said sensor to said target analytes.

2. The sensor of claim 1 wherein said dye substrate is comprised of a fibrous material.

3. The sensor of claim 2 wherein said fibrous material is selected from the group consisting of papers, tissues, textiles, woven fabrics, felts, fibers, fiber bundles, composites, and laminates of the same.

4. The sensor of claim 1 wherein said dye substrate is comprised of a particulate material.

5. The sensor of claim 4 wherein said particulate is selected from the group consisting of glasses, silicas, aluminas, ceramics, polymers, plastics, metals, composites, sintered powders, and fritted assemblages of the same.

6. The sensor of claim 1 wherein said sensor material comprises a fluorescent dye.

7. The sensor of claim 6 wherein said sensor material further comprises a polymer.

8. The sensor of claim 6 wherein said fluorescent dye is a solvatochromic dye.

9. The sensor of claim 8 wherein said solvatochromic dye is selected from the group consisting of Nile Red, Prodan, 6-propionyl-2-(N,N-dimethylamino) napthalene, Acrylodan, and 6-acryloyl(dimethylamino) napthalene.

10. A cross-reactive sensor array for detecting target analytes in a fluid, said sensor array comprising:
    a plurality of fluid-permeable, signal enhancing, porous, textured substrates having a high surface area and high surface area to volume ratio, said substrates having a pore size distribution comprising substantially open pores; and
    a plurality of sensor materials, each one of said sensor materials dispersed on a plurality of internal and external surfaces within at least one of said substrates, each of said sensor materials providing a characteristic optical response when subjected to excitation light energy in the presence of target analytes, each combination of one of said substrates with one of said sensor materials forming a discrete sensor array element, each of said substrates providing essentially free, unimpeded access for transport of analyte-containing fluids to each of said dispersed sensor materials, each of said substrates providing enhanced responsivity, selectivity and discrimination of said sensor elements to said target analytes.

11. The sensor array of claim 10 wherein said dye substrates are comprised of a fibrous material.

12. The sensor array of claim 11 wherein said fibrous material is selected from the group consisting of papers, tissues, textiles, woven fabrics, felts, fibers, fiber bundles, composites, and laminates of the same.

13. The sensor array according to claim 11 further comprising an optical detector array comprised of a plurality of individual detectors, each detector being optically coupled to a single sensor element.

14. The sensor array of claim 13 wherein said detector array comprises an array of filtered photodiodes.

15. The sensor array of claim 10 wherein said dye substrates are comprised of a particulate material.

16. The sensor array of claim 15 wherein said particulate is selected from the group consisting of glasses, silicas, aluminas, ceramics, polymers, plastics, metals, composites, sintered powders, and fritted assemblages of the same.

17. The sensor array of claim 10 wherein at least one of said sensor materials comprises a fluorescent dye.

18. The sensor array of claim 17 wherein at least one of said sensor materials further comprises a polymer.

19. The sensor array of claim 17 wherein said fluorescent dye is a solvatochromic dye selected from the group consisting of Nile Red, Prodan, 6-propionyl-2-(N,N-dimethylamino)napthalene, Acrylodan, and 6-acryloyl (dimethylamino) napthalene.

20. The sensor array according to claim 10 further comprising an excitation light source array comprised of a plurality of individual light sources, each light source being optically coupled to a single sensor element.

21. The sensor array of claim 20 wherein said light source array comprises an array of filtered light emitting diodes.

22. A method for detecting target analytes in a fluid comprising the steps of:
   contacting said sample with a cross-reactive sensor array comprised of
      a plurality of fluid-permeable, signal enhancing, porous, textured substrates having a high surface area and high surface area to volume ratio, said substrates having a pore size distribution comprising substantially open pores; and
      a plurality of sensor materials, each one of said sensor materials dispersed on a plurality of internal and external surfaces within at least one of said substrates, each of said sensor materials providing a characteristic optical response when subjected to excitation light energy in the presence of target analytes, each combination of at least one of said substrates with at least one of said sensor materials forming a discrete sensor array element, each of said substrates providing essentially free, unimpeded access for transport of analyte-containing fluids to each of said dispersed sensor materials, each of said substrates providing enhanced responsivity, selectivity and discrimination of said sensor elements to said target analytes; and
   detecting the presence or absence of said target analytes from a plurality of characteristic optical response signals produced by a plurality of said sensor elements.

23. The method of claim 22 wherein said contacting further comprises drawing said fluid into a sample chamber and exposing said array to said fluid for no more than five seconds.

24. The method of claim 22 wherein said detecting further comprises:
   illuminating said sensors with an array of individual excitation light sources, each light source being optically coupled to a single sensor element; and
   measuring an optical response produced by said sensors due to the presence of said analyte with a detector means.

25. The method of claim 24 further comprising identifying said analyte by
   employing a pattern-matching algorithm; and
   comparing said optical response of said sensor with said characteristic optical response.

26. The method of claim 24 further comprising identifying said analyte by
   providing spatio-temporal response patterns of said optical response; and
   recognizing said patterns through a method selected from the group consisting of a template matching, neural networks, delay line neural networks, or statistical analysis.

27. A method for detecting target analytes in a fluid comprising the steps of:
   providing a cross-reactive sensor array comprising,
      a plurality of fluid-permeable, signal enhancing, porous, textured substrates having a high surface area and high surface area to volume ratio, said substrates having a pore size distribution comprising substantially open pores; and
      a plurality of sensor materials, each one of said sensor materials dispersed on a plurality of internal and external surfaces within at least one of said substrates, each of said sensor materials providing a characteristic optical response when subjected to excitation light energy in the presence of target analytes, each combination of at least one of said substrates with at least one of said sensor materials forming a discrete sensor array element, each of said substrates providing essentially free, unimpeded access for transport of analyte-containing fluids to each of said dispersed sensor materials, each of said substrates providing enhanced responsivity, selectivity and discrimination of said sensor elements to said target analytes;
   setting primary sampling parameters for said sensor array;
   contacting said fluid with said array;
   detecting a first plurality of optical responses produced by interaction of said fluid with said array sensors;
   comparing said first plurality of responses to a first stored spatio-temporal response for said primary parameters for said analytes;
   setting secondary sampling parameters for said array wherein at least one sampling parameter is changed;
   detecting a second plurality of optical responses produced by interaction of said fluid with said sensor elements;
   comparing said second plurality of responses to a second stored spatio-temporal response for said secondary parameters for said analytes; and
   detecting the presence or absence of said analytes.

28. The method of claim 27 wherein said setting primary sampling parameters comprises:
   adjusting an excitation light source to a non-zero minimum intensity;
   setting a fluid sampling time to a non-zero minimum time;
   adjusting said fluid flow to a non-zero minimum flow rate;
   setting a number of sampling time points to a non-zero minimum; and
   setting a number of sniff samples to a maximum.

29. The method of claim 27 wherein said setting secondary sampling parameters comprises:
   incrementing said number of sniff samples by at least one;
   selecting said at least one parameter setting from the group consisting of amplifier gain, fluid sampling time, fluid flow rate, number of sampling time points, sample sniff rate, amplifier high pass filtering, excitation light source intensity, and exhale velocity; and modifying said at least one parameter setting from an initial setting value.

30. A sensing system for detecting and identifying analytes in a fluid comprising:
a cross-reactive sensor array comprised of
a plurality of fluid-permeable, signal enhancing, porous, textured substrates having a high surface area and high surface area to volume ratio, said substrates having a pore size distribution comprising substantially open pores; and
a plurality of sensor materials, each one of said sensor materials dispersed on a plurality of internal and external surfaces within at least one of said substrates, each of said sensor materials providing a characteristic optical response when subjected to excitation light energy in the presence of target analytes, each combination of at least one of said substrates with at least one of said sensor materials forming a discrete sensor array element, each of said substrates providing essentially free, unimpeded access for transport of analyte-containing fluids to each of said dispersed sensor materials, each of said substrates providing enhanced responsivity, selectivity and discrimination of said sensor elements to said target analytes;
an excitation light source array comprising a plurality of individual light sources, each light source being optically coupled to one sensor element;
an optical detector array comprising a plurality of individual detectors, each detector being optically coupled to one sensor element;
a sample chamber for housing said sensor array, said light source array and said detector array;
a sampling means enclosed in said chamber for drawing said fluid into said chamber for contact with said sensor array for a controlled exposure time;
a controller means in electrical communication with said light sources, said detectors, and said sampling means, said controller means electrically coordinating and switching said sampling means with said light sources and said detectors for sampling said fluid, measuring optical responses of said sensor elements to said fluid, and detecting said analytes; and
an analyte identification algorithm for comparing said measured sensor optical responses to characteristic optical responses of said sensor elements to target analytes and identifying said analytes in said fluid.

31. The sensing system of claim 30 wherein said light source array comprises an array of filtered light emitting diodes and said detector array comprises an array of filtered photodiodes.

32. A smart sensing system for intelligent detecting and identifying analytes in a fluid comprising:
a cross-reactive sensor array comprised of
a plurality of fluid-permeable, signal enhancing, porous, textured substrates having a high surface area and high surface area to volume ratio, said substrates having a pore size distribution comprising substantially open pores; and
a plurality of sensor materials, each one of said sensor materials dispersed on a plurality of internal and external surfaces within at least one of said substrates, each of said sensor materials providing a characteristic optical response when subjected to excitation light energy in the presence of target analytes, each combination of at least one of said substrates with at least one of said sensor materials forming a discrete sensor array element, each of said substrates providing essentially free, unimpeded access for transport of analyte-containing fluids to each of said dispersed sensor materials, each of said substrates providing enhanced responsivity, selectivity and discrimination of said sensor elements to said target analytes;
an excitation light source array comprising a plurality of individual light sources, each light source being optically coupled to one sensor element;
an optical detector array comprising a plurality of individual detectors, each detector being optically coupled to one sensor element;
a sampling chamber for housing said sensor array, said light source array and said detector array;
a sampling means enclosed in said chamber for drawing said fluid into said chamber for contact with said sensor array for a controlled exposure time;
a microcontroller in electrical communication with said sampling means, said light source array and said detector array, said controller means electrically coordinating and switching said sampling means, said light source array and said detector array for sampling said fluid, for measuring responses of said sensor elements to said fluid, for detecting said analytes and for reporting analyte detection results;
an intelligent sampling algorithm for directing said microcontroller, said sampling algorithm selecting sensors, light sources and detectors, said sampling algorithm coordinating said microcontroller electrical communication for said switching, said sampling, said measuring, said detecting and said reporting, said sampling algorithm setting first and second sampling parameters; and
an analyte identification algorithm in communication with said sampling algorithm and said microcontroller, said identification algorithm comparing said measured sensor optical responses to characteristic responses of said sensor elements to target analytes and identifying said analytes in said sample.

33. The sensing system of claim 32 wherein said light source array comprises an array of filtered light emitting diodes and said detector array comprises an array of filtered photodiodes.

34. The sensing system of claim 32 wherein said identification algorithm comprises a response report comparing a spatio-temporal pattern of said measured optical responses to a spatio-temporal pattern of said characteristic responses; and
an identification report selected from the group consisting of a pattern match, a delay line neural network match, and a neuronal network match.

* * * * *